(12) United States Patent
Denton et al.

(10) Patent No.: US 6,770,645 B2
(45) Date of Patent: Aug. 3, 2004

(54) PHARMACEUTICALLY ACTIVE COMPOUNDS

(75) Inventors: Stephen Martin Denton, Sandwich (GB); Mark Ian Kemp, Sandwich (GB); Sandra Dora Newman, Sandwich (GB); David James Rawson, Sandwich (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/096,190

(22) Filed: Mar. 12, 2002

(65) Prior Publication Data

US 2003/0064990 A1 Apr. 3, 2003

Related U.S. Application Data

(60) Provisional application No. 60/290,723, filed on May 14, 2001.

(30) Foreign Application Priority Data

Mar. 16, 2001 (GB) .............................. 0106661

(51) Int. Cl.$^7$ .................... C07D 487/04; C07D 239/00; A61K 31/505
(52) U.S. Cl. ............... 514/242; 514/262.1; 514/263.22; 514/263.3; 544/184; 544/262; 544/265; 544/276
(58) Field of Search ................ 544/184, 262, 544/265, 276; 514/243, 262.1, 263.22, 263.3

(56) References Cited

U.S. PATENT DOCUMENTS

| | | | |
|---|---|---|---|
| 4,039,544 A | 8/1977 | Broughton | ............... 260/256.4 |
| 4,666,908 A | 5/1987 | Hamilton | ..................... 514/229 |
| 6,225,315 B1 * | 5/2001 | Ellis | ........................... 514/250 |

FOREIGN PATENT DOCUMENTS

| | | | | |
|---|---|---|---|---|
| EP | 0352960 | | 7/1989 | ......... C07D/473/30 |
| EP | 0442204 | | 12/1990 | ......... A61K/487/04 |
| EP | 1022026 | * | 7/2000 | |
| WO | WO 0127112 | | 10/1999 | ......... C07D/487/04 |
| WO | WO 01/27112 | * | 4/2001 | |

OTHER PUBLICATIONS

Corbin et al., PubMed Abstract, 2002.*
Uckert et al., PubMed Abstract, 2001.*
Layzer, Degenerative Diseases of the Nervous System, Cecil Textbook of Medicine, 20th Edition, vol. 2, pp. 2050–2057, 1996.*

Damasio, Alzheimer's Disease and related dementias, Cecil Textbook of Medicine, 20th Edition, vol. 2, pp. 1992–1996, 1996.*

Ellis, CAPLUS Abstract 133:22405, 2000.*

Broughton, J. Med. Chem., 1975, vol. 18, No. 11, pp. 1117–1122.

Database Chem Abstract, Ellis Peter, XP002198398; Acc. No. 133:22405, 2000.

"Making the Love Drug", in Chembytes e–zine No. 1, 1999; http://www/chemsoc.org/chembytes/ezi.

Terrett, NK, et al, Bioorganic and Medicinal Chemistry Letters, vol. 6(15)(Aug. 6, 1996)1819–1824.

Chem Abs Acc No 96:51500 (Wilson J.Am.Chem. Soc. 1982, 104(1), 259–264.

* cited by examiner

Primary Examiner—Deepak Rao
(74) Attorney, Agent, or Firm—Peter C. Richardson; Gregg C. Benson; A. Dean Olson

(57) ABSTRACT

Compound of general formula I:

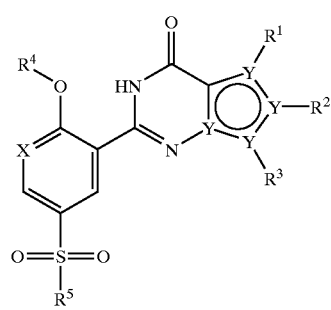

wherein $R^1$, $R^2$, $R^3$, $R^4$, X, Y and $R^5$ have the meanings given herein which are useful in the curative and prophylactic treatment of a medical condition for which inhibition of a cyclic guanosine 3',5'-monophosphate phosphodiesterase (e.g. cGMP PDE5) is desired.

13 Claims, No Drawings

PHARMACEUTICALLY ACTIVE COMPOUNDS

This application claims priority from U.K. Application 0106661.2 filed Mar. 16, 2001 and U.S. Provisional Application No. 60/290,723 filed May 14, 2001.

FIELD OF THE INVENTION

This invention relates to pharmaceutically useful compounds which inhibit cyclic guanosine 3',5'-monophosphate phosphodiesterases (cGMP PDEs). More notably, the compounds of the invention are potent inhibitors of type 5 cyclic guanosine 3',5'-monophosphate phosphodiesterase (cGMP PDE5) and are selective over other phosphodiesterases, including PDE6. The compounds of the invention therefore have utility in a variety of therapeutic areas.

The compounds of the invention are of value for the curative or prophylactic treatment of mammalian sexual disorders. In particular, the compounds are of value in the treatment of mammalian sexual dysfunctions such as male erectile dysfunction (MED), impotence, female sexual dysfunction (FSD), clitoral dysfunction, female hypoactive sexual desire disorder, female sexual arousal disorder, female sexual pain disorder or female sexual orgasmic dysfunction (FSOD) as well as sexual dysfunction due to spinal cord injury or selective serotonin re-uptake inhibitor (SSRI) induced sexual dysfunction but, clearly, will be useful also for treating other medical conditions for which a potent and selective cGMP PDE5 inhibitor is indicated. Such conditions include premature labour, dysmenorrhoea, benign prostatic hyperplasia (BPH), bladder outlet obstruction, incontinence, stable, unstable and variant (Prinzmetal) angina, hypertension, pulmonary hypertension, chronic obstructive pulmonary disease, coronary artery disease, congestive heart failure, atherosclerosis, conditions of reduced blood vessel patency, e.g. post-percutaneous transluminal coronary angioplasty (post-PTCA), peripheral vascular disease, stroke, nitrate induced tolerance, bronchitis, allergic asthma, chronic asthma, allergic rhinitis, diseases and conditions of the eye such as glaucoma, optic neuropathy, macular degeneration, elevated intra-occular pressure, retinal or arterial occulsion and diseases characterised by disorders of gut motility, e.g. irritable bowel syndrome (IBS).

Further medical conditions for which a potent and selective cGMP PDE5 inhibitor is indicated, and for which treatment with compounds of the present invention may be useful, include pre-eclampsia, Kawasaki's syndrome, nitrate tolerance, multiple sclerosis, diabetic nephropathy, neuropathy including autonomic and peripheral neuropathy and in particular diabetic neuropathy and symptoms thereof (e.g. gastroparesis), peripheral diabetic neuropathy, Alzheimer's disease, acute respiratory failure, psoriasis, skin necrosis, cancer, metastasis, baldness, nutcracker oesophagus, anal fissure, haemorrhoids, hypoxic vasoconstriction, hypoxic vasoconstriction, diabetes, type 2 diabetes mellitus, the insulin resistance syndrome, insulin resistance, impaired glucose tolerance, as well as the stabilisation of blood pressure during haemodialysis.

Particularly preferred sexual disorders include MED and FSD.

DISCLOSURE OF THE INVENTION

According to the present invention, there is provided compounds of general formula I:

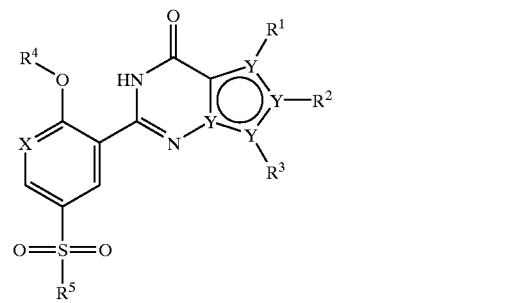

or a pharmaceutically or veterinarily acceptable salt and/or solvate, polymorph or pro-drug thereof, wherein Y represents C or N, with N being in at least one, but not more than two, of the positions marked by Y;

X represents CH or N;

$R^1$, $R^2$ and $R^3$ where present and attached to nitrogen independently represent H, $C_1$–$C_6$ alkyl, Het, $C_1$–$C_6$ alkylHet, aryl or $C_1$–$C_6$ alkylaryl;

$R^1$, $R^2$ and $R^3$ where present and attached to carbon independently represent H, halo, cyano, nitro, $OR^6$, $OC(O)R^6$, $C(O)R^6$, $C(O)OR^6$, $NR^6C(O)NR^7R^8$, $NR^6(O)OR^6$ $OC(O)NR^7R^8$, $C(O)NR^9R^{10}$, $NR^9R^{10}$, $SO_2NR^9R^{10}$, $SO_2R^{11}$, $C_1$–$C_6$ alkyl, Het, $C_1$–$C_6$ alkylHet, aryl or $C_1$–$C_6$ alkylaryl;

wherein when $R^1$ and $R^2$ are present they may optionally be connected via a C—C, C—N or C—O bond;

wherein when $R^2$ and $R^3$ are present they may optionally be connected via a C—C, C—N or C—O bond;

$R^4$ represents H, $C_1$–$C_6$ alkyl, Het, $C_1$–$C_6$ alkylHet, aryl or $C_1$–$C_6$ alkylaryl;

$R^5$ represents $C_1$–$C_6$ alkyl, Het, $C_1$–$C_6$ alkylHet, aryl or $C_1$–$C_6$ alkylaryl;

wherein when $R^1$, $R^2$ and $R^3$, where present, or $R^4$ or $R^5$ is a $C_1$–$C_6$ alkyl, Het, $C_1$–$C_6$ alkylHet, aryl and $C_1$–$C_6$ alkylaryl group, such $C_1$–$C_6$ alkyl, Het, $C_1$–$C_6$ alkylHet, aryl and $C_1$–$C_6$ alkylaryl group is optionally substituted and/or terminated with one or more substituents selected from halo, cyano, nitro, $OR^6$, $OC(O)R^6$, $C(O)R^6$, $C(O)OR^6$, $NR^6C(O)NR^7R^8$, $NR^6C(O)OR^6$, $OC(O)NR^7R^8$, $C(O)NR^9R^{10}$, $NR^9R^{10}$, $SO_2NR^9R^{10}$, $SO_2R^{11}$, $C_1$–$C_6$ alkyl, Het, $C_1$–$C_6$ alkylHet, aryl or $C_1$–$C_6$ alkylaryl which latter five substituent groups are all optionally substituted and/or terminated with one or more substituents selected from halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$, $SO_2R^{17}$;

$R^6$ represents H, $C_1$–$C_6$ alkyl, Het, $C_1$–$C_6$ alkylHet, aryl or $C_1$–$C_6$ alkylaryl which latter five substituent groups are all optionally substituted and/or terminated with one or more substituents selected from halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$, $SO_2R^{17}$;

R⁷ and R⁸ independently represent H, C₁–C₆ alkyl, Het, C₁–C₆ alkylHet, aryl or C₁–C₆ alkylaryl which latter five substituent groups are all optionally substituted and/or terminated with one or more substituents selected from halo, cyano, nitro, OR¹², OC(O)R¹², C(O)R¹², C(O)OR¹², NR¹²C(O)NR¹³R¹⁴, NR¹²C(O)OR, OC(O)NR¹³R¹⁴, C(O)NR¹⁵R¹⁶, NR¹⁵R¹⁶, SO₂NR¹⁵R¹⁶, SO₂R¹⁷; or R⁷ and R⁸ together with the nitrogen atom to which they are bound can form a heterocyclic ring which is optionally substituted and/or terminated with one or more substituents selected from halo, cyano, nitro, OR¹², OC(O)R¹², C(O)R¹². C(O)OR¹², NR¹²C(O)NR¹³R¹⁴, NR¹²C(O)OR¹², OC(O)NR¹³R¹⁴, C(O)NR¹⁵R¹⁶, NR¹⁵R¹⁶, SO₂NR¹⁵R¹⁶, SO₂R¹⁷;

R⁹ and R¹⁰ independently represent H, C(O)R⁶, SO₂R¹¹, C₁–C₆ alkyl, Het, C₁–C₆ alkylHet, aryl or C₁–C₆ alkylaryl which latter five substituent groups are all optionally substituted and/or terminated with one or more substituents selected from halo, cyano, nitro, OR¹², OC(O)R¹², C(O)R¹², C(O)OR¹², NR¹²C(O)NR¹³R¹⁴, NR¹²C(O)OR¹², OC(O)NR¹³R¹⁴, C(O)NR¹⁵R¹⁶, NR¹⁵R¹⁶, SO₂NR¹⁵R¹⁶, SO₂R¹⁷; or R⁹ and R¹⁰ together with the nitrogen atom to which they are bound can form a heterocyclic ring which is optionally substituted and/or terminated with one or more substituents selected from halo, cyano, nitro, OR¹², OC(O)R¹², C(O)R¹², C(O)OR¹², NR¹²C(O)NR¹³R¹⁴, NR¹²C(O)OR¹², OC(O)NR¹³R¹⁴, C(O)NR¹⁵R¹⁶, NR¹⁵R¹⁶, SO₂NR¹⁵R¹⁶, SO₂R¹⁷;

R¹¹ represents C₁–C₆ alkyl, Het, C₁–C₆ alkylHet, aryl or C₁–C₆ alkylaryl which latter five substituent groups are all optionally substituted and/or terminated with one or more substituents selected from halo, cyano, nitro, OR¹², OC(O)R¹², C(O)R¹², C(O)OR¹², NR¹²C(O)NR¹³R¹⁴, NR¹²C(O)OR¹², OC(O)NR¹³R¹⁴, C(O)NR¹⁵R¹⁶, NR¹⁵R¹⁶, SO₂NR¹⁵R¹⁶, SO₂R¹⁷;

R¹² represents H or C₁–C₆ alkyl;

R¹³ and R¹⁴ independently represent H or C₁–C₆ alkyl; or

R¹³ and R¹⁴ together with the nitrogen atom to which they are bound can form a heterocyclic ring;

R¹⁵ and R¹⁶ independently represent H, C(O)R¹², SO₂R¹⁷ or C₁–C₆alkyl; or

R¹⁵ and R¹⁶ together with the nitrogen atom to which they are bound can form a heterocyclic ring;

R¹⁷ represents C₁–C₆ alkyl;

Het represents an optionally substituted four- to twelve-membered heterocyclic group, which group contains one or more heteroatoms selected from nitrogen, oxygen, sulfur and mixtures thereof and with the proviso that when R⁵ is Het, said Het is C-linked to the sulphur atom of the SO₂ group in general formula I which compounds are referred to together hereinafter as "the compounds of the invention".

According to the present invention compounds of the general formula (I) R¹, R² and R³ are only present where valency allows that this can be accommodated without Y being charged.

Preferred compounds of general formula I can be represented by general formulae IA, IB, IC, ID and IE:

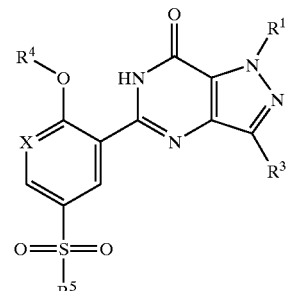

IA

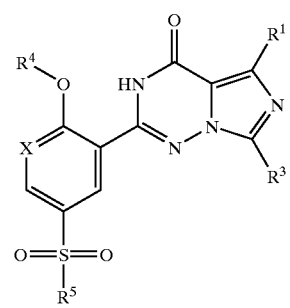

IB

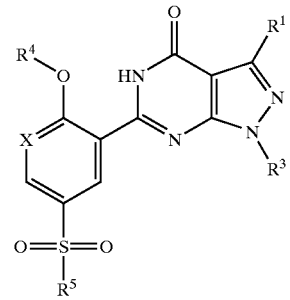

IC

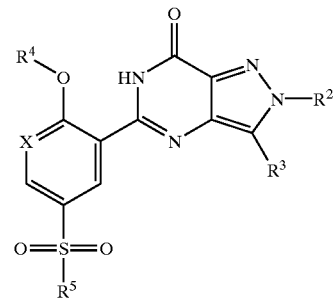

ID

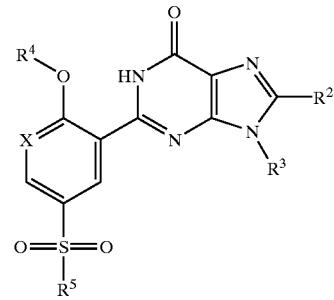

IE

Thus according to a preferred aspect of the present invention there are provided compounds of general formulae 1A, 1B, 1C, 1D and 1E wherein:

X represents CH or N;

$R^1$, $R^2$ and $R^3$ where present and attached to nitrogen independently represent H, $C_1$–$C_6$ alkyl, Het, $C_1$–$C_6$ alkylHet, aryl or $C_1$–$C_6$ alkylaryl;

$R^1$, $R^2$ and $R^3$ where present and attached to carbon independently represent H, halo, cyano, nitro, $OR^6$, $OC(O)R^6$, $C(O)R^6$, $C(O)OR^6$, $NR^6C(O)NR^7R^8$, $NR^6C(O)OR^6$, $OC(O)NR^7R^8$, $C(O)NR^9R^{10}$, $NR^9R^{10}$, $SO_2NR^9R^{11}$, $SO_2R^{11}$, $C_1$–$C_6$ alkyl, Het, $C_1$–$C_6$ alkylHet, aryl or $C_1$–$C_6$ alkylaryl;

wherein when $R^1$ and $R^2$ are present they may optionally be connected via a C—C, C—N or C—O bond;

wherein when $R^2$ and $R^3$ are present they may optionally be connected via a C—C, C—N or C—O bond;

$R^4$ represents H, $C_1$–$C_6$ alkyl, Het, $C_1$–$C_6$ alkylHet, aryl or $C_1$–$C_6$ alkylaryl;

$R^5$ represents $C_1$–$C_6$ alkyl, Het, $C_1$–$C_6$ alkylHet, aryl or $C_1$–$C_6$ alkylaryl;

wherein when R, $R^2$ and $R^3$, where present, or $R^4$ or $R^5$ is a $C_1$–$C_6$ alkyl, Het, $C_1$–$C_6$ alkylHet, aryl and $C_1$–$C_6$ alkylaryl group, such $C_1$–$C_6$ alkyl, Het, $C_1$–$C_6$ alkylHet, aryl and $C_1$–$C_6$ alkylaryl group is optionally substituted and/or terminated with one or more substituents selected from halo, cyano, nitro, $OR^6$, $OC(O)R^6$, $C(O)R^6$, $C(O)OR^6$, $NR^6C(O)NR^7R^8$, $NR^6C(O)OR^6$, $OC(O)NR^7R^8$, $C(O)NR^9R^{10}$, $NR^9R^{10}$, $SO_2NR^9R^{10}$, $SO_2R^{11}$, $C_1$–$C_6$ alkyl, Het, $C_1$–$C_6$ alkylHet, aryl or $C_1$–$C_6$ alkylaryl which latter five substituent groups are all optionally substituted and/or terminated with one or more substituents selected from halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$, $SO_2R^{17}$;

$R^6$ represents H, $C_1$–$C_6$ alkyl, Het, $C_1$–$C_6$ alkylHet, aryl or $C_1$–$C_6$ alkylaryl which latter five substituent groups are all optionally substituted and/or terminated with one or more substituents selected from halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$, $SO_2R^{17}$;

$R^7$ and $R^8$ independently represent H, $C_1$–$C_6$ alkyl, Het, $C_1$–$C_6$ alkylHet, aryl or $C_1$–$C_6$ alkylaryl which latter five substituent groups are all optionally substituted and/or terminated with one or more substituents selected from halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$, $SO_2R^{17}$; or $R^7$ and $R^8$ together with the nitrogen atom to which they are bound can form a heterocyclic ring which is optionally substituted and/or terminated with one or more substituents selected from halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$, $SO_2R^{17}$;

$R^9$ and $R^{10}$ independently represent H, $C(O)R^6$, $SO_2R^{11}$, $C_1$–$C_6$ alkyl, Het, $C_1$–$C_6$ alkylHet, aryl or $C_1$–$C_6$ alkylaryl which latter five substituent groups are all optionally substituted and/or terminated with one or more substituents selected from halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$, $SO_2R^{17}$; or $R^9$ and $R^{10}$ together with the nitrogen atom to which they are bound can form a heterocyclic ring which is optionally substituted and/or terminated with one or more substituents selected from halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$, $SO_2R^{17}$;

$R^{11}$ represents $C_1$–$C_6$ alkyl, Het, $C_1$–$C_6$ alkylHet, aryl or $C_1$–$C_6$ alkylaryl which latter five substituent groups are all optionally substituted and/or terminated with one or more substituents selected from halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$, $SO_2R^{17}$;

$R^{12}$ represents H or $C_1$–$C_6$ alkyl;

$R^{13}$ and $R^{14}$ independently represent H or $C_1$–$C_6$ alkyl; or $R^{13}$ and $R^{14}$ together with the nitrogen atom to which they are bound can form a heterocyclic ring;

$R^{15}$ and $R^{16}$ independently represent H, $C(O)R^{12}$, $SO_2R^{17}$ or $C_1$–$C_6$ alkyl; or $R^{15}$ and $R^{16}$ together with the nitrogen atom to which they are bound can form a heterocyclic ring;

$R^{17}$ represents $C_1$–$C_6$ alkyl;

Het represents an optionally substituted four- to twelve-membered heterocyclic group, which group contains one or more heteroatoms selected from nitrogen, oxygen, sulfur and mixtures thereof wherein when $R^5$ is Het then said Het is C-linked to the sulphur atom of the $SO_2$ group in general formula I and with the proviso that $R^3$ does not represent H in formula IE where X is CH;

with the proviso that in formula 1A or 1 D when X is N, $R^5$ does not represent $C_1$–$C_6$ alkyl, optionally substituted and/or terminated with one or more substituents selected from halo, $OR^{17}$, $NR^{12}R^{17}$ or $NR^{17}C(O)R^{17}$.

The term "aryl", when used herein, represents $C_1$–$C_{11}$ aryl groups which include phenyl and naphthyl groups.

The term "Het", when used herein, includes four- to twelve-membered, preferably four- to ten-membered, ring systems, which rings contain one or more heteroatoms selected from nitrogen, oxygen, sulfur and mixtures thereof, and which rings may contain one or more double bonds or be non-aromatic, partly aromatic or wholly aromatic in character. The ring systems may be monocyclic, bicyclic or fused. The term thus includes groups such as optionally substituted azetidinyl, pyrrolidinyl, imidazolyl, indolyl, furanyl, oxazolyl, isoxazolyl, oxadiazolyl, thiazolyl, thiadiazolyl, triazolyl, tetrazolyl, oxatriazolyl, thiatriazolyl, pyridazinyl, morpholinyl, pyrimidinyl, pyrazinyl, pyridinyl, quinolinyl, isoquinolinyl, piperidinyl, pyrazolyl imidazopyridinyl and piperazinyl. Substitution at Het may be at a carbon atom of the Het ring or, where appropriate, at one or more of the heteroatoms.

"Het" groups may also be in the form of an N-oxide.

The heterocyclic ring that $R^7$ and $R^8$, $R^9$ and $R^{10}$, $R^{13}$ and $R^{14}$ or $R^{15}$ and $R^{16}$ (together with the nitrogen atom to which they are bound) may represent may be any heterocyclic ring that contains at least one nitrogen atom, and which ring forms a stable structure when attached to the remainder of the molecule via the essential nitrogen atom (which, for the avoidance of doubt, is the atom to which $R^7$ and $R^8$, $R^9$ and $R^{10}$, $R^{13}$ and $R^{14}$ or $R^{15}$ and $R^{16}$ are attached respectively). In this respect, heterocyclic rings that $R^7$ and $R^8$, $R^9$ and $R^{10}$, $R^{13}$ and $R^{14}$ or $R^{15}$ and $R^{16}$ (together with the nitrogen atom to which they are bound) may represent include four- to twelve-membered, preferably four- to ten-membered, ring systems, which rings contain at least one nitrogen atom and optionally contain one or more further heteroatoms selected from nitrogen, oxygen and sulfur, and which rings may contain one or more double bonds or be non-aromatic, partly aromatic or wholly aromatic in character. The term thus includes groups such as azetidinyl, pyrrolidinyl, imidazolyl, indolyl, triazolyl, tetrazolyl, morpholinyl, piperidinyl, pyrazolyl and piperazinyl.

The term "$C_1$–$C_6$ alkyl" (which includes the alkyl part of alkylHet and alkylaryl groups), when used herein, includes methyl, ethyl, propyl, butyl, pentyl and hexyl groups. Unless otherwise specified, alkyl groups may, when there is a sufficient number of carbon atoms, be linear or branched, be saturated or unsaturated or be cyclic, acyclic or part cyclic/acyclic. Preferred $C_1$–$C_6$ alkyl groups for use herein are $C_1$–$C_3$ alkyl groups. The term "$C_1$–$C_6$ alkylene", when used herein, includes $C_1$–$C_6$ groups which can be bonded at two places on the group and is otherwise defined in the same way as "$C_1$–$C_6$ alkyl". The term "acyl" includes C(O)—($C_1$–$C_6$) alkyl.

In the terms "$C_1$–$C_6$ alkylHet" and "$C_1$–$C_6$ alkylaryl", "Het" and "aryl" are as defined hereinbefore. Substituted $C_1$–$C_6$ alkylHet and $C_1$–$C_6$ alkylaryl may have substituents on the ring and/or on the alkyl chain.

Halo groups with which the above-mentioned groups may be substituted or terminated include fluoro, chloro, bromo and iodo.

The pharmaceutically or veterinarily acceptable salts of the compounds of the invention which contain a basic centre are, for example, non-toxic acid addition salts formed with inorganic acids such as hydrochloric, hydrobromic, hydroiodic, sulphuric and phosphoric acid, with carboxylic acids or with organo-sulphonic acids. Examples include the HCl, HBr, HI, sulphate or bisulphate, nitrate, phosphate or hydrogen phosphate, acetate, benzoate, succinate, saccarate, fumarate, maleate, lactate, citrate, tartrate, gluconate, camsylate, methanesulphonate, ethanesulphonate, benzenesulphonate, p-toluenesulphonate and pamoate salts. Compounds of the invention can also provide pharmaceutically or veterinarily acceptable metal salts, in particular non-toxic alkali and alkaline earth metal salts, with bases. Examples include the sodium, potassium, aluminium, calcium, magnesium, zinc and diethanolamine salts. For a review on suitable pharmaceutical salts see Berge et al, *J. Pharm. Sci.*, 1977, 66, 1–19.

The pharmaceutically acceptable solvates of the compounds of the invention include the hydrates thereof.

Also included within the scope of the compound and various salts of the invention are polymorphs thereof.

Compounds of formula I which contain one or more asymmetric carbon atoms exist in two or more stereoisomeric forms. Where a compound of formula I contains an alkenyl or alkenylene group, cis (E) and trans (Z) isomerism may also occur. The present invention includes the individual stereoisomers of the compounds of formula I and, where appropriate, the individual tautomeric forms thereof, together with mixtures thereof. Separation of diastereoisomers or cis and trans isomers may be achieved by conventional techniques, e.g. by fractional crystallisation, chromatography or H.P.L.C. of a stereoisomeric mixture of compounds of formula I or a suitable salt or derivative thereof. An individual enantiomer of a compound of formula I may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate.

All stereoisomers are included within the scope of the invention.

A preferred group of compounds according to a further aspect of the invention, are compounds of formulae IA, IB, IC, ID and IE as hereinbefore defined, wherein:

X represents CH or N;

$R^1$, $R^2$ and $R^3$, where present, independently represent $C_1$–$C_6$ alkyl, Het, $C_1$–$C_6$ alkylHet, aryl or $C_1$–$C_6$ alkylaryl optionally substituted and/or terminated with one or more substituents selected from halo, $OR^6$, $C(O)OR^6$ and $NR^9R^{10}$;

$R^4$ represents $C_1$–$C_6$ alkyl, Het, $C_1$–$C_6$ alkylHet, aryl or $C_1$–$C_6$ alkylaryl optionally substituted and/or terminated with one or more substituents selected from halo and $OR^6$;

$R^5$ represents $C_1$–$C_6$ alkyl, Het, $C_1$–$C_6$ alkylHet, aryl or $C_1$–$C_6$ alkylaryl (these groups are all optionally substituted and/or terminated with one or more substituents selected from halo, $OR^6$, $C(O)OR^6$ and $NR^9R^{10}$);

wherein $R^6$, $R^9$ and $R^{10}$ are as hereinbefore defined;

with the proviso that when $R^5$ is Het, said Het is C-linked to the sulphur atom of the $SO_2$ group in general formula I; and with the proviso that $R^3$ does not represent H in formula IE when X is CH; and with the proviso that in formula 1A or 1D when X is N, $R^5$ does not represent $C_1$–$C_6$ alkyl, optionally substituted and/or terminated with one or more substituents selected from halo, $OR^{17}$, $NR^{12}R^{17}$ or $NR^{17}C(O)R^{17}$.

A more preferred group of compounds according to a further aspect of the invention, are compounds of formulae IA, IB, and ID as hereinbefore defined, wherein:

X represents CH or N, and wherein X is preferably CH;

$R^1$, $R^2$ and $R^3$, where present, independently represent $C_1$–$C_6$ alkyl, Het or $C_1$–$C_6$ alkylHet optionally substituted and/or terminated with one or more substituents selected from $OR^6$, $C_1$–$C_6$ alkyl and $NR^9R^{10}$;

$R^4$ represents $C_1$–$C_6$ alkyl, $C_1$–$C_6$ alkylHet, optionally substituted and/or terminated with $OR^6$;

$R^5$ represents $C_1$–$C_6$ alkyl optionally substituted and/or terminated with one or more substituents selected from halo, $OR^6$, $C(O)OR^6$ and $NR^9R^{10}$;

wherein $R^6$, $R^9$ and $R^{10}$ are as hereinbefore defined with the proviso that in formula 1A or 1D when X is N, $R^5$ does not represent $C_1$–$C_6$ alkyl, optionally substituted and/or terminated with one or more substituents selected from halo, $OR^{17}$, $NR^{12}R^{17}$ or $NR^{17}C(O)R^{17}$.

A more preferred group of compounds herein are compounds of general formulae IA and ID which can be represented by the general formula IG:

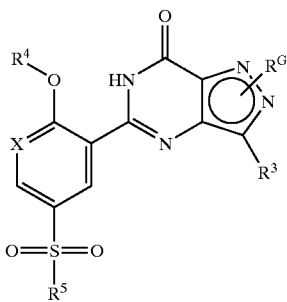

IG wherein general formula IG represents formula IA and ID depending upon whether $R^G$ is $R^1$ or $R^2$ as defined hereinbefore.

Thus according to a preferred aspect the present invention provides compounds of general formula IG wherein:

X represents CH or N, and wherein X is preferably CH;

$R^G$ is $R^1$ or $R^2$;

$R^1$, $R^2$ and $R^3$, where present, independently represent $C_1-C_6$ alkyl, Het or $C_1-C_6$ alkylHet optionally substituted and/or terminated with one or more substituents selected from $OR^6$, $C_1-C_6$ alkyl and $NR^9R^{10}$;

$R^4$ represents $C_1-C_6$ alkyl, $C_1-C_6$ alkylHet, optionally substituted and/or terminated with $OR^6$;

$R^5$ represents $C_1-C_6$ alkyl optionally substituted and/or terminated with one or more substituents selected from halo, $OR^6$, $C(O)OR^6$ and $NR^9R^{10}$;

wherein $R^6$, $R^9$ and $R^{10}$ are as hereinbefore defined
with the proviso that when X is N, $R^5$ does not represent $C_1-C_6$ alkyl, optionally substituted and/or terminated with one or more substituents selected from halo, $OR^{17}$, $NR^{12}R^{17}$ or $NR^{17}C(O)R^{17}$.

A preferred group of compounds of general formula IG include those wherein:

X represents CH;

$R^G$ is $R^1$ and represents $C_1-C_3$ alkyl or $C_1-C_3$ alkylHet wherein said $C_1-C_3$ alkyl group is optionally substituted with one or more substituents selected from halo, $OR^6$, $C(O)OR^6$ and $NR^9R^{10}$ and wherein said $C_1-C_3$ alkylHet group is optionally substituted and/or terminated with one or more substituents selected from halo, $C_1-C_6$ alkyl, $OR^6$, $C(O)OR^6$ and $NR^9R^{10}$;

$R^3$ represents $C_1-C_6$ alkyl optionally substituted and/or terminated with one or more substituents selected from halo and $OR^6$;

$R^4$ represents $C_1-C_6$ alkyl or $C_1-C_6$ alkylHet optionally substituted and/or terminated with one or more substituents selected from halo and $OR^6$;

$R^5$ represents $C_1-C_6$ alkyl optionally substituted and/or terminated with one or more substituents selected from halo and $OR^6$;

A further preferred group of compounds of general formula IG include those wherein:

X represents CH;

$R^G$ represents $R^1$ which represents methyl, ethyl or $C_1-C_3$ alkylHet wherein said $C_1-C_3$ alkylHet group is optionally substituted and/or terminated with one or more substituents selected from halo, $C_1-C_6$ alkyl, $OR^6$, $C(O)OR^6$ and $NR^9R^{10}$ and wherein $R^1$ is preferably $C_1-C_3$ alkylHet optionally substituted and/or terminated with one or more substituents selected from $C_1-C_6$ alkyl and $OR^6$ and wherein said Het group is a C-linked 5 or 6 membered saturated or unsaturated heterocyclic group containing at least one nitrogen atom and optionally including oxygen or sulphur atoms and wherein said Het is more preferably a C-linked 5 or 6-membered heterocyclic group containing one or two nitrogen atoms;

$R^3$ represents $C_2-C_4$ alkyl, and is preferably ethyl, n-propyl or iso-propyl and is most preferably ethyl;

$R^4$ represents $C_2-C_4$ alkyl optionally substituted and/or terminated with one or more substituents selected from halo and $OR^6$ and wherein when said is $C_2-C_4$ alkyl group is preferably propyl;

$R^5$ represents $C_1-C_4$ alkyl and wherein $R^5$ is preferably $C_1-C_3$ alkyl, more preferably methyl or ethyl, most preferably methyl;

wherein $R^6$, $R^9$ and $R^{10}$ are independently selected from methyl or ethyl groups.

An alternative preferred group of compounds herein are compounds of general formulae IG wherein:

X represents CH;

$R^G$ represents $R^2$ and is $C_1-C_6$ alkyl, Het or $C_1-C_3$ alkylHet wherein said $C_1-C_6$ alkyl, Het or $C_1-C_3$ alkylHet groups are optionally substituted and/or terminated with one or more substituents selected from halo, $C_1-C_6$ alkyl, $OR^6$, $C(O)OR^6$ and $NR^9R^{10}$ and wherein when $R^2$ represents $C_1-C_6$ alkyl, said alkyl group may be straight chain, branched chain or part or wholly cyclic;

$R^3$, $R^4$ and $R^5$ independently represent $C_1-C_6$ alkyl optionally substituted and/or terminated with one or more substituents selected from halo and $OR^6$;

An additional alternative preferred group of compounds of general formula IG include those wherein:

X represents CH;

$R^G$ represents $R^2$ and is $C_1-C_5$ alkyl, Het or alkylHet wherein the Het groups of said Het or alkyl Het is a C-linked Het group which is optionally substitued and/or terminated with one or more substituents selected from halo, $C_1-C_6$ alkyl, $OR^6$, $C(O)OR^6$ and $NR^9R^{10}$, wherein when $R^G$ is alkyl Het, then said alkylHet group is preferably a 5 or 6-membered saturated or unsaturated heterocyclic group containing at least one nitrogen atom and optionally including oxygen or sulphur atoms and is preferably a pyrrolidinyl or an imidazolyl group and wherein when $R^G$ is Het, then said Het group is a 4 or 5-membered heterocyclic group containing one or two nitrogen atoms and is preferably an azetidinyl group wherein the N can be optionally substituted as described hereinbefore and wherein when $R^G$ is $C_1-C_5$ alkyl said alkyl is preferably cyclopropylmethyl;

$R^3$ represents $C_2-C_4$ alkyl, and is preferably ethyl, n-propyl or iso-propyl and is most preferably ethyl;

$R^4$ represents $C_2-C_4$ alkyl and is preferably propyl or butyl $R^5$ represents $C_1-C_4$ alkyl and wherein $R^5$ is preferably $C_1-C_3$ alkyl and is more preferably methyl or ethyl, most preferably methyl;

wherein $R^6$, $R^9$ and $R^{10}$ are independently selected from methyl or ethyl groups.

An alternative additional groups of compounds preferred herein are compounds of general formula IG wherein:

X is CH;

when $R^G$ is $R^1$, $R^G$ represents $C_1$–$C_3$ alkyl or $R^G$ represents $C_1$–$C_6$ alkylHet, preferably $C_1$–$C_3$ pyridyl or pyrazolyl and wherein when $R^G$ is $R^1$ then $R^G$ is more preferably $C_1$–$C_3$ alkyl, most preferably methyl; or when $R^G$ is $R^2$, RG represents $C_1$–$C_6$ alkylHet, wherein said Het is C-linked and is preferably $C_1$–$C_3$ imidazolyl or pyrazolyl or $R^G$ represents Het wherein said Het is C-linked and is preferably an optionally N-substituted azetidinyl group or RG represents $C_1$–$C_5$ alkyl and is preferably cyclopropylmethyl or methoxyethyl and wherein when $R^G$ $R^1$ then $R^G$ is more preferably $C_1$–$C_3$ imidazolyl or $C_1$–$C_3$ pyrazolyl or cyclopropylmethyl;

$R^3$ is $C_1$–$C_6$ alkyl, preferably $C_1$–$C_4$ alkyl and more preferably ethyl or propyl;

$R^4$ is $C_1$–$C_6$ alkyl, preferably n-butyl, t-butyl, n-propyl, ethyl and more preferably ethyl when $R^G$ is $R^1$ and more preferably propyl or t-butyl when RG is $R^2$;

$R^5$ is $C_1$–$C_3$ alkyl and is preferably methyl.

Preferred compounds of general formulae IA, IB or ID herein include the following:

5-[2-Ethoxy-5-(methylsulfonyl)phenyl]-1-methyl-3-propyl-1,6-dihydro-7H-pyrazolo[4,3-d]pyrimidin-7-one;

5-[2-Butoxy-5-(methylsulfonyl)phenyl]-3-ethyl-2-(2-methoxyethyl)-2,6-dihydro-7H-pyrazolo[4,3-d]pyrimidin-7-one;

3-Ethyl-5-[2-isobutoxy-5-(methylsulfonyl)phenyl]-1-(2-pyridinylmethyl)-1,6-dihydro-7H-pyrazolo[4,3-d]pyrimidin-7-one;

5-[2-Butoxy-5-(methylsulfonyl)phenyl]-3-ethyl-1-(2-pyridinylmethyl)-1,6-dihydro-7H-pyrazolo[4,3-d]pyrimidin-7-one;

3-Ethyl-5-[2-isobutoxy-5-(methylsulfonyl)phenyl]-1-[(1-methyl-1H-imidazol-2-yl)methyl]-1,6-dihydro-7H-pyrazolo[4,3-d]pyrimidin-7-one;

5-[2-Butoxy-5-(methylsulfonyl)phenyl]-3-ethyl-2-[2-(4-morpholinyl)ethyl]-2,6-dihydro-7H-pyrazolo[4,3-d]pyrimidin-7-one;

3-Ethyl-5-[2-isobutoxy-5-(methylsulfonyl)phenyl]-2-[(1-methyl-1H-imidazol-2-yl)methyl]-2,6-dihydro-7H-pyrazolo[4,3-d]pyrimidin-7-one;

3-Ethyl-5-[2-isobutoxy-5-(methylsulfonyl)phenyl]-2-[2-(4-morpholinyl)ethyl]-2,6-dihydro-7H-pyrazolo[4,3-d]pyrimidin-7-one;

3-Ethyl-5-[5-(methylsulfonyl)-2-propoxyphenyl]-1-(2-pyridinylmethyl)-1,6-dihydro-7H-pyrazolo[4,3-d]pyrimidin-7-one;

2-(Cyclopropylmethyl)-3-ethyl-5-[5-(methylsulfonyl)-2-propoxyphenyl]-2,6-dihydro-7H-pyrazolo[4,3-d]pyrimidin-7-one;

3-Ethyl-5-[2-isobutoxy-5-(methylsulfonyl)phenyl]-1-{[(2S)-1-methylpyrrolidinyl]methyl}-1,6-dihydro-7H-pyrazolo[4,3-d]pyrimidin-7-one;

3-Ethyl-5-[2-isobutoxy-5-(methylsulfonyl)phenyl]-2-{[(2R)-1-methylpyrrolidinyl]methyl}-2,6-dihydro-7H-pyrazolo[4,3-d]pyrimidin-7-one;

3-Ethyl-5-[2-isobutoxy-5-(methylsulfonyl)phenyl]-2-(3-pyridazinylmethyl)-2,6-dihydro-7H-pyrazolo[4,3-d]pyrimidin-7-one;

3-Ethyl-5-[2-isobutoxy-5-(methylsulfonyl)phenyl]-1-(3-pyridazinylmethyl)-1,6-dihydro-7H-pyrazolo[4,3-d]pyrimidin-7-one;

3-Ethyl-5-[2-isobutoxy-5-(methylsulfonyl)phenyl]-2-(2-pyridinylmethyl)-2,6-dihydro-7H-pyrazolo[4,3-d]pyrimidin-7-one;

3-Ethyl-1-{[(2S)-1-methylpyrrolidinyl]methyl}-5-[5-(methylsulfonyl)-2-propoxyphenyl]-1,6-dihydro-7H-pyrazolo[4,3-d]pyrimidin-7-one;

5-[2-Butoxy-5-(methylsulfonyl)phenyl]-3-ethyl-2-(1-isopropyl-3-azetidinyl)-2,6-dihydro-7H-pyrazolo[4,3-d]pyrimidin-7-one;

3-Ethyl-5-[2-isobutoxy-5-(methylsulfonyl)phenyl]-1-(1-isopropyl-3-azetidinyl)-1,6-dihydro-7H-pyrazolo[4,3-d]pyrimidin-7-one;

3-Ethyl-5-[2-isobutoxy-5-(methylsulfonyl)phenyl]-2-(1-methyl-4-piperidinyl)-2,6-dihydro-7H-pyrazolo[4,3-d]pyrimidin-7-one;

3-Ethyl-5-[2-isobutoxy-5-(methylsulfonyl)phenyl]-2-(1-isopropyl-4-piperidinyl)-2,6-dihydro-7H-pyrazolo[4,3-d]pyrimidin-7-one;

1-[2-(Diisopropylamino)ethyl]-3-ethyl-5-[5-(methylsulfonyl)-2-propoxyphenyl]-1,6-dihydro-7H-pyrazolo[4,3-d]pyrimidin-7-one;

2-[2-(Diisopropylamino)ethyl]-3-ethyl-5-[5-(methylsulfonyl)-2-propoxyphenyl]-2,6-dihydro-7H-pyrazolo[4,3-d]pyrimidin-7-one;

3-Ethyl-5-[5-(ethylsulfonyl)-2-propoxyphenyl]-1-{[(2S)-1-methylpyrrolidinyl]methyl}-1,6-dihydro-7H-pyrazolo[4,3-d]pyrimidin-7-one;

3-Ethyl-1-{[(2S)-1-methylpiperidinyl]methyl}-5-[5-(methylsulfonyl)-2-propoxyphenyl]-1,6-dihydro-7H-pyrazolo[4,3-d]pyrimidin-7-one or 5-Allyl-2-[2-butoxy-5-(methylsulfonyl)phenyl]-7-ethylimidazo[5,1-f][1,2,4]triazin-4(3H)-one.

and pharmaceutically acceptable salts, solvates, pro-drugs or polymorphs thereof.

Also included within the scope of the invention are radiolabelled derivatives of compounds of formulae I, IA, IB, IC, ID and IE which are suitable for biological studies.

The present invention additionally provides compounds of general formula I:

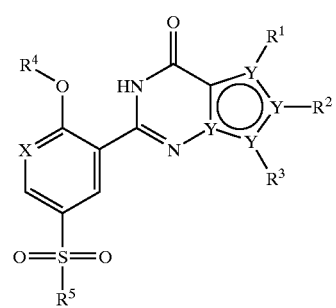

or a pharmaceutically or veterinarily acceptable salt and/or solvate, polymorph or pro-drug thereof, wherein Y represents C or N, with N being in at least one, but not more than two, of the positions marked by Y;

X represents CH or N;

$R^1$, $R^2$ and $R^3$ where present and attached to nitrogen independently represent H, $C_1$–$C_6$ alkyl, Het, $C_1$–$C_6$ alkylHet, aryl or $C_1$–$C_6$ alkylaryl;

$R^1$, $R^2$ and $R^3$ where present and attached to carbon independently represent H, halo, cyano, nitro, $OR^6$, $OC(O)R^6$, $C(O)R^6$, $C(O)OR^6$, $NR^6C(O)NR^7R^8$, $NR^6C$ (O)OR$^6$, OC(O)NR$^7$R$^8$, C(O)NR$^9$R$^{10}$, NR$^9$R$^{10}$, SO$_2$NR$^9$R$^{10}$, SO$_2$R$^{11}$, C$_1$–C$_6$ alkyl, Het, C$_1$–C$_6$ alkylHet, aryl or C$_1$–C$_6$ alkylaryl;

wherein when R$^1$ and R$^2$ are present they may optionally be connected via a C—C, C—N or C—O bond;

wherein when R$^2$ and R$^3$ are present they may optionally be connected via a C—C, C—N or C—O bond;

R$^4$ represents H, C$_1$–C$_6$ alkyl, Het, C$_1$–C$_6$ alkylHet, aryl or C$_1$–C$_6$ alkylaryl;

R$^5$ represents represent C$_1$–C$_6$ alkyl, Het, C$_1$–C$_6$ alkylHet, aryl or C$_1$–C$_6$ alkylaryl;

wherein when R$^1$, R$^2$ and R$^3$, where present, or R$^4$ or R$^5$ is a C$_1$–C$_6$ alkyl, Het, C$_1$–C$_6$ alkylHet, aryl and C$_1$–C$_6$ alkylaryl group, such C$_1$–C$_6$ alkyl, Het, C$_1$–C$_6$ alkylHet, aryl and C$_1$–C$_6$ alkylaryl group is optionally substituted and/or terminated with one or more substituents selected from halo, cyano, nitro, OR$^6$, OC(O)R$^6$, C(O)R$^6$, C(O)OR$^6$, NR$^6$C(O)N R$^7$R$^8$, NR$^6$C(O)OR$^6$, OC(O)NR$^7$R$^8$, C(O)NR$^9$R$^{10}$, NR$^9$R$^{10}$, SO$_2$NR$^9$R$^{10}$, SO$_2$R$^{11}$, C$_1$–C$_6$ alkyl, Het, C$_1$–C$_6$ alkylHet, aryl or C$_1$–C$_6$ alkylaryl which latter five substituent groups are all optionally substituted and/or terminated with one or more substituents selected from halo, cyano, nitro, OR$^{12}$, OC(O)R$^{12}$, C(O)R$^{12}$, C(O)OR$^{12}$, NR$^{12}$C(O)NR$^{13}$R$^{14}$, NR$^{12}$C(O)OR$^{12}$, OC(O)NR$^{13}$R$^{14}$, C(O)NR$^{15}$R$^{16}$, NR$^{15}$R$^{16}$, SO$_2$NR$^{15}$R$^{16}$, SO$_2$R$^{17}$;

R$^6$ represents H, C$_1$–C$_6$ alkyl, Het, C$_1$–C$_6$ alkylHet, aryl or C$_1$–C$_6$ alkylaryl which latter five substituent groups are all optionally substituted and/or terminated with one or more substituents selected from halo, cyano, nitro, OR$^{12}$, OC(O)R$^{12}$, C(O)R$^{12}$, C(O)OR$^{12}$, NR$^{12}$C(O)NR$^{13}$R$^{14}$, NR$^{12}$C(O)OR$^{12}$, OC(O)NR$^{13}$R$^{14}$, C(O)NR$^{15}$R$^{16}$, NR$^{15}$R$^{16}$, SO$_2$NR$^{15}$R$^{16}$, SO$_2$R$^{17}$;

R$^7$ and R$^8$ independently represent H, C$_1$–C$_6$ alkyl, Het, C$_1$–C$_6$ alkylHet, aryl or C$_1$–C$_6$ alkylaryl which latter five substituent groups are all optionally substituted and/or terminated with one or more substituents selected from halo, cyano, nitro, OR$^{12}$, OC(O)R$^{12}$, C(O)R$^{12}$, C(O)OR$^{12}$, NR$^{12}$C(O)NR$^{13}$R$^{14}$, NR$^{12}$ C(O)OR$^{12}$, OC(O)NR$^{13}$R$^{14}$, C(O)NR$^{15}$R$^{16}$, NR$^{15}$R$^{16}$, SO$_2$NR$^{15}$R$^{16}$, SO$_2$R$^{17}$; or R$^7$ and R$^8$ together with the nitrogen atom to which they are bound can form a heterocyclic ring which is optionally substituted and/or terminated with one or more substituents selected from halo, cyano, nitro, OR$^{12}$, OC(O)R$^{12}$, C(O)R$^{12}$, C(O)OR$^{12}$, NR$^{12}$C(O)NR$^{13}$R$^{14}$, NR$^{12}$C(O)OR$^{12}$, OC(O)NR$^{13}$R$^{14}$, C(O)NR$^{15}$R$^{16}$, NR$^{15}$R$^{16}$, SO$_2$NR$^{15}$R$^{16}$, SO$_2$R$^{17}$;

R$^9$ and R$^{10}$ independently represent H, C(O)R$^6$, SO$_2$R$^{11}$, C$_1$–C$_6$ alkyl, Het, C$_1$–C$_6$ alkylHet, aryl or C$_1$–C$_6$ alkylaryl which latter five substituent groups are all optionally substituted and/or terminated with one or more substituents selected from halo, cyano, nitro, OR$^{12}$, OC(O)R$^{12}$, C(O)R$^{12}$, C(O)OR$^{12}$, NR$^{12}$C(O) NR$^{13}$R$^{14}$, NR$^{12}$C(O)OR$^{12}$, OC(O)NR$^{13}$R$^{14}$, C(O)NR$^{15}$ R$^6$, NR$^{15}$ R$^{16}$, SO$_2$NR$^{15}$R$^{16}$, SO$_2$R$^{17}$; or R$^9$ and R$^{10}$ together with the nitrogen atom to which they are bound can form a heterocyclic ring which is optionally substituted and/or terminated with one or more substituents selected from halo, cyano, nitro, OR$^{12}$, OC(O)R$^{12}$, C(O)R$^{12}$, C(O)OR$^{12}$, NR$^{12}$C(O)NR$^{13}$R$^{14}$, NR$^{12}$C(O)OR$^{12}$, OC(O)NR$^{13}$R$^{14}$, C(O)NR$^{15}$R$^{16}$, NR$^{15}$R$^{16}$, SO$_2$NR$^{15}$R$^{16}$, SO$_2$R$^{17}$;

R$^{11}$ represents C$_1$–C$_6$ alkyl, Het, C$_1$–C$_6$ alkylHet, aryl or C$_1$–C$_6$ alkylaryl which latter five substituent groups are all optionally substituted and/or terminated with one or more substituents selected from halo, cyano, nitro, OR$^{12}$, OC(O)R$^{12}$, C(O)R$^{12}$, C(O)OR$^{12}$, NR$^{12}$C(O) NR$^{13}$R$^{14}$, NR$^{12}$C(O)OR$^{12}$, OC(O)NR$^{13}$R$^{14}$, C(O) NR$^{15}$R$^{16}$, NR$^{15}$R$^{16}$, SO$_2$NR$^{15}$R$^{16}$, SO$_2$R$^{17}$;

R$^{12}$ represents H or C$_1$–C$_6$ alkyl;

R$^{13}$ and R$^{14}$ independently represent H or C$_1$–C$_6$ alkyl; or

R$^{13}$ and R$^{14}$ together with the nitrogen atom to which they are bound can form a heterocyclic ring;

R$^{15}$ and R$^{16}$ independently represent H, C(O)R$^{12}$, SO$_2$R$^{17}$ or C$_1$–C$_6$ alkyl; or R$^{15}$ and R$^{16}$ together with the nitrogen atom to which they are bound can form a heterocyclic ring;

R$^{17}$ represents C$_1$–C$_6$ alkyl;

Het represents an optionally substituted four- to twelve-membered heterocyclic group, which group contains one or more heteroatoms selected from nitrogen, oxygen, sulfur and mixtures thereof.

Preparation

According to a further aspect of the invention there is provided processes for the preparation of compounds of the invention, as illustrated below.

The following processes are illustrative of the general synthetic procedures which may be adopted in order to obtain the compounds of the invention:

1. Compounds of formulae IA, IC, ID and IE may be prepared by cyclisation of corresponding compounds of formulae IIA, IIC, IID and IIE, respectively:

IIA
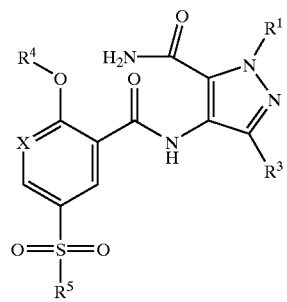

IIC
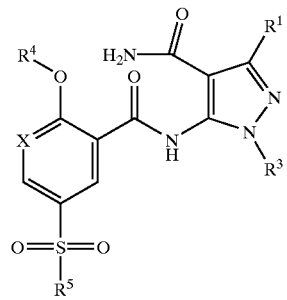

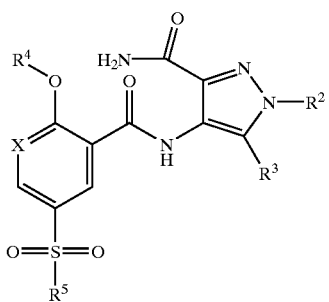

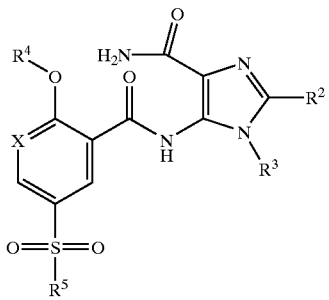

wherein $R^1$, $R^2$, $R^3$, $R^4$, $R^5$ and X are as defined previously for compounds of formulae IA, IC, ID and IE.

This cyclisation may be accomplished under basic, neutral or acidic conditions using known methods for pyrimidone ring formation. Preferably, the cyclisation is performed under basic conditions using an alkali metal salt of an alcohol or amine, such as sodium ethoxide, potassium tert-butoxide, cesium carbonate or potassium bis(trimethylsilyl)amide, in the presence of a suitable alcohol as solvent, for example at reflux temperature (or, if performed in a sealed vessel, at greater than reflux temperature). The skilled person will appreciate that, when an alcohol is selected as solvent, an appropriate alcohol of formula $R^4OH$ may be used if it is intended to mitigate alkoxide exchange at the 2-position of either the pyridin-3-yl or phenyl substituent. Conversely, a sterically hindered alcohol (e.g. 3-methyl-3-pentanol) may be used to avoid exchange at the 2-position of either the pyridin-3-yl or phenyl substituent. Optionally, an equivalent of an additive (e.g. $R^4OAc$) may be added to act as a hydroxide scavenger.

Compounds of formulae IIA, IIC, IID and IIE may be prepared by reaction of corresponding compounds of formulae IIIA, IIIC, IIID and IIIE, respectively:

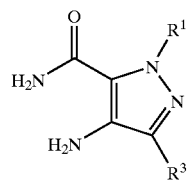

IIIA

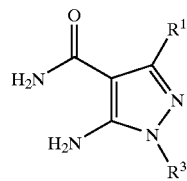

IIIC

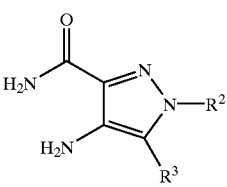

IID

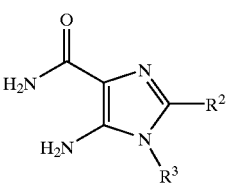

IIE

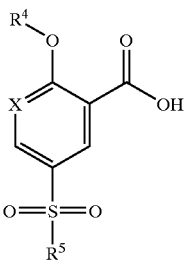

IIID

IIIE wherein $R^1$, $R^2$ and $R^3$ are as defined previously for compounds of formulae IIA, IIC, IID and IIE, with a compound of formula IV or a carboxylic acid derivative thereof:

IV wherein $R^4$, $R^5$ and X are as defined previously for compounds of formulae IIA, IIC, IID and IIE.

This coupling reaction may be achieved by conventional amide bond forming techniques which are well known to those skilled in the art. For example, an acyl halide (e.g. chloride) derivative of a compound of formula IV may be reacted with a compound of formula IIIA, IIIC, IIID or IIIE in the presence of an excess of a tertiary amine, such as triethylamine or pyridine, optionally in the presence of a suitable catalyst, such as 4-dimethylaminopyridine, in a suitable solvent such as dichloromethane or THF, at a temperature of about 0° C. to room temperature.

A variety of other amino acid coupling methodologies may be used to couple the compounds of formulae IIIA, IIIC, IIID or IIIE with the compound of formula IV. For example, the acid of formula IV or a suitable salt thereof (e.g. sodium salt) may be activated with an appropriate activating reagent, e.g. a carbodiimide, such as 1,3-dicyclohexylcarbodiimide or 1-(3-dimethylaminopropyl)-3-ethylcarbodiimide hydrochloride optionally in the presence of 1-hydroxybenzotriazole hydrate and/or a catalyst such as 4-dimethylaminopyridine; a halotrisaminophosphonium salt such as bromo-tris(pyrrolidinyl)phosphonium hexafluorophosphate; a suitable pyridinium salt such as 2-chloro-1-methyl pyridinium chloride; or another suitable coupling agent such as O-(7-azabenzotriazol-1-yl)-N,N,N',N'-tetramethyl-uronium hexafluorophosphate (HATU). Either type of coupling reaction may be conducted in a suitable solvent such as dichloromethane, tetrahydrofuran or N,N-dimethylformamide, optionally in the presence of a tertiary amine such as N-methylmorpholine or N-ethyldiisopropylamine (for example when either the compound of formula IIIA, IIIC, IIID or IIIE, or the activating agent is presented in the form of an acid addition salt), at from about 0° C. to about room temperature. Preferably, from about 1 to 2 molecular equivalents of the activating reagent and from 1 to 3 molecular equivalents of any tertiary amine present may be employed.

Alternatively, the carboxylic acid function of IV may be activated using an excess of a reagent such as N,N'-carbonyldiimidazole in an appropriate solvent, e.g. ethyl acetate, dichloromethane or butan-2-one, at from about room temperature to about 80° C., followed by reaction of the intermediate imidazolide with either a compound of the formula IIIA, IIIC, IIID or IIIE at from about 20° C. to about 90° C.

In a further variation, a compound of formula IA, IC, ID or IE, as defined previously, may be formed in a one-pot procedure by coupling a compound of formula IIA, IIIC, IIID or IIIE with the acyl chloride or a lower alkyl ester derivative of formula IV and by cyclising the resultant intermediate compound of formula IIA, IIC, IID or IIE, using the methods as described previously. When using an acyl chloride derivative of formula IV, a suitable solvent (e.g. pyridine) may serve as both an acid scavenger and as the solvent for the in-situ coupling and cyclisation reaction.

Compounds of formula IV, where X is CH and $R^5$ is Me, may be prepared from compounds of formula V:

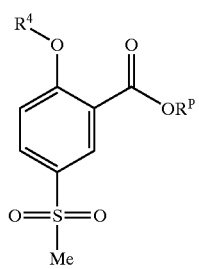

V wherein $R^4$ is as defined previously for compounds of formula IV, and $R^P$ is a protecting group for a carboxylic acid (preferably a lower alkyl group such as methyl, ethyl or t-butyl), by using standard methods for deprotection.

Compounds of formula V may be prepared by the alkylation of compounds of formula VI:

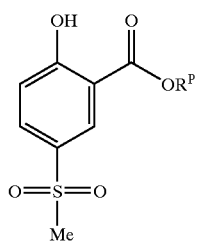

VI wherein $R^P$ is as defined previously for compounds of formula V, by reaction with a compound of formula $R^4$-L, wherein $R^4$ is as defined previously for compounds of formula V, and L is a leaving group, such as halo, preferably chloro, bromo or iodo, for example at between room and reflux temperature in a suitable solvent (e.g. acetonitrile) in the presence of a suitable base (e.g. cesium carbonate).

Compounds of formula VI may be prepared from compound VII using standard conditions for protecting carboxylic acids.

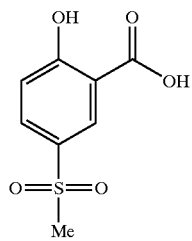

VII

Alternatively, compounds of formula IV may be prepared from compounds of formula VIII:

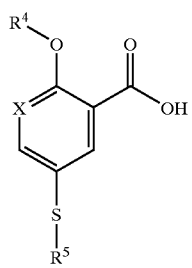

VIII wherein $R^4$, $R^5$ and X are as defined previously for compounds of formula IV, by reaction with an oxidant (e.g. meta chloroperbenzoic acid (mCPBA)), for example at between 0° C. and room temperature in a suitable solvent (e.g. dichloromethane).

Compounds of formula VII may be prepared from compounds of formula IX by first forming an intermediate diazonium salt, for example by the action of sodium nitrite in a mixture of concentrated hydrochloric acid and glacial acetic acid at from about −25° C. to about 0° C., followed by reaction with $R^5SSR^5$ and a copper salt, preferably $CuBr_2$, for example at between 0° C. and room temperature:

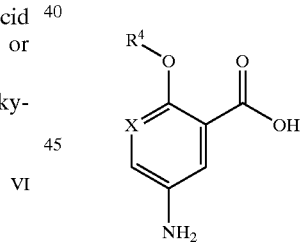

IX wherein $R^4$, $R^5$ and X are as defined previously for compounds of formula VIII.

Compounds of formula IX may be prepared by reducing compounds of formula X:

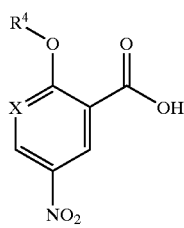

X wherein $R^4$ and X are as defined previously for compounds of formula IX, for example with hydrogen at 60 psi in a suitable solvent (e.g. $R^4OH$) at between room temperature and 60° C. in the presence of an appropriate catalyst (e.g. 10% palladium on carbon).

Alternatively, compounds of formula VIII may be prepared from compounds of formula XI:

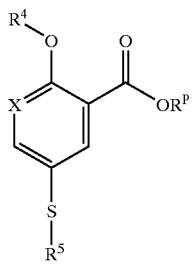

XI wherein $R^4$, $R^5$ and X are as defined previously for compounds of formula VII, and $R^P$ is a protecting group for a carboxylic acid (preferably a lower alkyl group such as methyl, ethyl or t-butyl), by using standard methods for deprotection.

Compounds of formula XI may be prepared from compounds of formula XII:

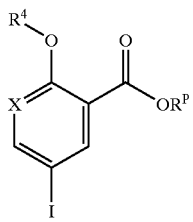

XII wherein $R^4$, X and $R^P$ are as defined previously for compounds of formula XI, by reaction with thiourea (1.1 equivalents) and a nickel (0) catalyst, generated in situ from bis(triethylphosphine)nickel(II) chloride (0.05 equivalents) and sodium cyanoborohydride (0.075 equivalents), in a suitable solvent (e.g. N,N-dimethylformamide) at between room temperature and 80° C., followed by addition of $R^5$-L (wherein $R^5$ is as defined previously for compounds of formula XI and L is a leaving group such as halo, preferably chloro, bromo or iodo) and a suitable base (e.g. calcium oxide).

Compounds of formula XII, where X is N, may be prepared from compounds of formula XIII:

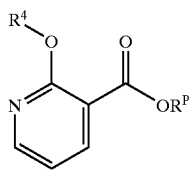

XIII wherein $R^4$ and $R^P$ are as defined previously for compounds of formula XII, by reaction with N-iodosuccinimide (1 to 2 equivalents) in a 4:1 mixture of trifluoroacetic acid and trifluoroacetic anhydride at between room and reflux temperature.

Alternatively, compounds of formula IV may be prepared from compounds of formula XIV:

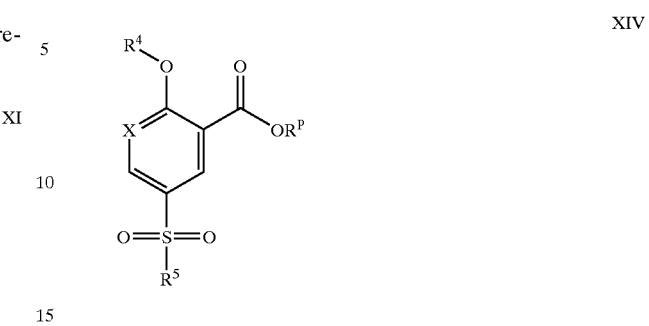

XIV wherein $R^4$, $R^5$ and X are as defined previously for compounds of formula IV, and $R^P$ is a protecting group for a carboxylic acid (preferably a lower alkyl group such as methyl, ethyl or t-butyl), by using standard methods for deprotection.

Compounds of formula XIV may be prepared from compounds of formula XV:

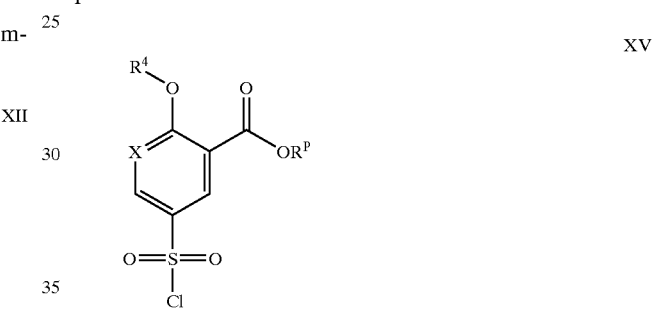

XV wherein $R^4$, X and $R^P$ are as defined previously for compounds of formula XIV, by reaction with sodium sulphite (2 equivalents) and sodium bicarbonate (2 equivalents) in water at room temperature, followed by reaction with sodium carbonate (2 equivalents) and $R^5$-L (wherein $R^5$ is as defined previously for compounds of formula XIV and L is a leaving group such as halo, preferably chloro, bromo or iodo) in aqueous alcohol (preferably $R^4OH$) at between room and reflux temperature.

2. Compounds of formulae IA, IC, ID and IE, where X is CH, may alternatively be prepared by deprotecting corresponding compounds of formulae XVIA, XVIC, XVID and XVIE respectively:

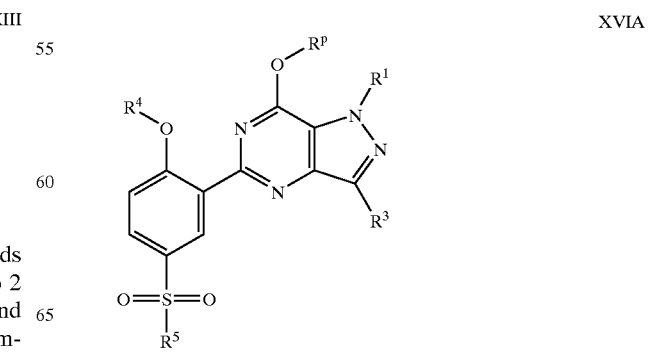

XVIA

XVIC
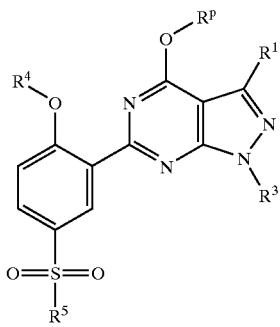

XVID
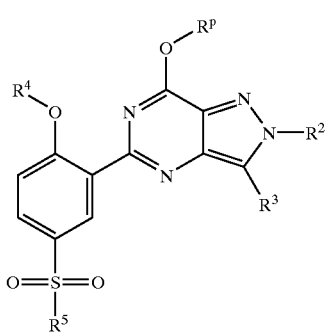

XVIE
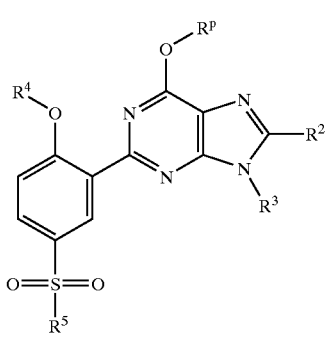

wherein $R^1$, $R^2$, $R^3$, $R^4$ and $R^5$ are as defined previously for compounds of formulae IA, IC, ID and IE, and $R^P$ is a protecting group (e.g. methyl), for example by reaction with 6M HCl at between room temperature and 70° C.

Compounds of formulae XVIA, XVIC, XVID and XVIE may be prepared by alkylating corresponding compounds of formulae XVIIA, XVIIC, XVIID and XVIIE (the skilled person will appreciate that XVIIA and XVIID are different tautomeric forms of the same compound) respectively:

XVIIA
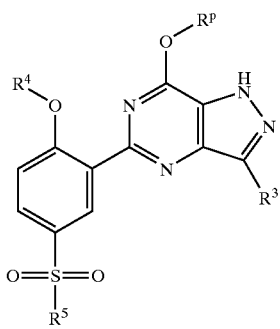

XVIIC
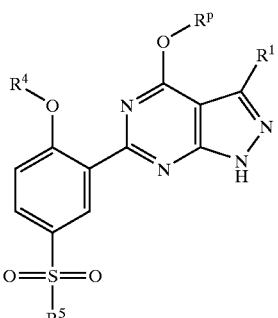

XVIID
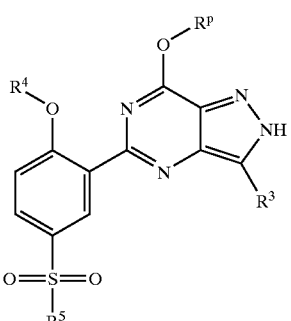

XVIIE
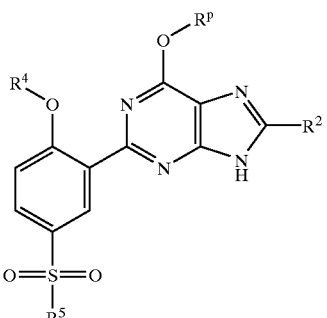

wherein $R^1$, $R^2$, $R^3$, $R^4$, $R^5$ and $R^P$ are as defined previously for compounds of formulae XVIA, XVIC, XVID and XVIE, by reaction with compounds of formulae $R^1$-L, $R^3$-L, $R^2$-L and $R^3$-L respectively, wherein $R^1$, $R^2$ and $R^3$ are as defined previously for compounds of formulae XVIA, XVIC, XVID and XVIE, and L is a leaving group, such as halo, preferably chloro, bromo or iodo, or an alkyl or aryl sulphonate, preferably methane sulphonate or p-toluene sulphonate, for example at between room and reflux temperature in a suitable solvent (e.g. N,N-dimethylformamide) in the presence of a suitable base (e.g. potassium carbonate).

Compounds of formulae XVIIA, XVIIC, XVIID and XVIIE may be prepared by reacting corresponding compounds of formulae XVIIIA, XVIIIC, XVIIID and XVIIIE (the skilled person will appreciate that XVIIIA and XVIIID are different tautomeric forms of the same compound) respectively:

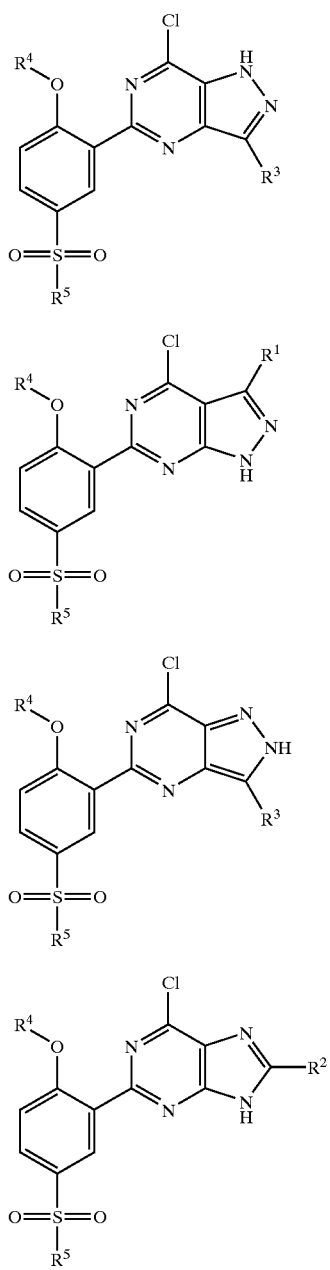

XVIIIA

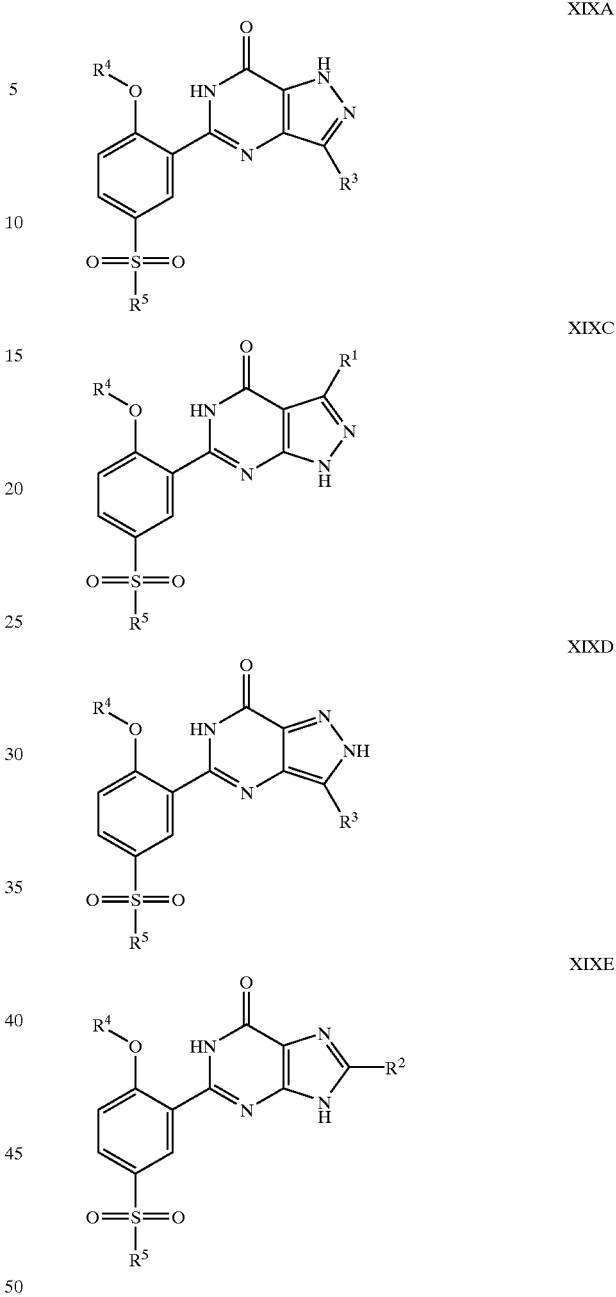

XIXA

XVIIIC

XIXC

XVIIID

XIXD

XVIIIE

XIXE wherein $R^1$, $R^2$, $R^3$, $R^4$ and $R^5$ are as defined previously for compounds of formulae XVIIA, XVIIC, XVIID and XVIIE, with $R^P$-OH, wherein $R^P$ is as defined previously for compounds of formulae XVIIA, XVIIC, XVIID and XVIIE, for example at between room and reflux temperature in the presence of a suitable base (e.g. potassium tert-butoxide).

Compounds of formulae XVIIIA, XVIIIC, XVIIID and XVIIIE may be prepared by reacting corresponding compounds of formulae XIXA, XIXC, XIXD and XIXE (the skilled person will appreciate that XIXA and XIXD are different tautomeric forms of the same compound) respectively:

wherein $R^1$, R $R^3$, $R^4$ and $R^5$ are as defined previously for compounds of formulae XVIIIA, XVIIIC, XVIIID and XVIIIE, with a chlorinating agent (e.g. POCl$_3$) at between room and reflux temperature, optionally in a suitable solvent and optionally in the presence of 1 to 2 equivalents of an additive (e.g. N,N-dimethylformamide or N,N-dimethylaniline). The skilled person will recognise that although the above structures have been given discreet formulae descriptors (XIXA, XIXC, XIXD and XIXE) for clarity, they are in fact a subset of formulae IA, IC, ID and IE wherein $R^1$, $R^3$, $R^2$ and $R^3$ are hydrogen respectively.

Compounds of formulae XIXA, XIXC, XIXD and XIXE may be prepared by cyclisation of corresponding compounds of formulae XXA, XXC, XXD and XXE (the skilled person will appreciate that XXA and XXD are different tautomeric forms of the same compound) respectively:

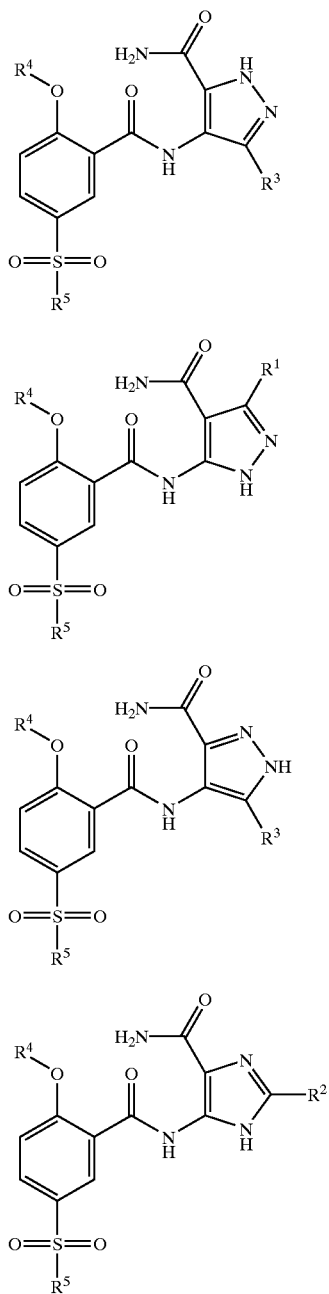

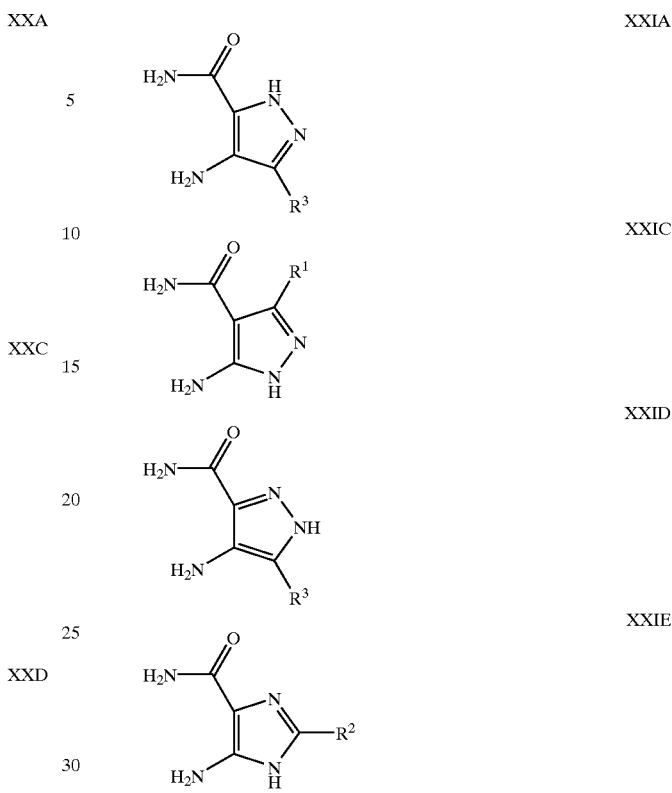

wherein $R^1$, $R^2$, $R^3$, $R^4$ and $R^5$ are as defined previously for compounds of formulae XIXA, XIXC, XIXD and XIXE, using the same conditions described for the preparation of IA, IC, ID and IE in process 1. The skilled person will recognise that although the above structures have been given discreet formulae descriptors (XXA, XXC, XXD and XXE) for clarity, they are in fact a subset of formulae IIA, IIC, IID and IIE wherein $R^1$, $R^3$, $R^2$ and $R^3$ are hydrogen respectively.

Compounds of formulae XXA, XXC, XXD and XXE may be prepared by reaction of corresponding compounds of formulae XXIA, XXIC, XXID and XXIE respectively:

wherein $R^1$, $R^2$ and $R^3$ are as defined previously for compounds of formulae XXA, XXC, XXD and XXE, with a compound of formula IV or a carboxylic acid derivative thereof, using the same conditions described for the preparation of IIA, IIC, IID and IIE in process 1. The skilled person will recognise that although the above structures have been given discreet formulae descriptors (XXIA, XXIC, XXID and XXIE) for clarity, they are in fact a subset of formulae IIIA, IIIC, IIID and IIIE wherein $R^1$, $R^3$, $R^2$ and $R^3$ are hydrogen respectively.

3. Compounds of formulae IIA, IIC, IID and IIE, in which $R^1$, $R^2$ and $R^3$, when attached to nitrogen, do not represent hydrogen, may alternatively be prepared by reacting corresponding compounds of formulae XXA, XXC, XXD and XXE (the skilled person will appreciate that XXA and XXD are different tautomeric forms of the same compound), with compounds of formulae $R^1$-L, $R^3$-L, $R^2$-L and $R^3$-L respectively, wherein $R^1$, $R^2$ and $R^3$ are as defined previously for compounds of formulae IIA, IIC, IID and IIE, and L is a leaving group, such as halo, preferably chloro, bromo or iodo, or an alkyl or aryl sulphonate, preferably methane sulphonate or p-toluene sulphonate, for example at between room and reflux temperature in a suitable solvent (e.g. N,N-dimethylformamide) in the presence of a suitable base (e.g. cesium carbonate).

4. Compounds of formulae IA, IC, ID and IE, in which $R^1$, $R^2$ and $R^3$, when attached to nitrogen, do not represent hydrogen, may alternatively be prepared by reacting corresponding compounds of formulae XIXA, XIXC, XIXD and XIXE (the skilled person will appreciate that XIXA and XIXD are different tautomeric forms of the same compound), with compounds of formulae $R^1$-L, $R^3$-L, $R^2$-L and $R^3$-L respectively, wherein $R^1$, $R^2$ and $R^3$ are as defined previously for compounds of formulae IA, IC, ID and IE, and L is a leaving group, such as halo, preferably chloro, bromo or iodo, or an alkyl or aryl sulphonate, preferably methane sulphonate or p-toluene sulphonate, for example at between room and reflux temperature in a suitable solvent (e.g. N,N-dimethylformamide) in the presence of a suitable base (e.g. cesium carbonate).

5. Compounds of formulae IA, IC, ID and IE, in which $R^1$, $R^2$ and $R^3$, when attached to carbon, represent either cyano, $C(O)R^6$, $C(O)OR^6$, $C(O)NR^9R^{10}$, $C_1$–$C_6$ alkyl, Het, $C_1$–$C_6$ alkylHet, aryl or $C_1$–$C_6$ alkylaryl (which latter five groups are all optionally substituted and/or terminated as detailed in the definition of $R^1$, $R^2$ and $R^3$) may alternatively be prepared by reacting corresponding compounds of formulae XXIIA, XXIIC, XXIID and XXIIE respectively:

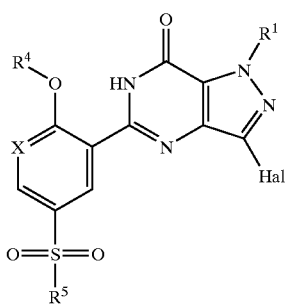

XXIIA

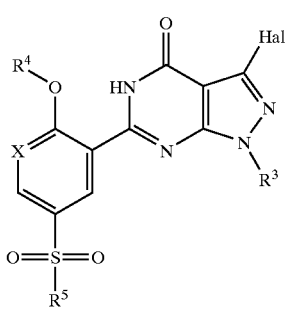

XXIIC

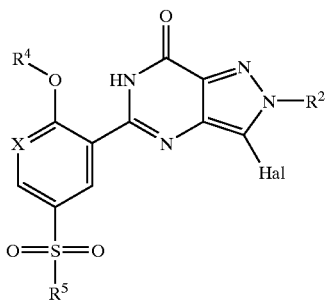

XXIID

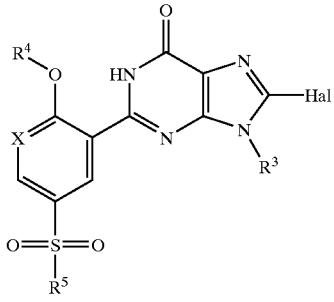

XXIIE wherein X, $R^4$, $R^5$, $R^6$, $R^9$ and $R^{10}$ are as defined previously for compounds of formulae IA, IC, ID and IE, and Hal represents Cl, Br or I (preferably Br or I), with $R^3$-FG, $R^1$-FG, $R^3$-FG and $R^2$-FG respectively, wherein $R^1$, $R^2$ and $R^3$ are as defined previously for compounds of formulae IA, IC, ID and IE, and FG represents the appropriate functional group (obvious to those skilled in the art) required to utilise the following coupling conditions:

(a) so-called "Suzuki" conditions (e.g. 1.2 equivalents of a boronic acid, 2 equivalents of $K_2CO_3$ and 0.1 equivalents of $Pd(PPh_3)_4$, at reflux temperature in a 4:1 mixture of dioxane and water);

(b) so-called "Stille" conditions (e.g. 1.5 equivalents of a stannane, 10 equivalents of LiCl, 0.15 equivalents of CuI, and 0.1 equivalents of $Pd(PPh_3)_4$, at reflux temperature in dioxane);

(c) so-called "Heck" conditions (e.g. 2 equivalents of an alkene [such as butyl vinyl ether to prepare $C(O)R^8$ containing compounds], 1.7 equivalents of $Et_3N$ and catalytic amounts of $Pd(OAc)_2$ and $P(o\text{-}tol)_3$, in MeCN at between room and reflux temperature);

(d) so-called "Sonogashira" conditions (e.g. 1.5 to 5 equivalents of a terminal alkyne and 0.03 equivalents of $Pd(PPh_3)_2Cl_2/CuI$, in $Et_3N$ and MeCN at between room temperature and 60° C. [alternatively followed by hydrolysis conditions (e.g. 0.3 equivalents $HgSO_4$, $H_2SO_4$ in acetone at reflux temperature) to prepare $C(O)R^8$ containing compounds]).

(e) Carbonylation conditions (e.g. palladium(II) acetate combined with 1,2-bis(diphenylphosphino)-propane (DPPP) under an atmosphere of carbon monoxide (e.g. at a pressure of around 70 psi) in the presence of an excess of a nucleophile (e.g. alcohol or amine), an excess of a tertiary amine base (e.g. $Et_3N$), and optionally in the presence of a suitable solvent (e.g. dimethylsulfoxide).

The skilled person will recognise that although the above structures have been given discreet formulae descriptors (XXIIA, XXIIC, XXIID and XXIIE) for clarity, they are in fact a subset of formulae IA, IC, ID and IE wherein $R^3$, $R^1$, $R^3$ and $R^2$ are Hal respectively.

Compounds of formulae XXIIA, XXIIC, XXIID and XXIIE may be prepared by reaction of corresponding compounds of formulae XXIIIA, XXIIIC, XXIIID and XXIIIE respectively:

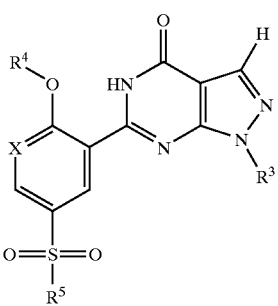

XXIIIA

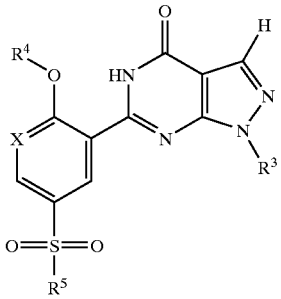

XXIIIC

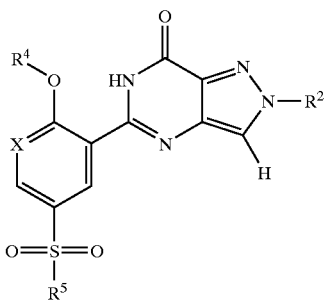

XXIIID

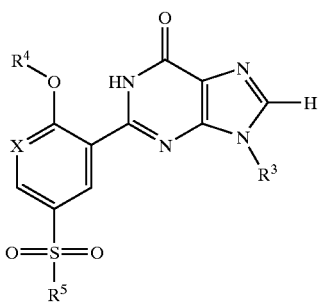

XXIIIE wherein X, R$^1$, R$^2$, R$^3$, R$^4$ and R$^5$ are as defined previously for compounds of formulae XXIIA, XXIIC, XXIID and XXIIE, with the appropriate halogen (e.g. bromination can be achieved by reacting with 1.5 to 2.0 equivalents of bromine and 1.5 to 2.0 equivalents of sodium acetate in acetic acid at between room and reflux temperature). The skilled person will recognise that although the above structures have been given discreet formulae descriptors (XXIIIA, XXIIIC, XXIIID and XXIIIE) for clarity, they are in fact a subset of formulae IA, IC, ID and IE wherein R$^3$, R$^1$, R$^3$ and R$^2$ are H respectively.

Compounds of formulae XXIIIA, XXIIIC, XXIIID and XXIIIE may be prepared by analogous conditions to those described for the preparation of corresponding compounds of formulae IA, IC, ID and IE in process 1.

6. Compounds of formula XIXE may alternatively be prepared by reaction of a compound of formula XXIVE:

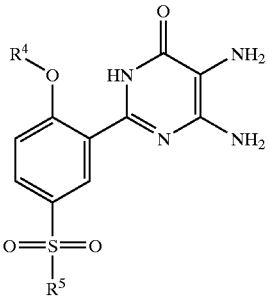

XXIVE wherein R$^4$ and R$^5$ are as defined previously for compounds of formula XIXE, with a compound of formula XXVE:

R$^2$—CHO                         XXVE wherein R$^2$ is as defined previously for compounds of formula XIXE, for example at between room and reflux temperature, optionally in the presence of a suitable mild oxidant (e.g. sodium metabisulfite), and optionally in an appropriate organic solvent (e.g. N,N-dimethylacetamide).

Compounds of formula XIXE may alternatively be prepared by reaction of compounds of formula XXIVE, as hereinbefore defined, with a compound of formula XXVIE:

R$^2$—C(O)OH                     XXVIE wherein R$^2$ is as defined previously for compounds of formula XIXE, or a suitable carboxylic acid derivative thereof (e.g. an acid halide or an ortho ester), for example at between room and reflux temperature, optionally in the presence of a suitable solvent (e.g. N,N-dimethyl formamide) and/or an appropriate base.

7. Compounds of formula IB may be prepared by cyclisation of compounds of formula XXVIIB:

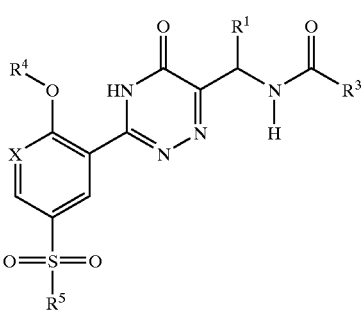

XXVIIB wherein R$^1$, R$^3$, R$^4$, R$^5$ and X are as defined previously for compounds of formula IB, for example under conditions known to those skilled in the art. Such conditions include reaction, at between room and reflux temperature, in the presence of a suitable (Lewis acidic) dehydrating agent (e.g. phosphorous oxychloride) and an appropriate solvent (e.g. 1,2-dichloroethane), or as otherwise described in the art.

Compounds of formula XXVIIB may be prepared by the reaction of compounds of formula XXVIIIB:

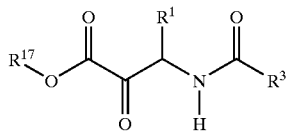

XXVIIIB wherein $R^{17}$ represents $C_1$–$C_6$ alkyl, and $R^1$ and $R^3$ are as defined previously for compounds of formula XXVIIB, with compounds of formula XXIXB:

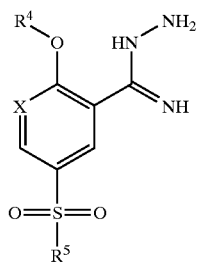

XXIXB or a suitable acid addition salt thereof (e.g. an hydrogen chloride salt), wherein $R^4$, $R^5$ and X are as defined previously for compounds of formula XXVIIB, for example under conditions known to those skilled in the art. Such conditions include, for example, reaction at between room and reflux temperature in a suitable solvent (e.g. ethanol, ether, 1,4-dioxane or N,N-dimethylformamide).

Compounds of formula XXVIIIB may be prepared via standard techniques, for example by decarboxylation of compounds of formula XXXB:

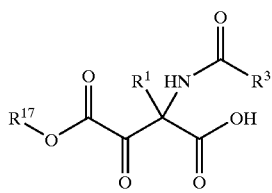

XXXB wherein $R^1$, $R^3$ and $R^{17}$ are as defined previously for compounds of formula XXVIIIB, for example under conditions known to those skilled in the art. Such conditions include, for example, reaction at elevated temperature (e.g. reflux temperature) in the presence of a suitable solvent (e.g. methanol or ethanol) and optionally in the presence of a suitable base (e.g. sodium hydrogencarbonate).

Compounds of formula XXXB may be prepared by reaction of compounds of formula XXXIB:

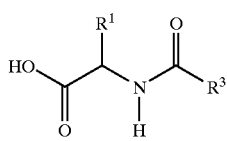

XXXIB wherein $R^1$ and $R^3$ are as defined previously for compounds of formula XXXB, with a compound of formula XXXIIB:

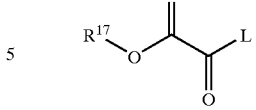

XXXIIB wherein $R^{17}$ is as defined previously for compounds of formula XXXB and L is as hereinbefore defined, for example under conditions known to those skilled in the art. Such conditions include reaction, at between room and reflux temperature, in the presence of a suitable organic solvent (e.g. THF or ether), an appropriate base (e.g. pyridine, sodium hydride, potassium tert-butoxide, lithium diisopropyl-amide, piperidine or triethylamine) optionally in the presence of a suitable catalyst (e.g. 4-(dimethylamino) pyridine), and optionally with the prior conversion of XXXIB into a 1,3-oxazol-5(4H)-one with excess XXXIIB (Dakin-West reaction).

Compounds of formula XXVIIIB may alternatively be prepared by reaction of a corresponding compound of formula XXXIIIB:

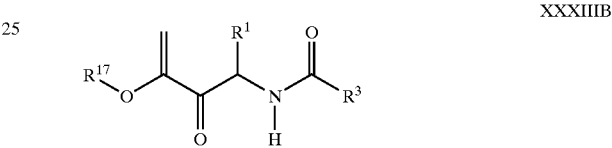

XXXIIIB wherein $R^1$, $R^3$ and $R^{17}$ are as defined previously for compounds of formula XXVIIIB, with ozone in a stream of oxygen, followed by reduction of the resulting ozonide, for example, for both steps, under conditions known to those skilled in the art. Conditions for the ozonation include, for example, reaction at sub-ambient temperature (e.g. −70° C.) in the presence of a suitable solvent (e.g. dichloromethane). Conditions for reduction of the intermediate ozonide include, for example, reaction at sub-ambient temperature (e.g. −70° C.) with a suitable reducing agent (e.g. dimethyl sulfide), followed by treatment (at the same temperature) with an appropriate base (e.g. pyridine).

Compounds of formula XXXIIIB may be prepared by reaction of a corresponding compound of formula XXXIVB:

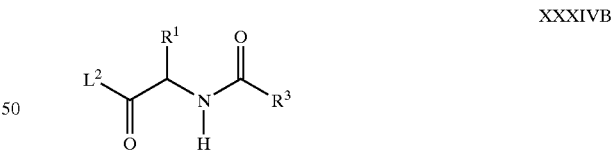

XXXIVB wherein $L^2$ represents a suitable leaving group (e.g. —N(CH$_3$)OCH$_3$ or halo) and $R^1$ and $R^3$ are as defined for compounds of formula XXXIIIB, with a compound of formula XXXVB:

XXXVB wherein M represents H or a suitable metal-containing moiety (e.g. Na, Li, Mg(II) halide, or a cuprate) and $R^{17}$ is as defined previously for compounds of formula XXXIIIB, for example under conditions known to those skilled in the art. Such conditions include, for example, reaction of a compound of formula XXXIVB at between −80° C. and room temperature in the presence of a suitable solvent (e.g. THF) with a mixture formed by reacting, at sub-ambient temperature (e.g. −78° C.), a compound of formula XXXVB in which M represents H (e.g. ethyl vinyl ether), a suitable organolithium reagent (e.g. tert-butyllithium), an appropriate solvent (e.g. THF) and, optionally, a source of a suitable metal salt (e.g. MgBr$_2$ diethyl etherate).

Compounds of formula XXXIVB may be prepared from corresponding compounds of formula XXXIB, as hereinbefore defined, under conditions known to those skilled in the art.

Compounds of formula XXVIIIB may alternatively be prepared by reaction of corresponding compounds of formula XXXVIB:

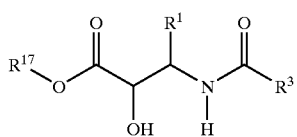

XXXVIB wherein $R^1$, $R^3$ and $R^{17}$ are as previously defined for compounds of formula XXVIIIB, with an oxidising agent (e.g. Dess-Martin periodinane) at between −78° C. and reflux temperature in a suitable solvent (e.g. DCM).

Compounds of formula XXXVIB may be prepared by the reaction of compounds of formula XXXVIIB:

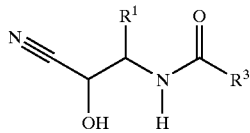

XXXVIIB wherein $R^1$ and $R^3$ are as previously defined for compounds of formula XXXVIB, with HCl$_{(g)}$ in $R^{17}$OH, wherein $R^{17}$ is as previously defined for compounds of formula XXXVIB, at between −10° C. and 20° C., followed by reaction with aqueous base (e.g. 10% Na$_2$CO$_3$ soln.) at between 20° C. and reflux temperature.

Compounds of formula XXXVIIB may be prepared by the reaction of compounds of formula XXXVIIIB:

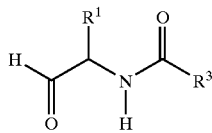

XXXVIIIB wherein $R^1$ and $R^3$ are as previously defined for compounds of formula XXXVIIB, with a source of cyanide (e.g. acetone cyanohydrin) in a suitable solvent (e.g. DCM), optionally in the presence of a base (e.g. Et$_3$N), at between 0° C. and reflux temperature.

Compounds of formula XXXVIIIB may be prepared by the reaction of compounds of formula XXXIXB:

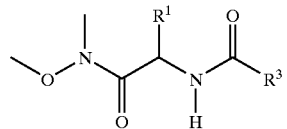

XXXIXB wherein $R^1$ and $R^3$ are as previously defined for compounds of formula XXXVIIIB, with a source of hydride (e.g. LiAlH$_4$) in a suitable solvent (e.g. THF) at between −78° C. and 20° C.

Compounds of formula XXXIXB may be prepared from compounds of formula XXXIB using conditions known to those skilled in the art.

Compounds of formula XXIXB may be prepared via standard techniques, for example by a reaction of a corresponding compound of formula XXXXB:

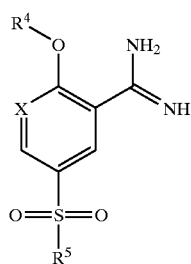

XXXXB or an acid addition salt thereof (e.g. a hydrogen chloride salt), wherein $R^4$, $R^5$ and X are as defined previously for compounds of formula XXIXB, with hydrazine, for example under conditions known to those skilled in the art. Such conditions include, for example, reaction at between −10° C. and room temperature in the presence of a suitable solvent (e.g. a lower alkyl (e.g. C$_{1-3}$) alcohol), or as otherwise described in the prior art.

Compounds of formula XXXXB may be prepared from compounds of formula XXXXIB, which in turn can be prepared from compounds of formula XXXXIIB, which in turn can be prepared from compounds of formula IV or a carboxylic acid derivative thereof, wherein $R^4$ and $R^5$ and X are as defined previously for compounds of formula XXXXB, under conditions known to those skilled in the art.

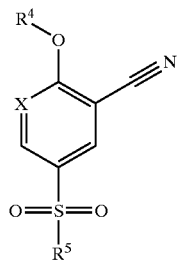

XXXXIB

-continued

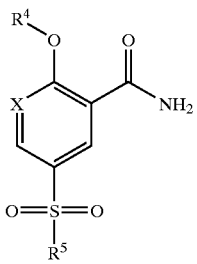

XXXXIIB

Compounds of formula XXIXB may alternatively be prepared by the reaction of compounds of formula XXXXIIIB:

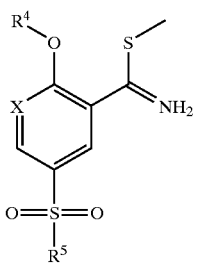

XXXXIIIB wherein $R^4$ and $R^5$ are as defined previously for compounds of formula XXIXB, with hydrazine in a suitable solvent (e.g. THF) at between 20° C. and reflux temperature.

Compounds of formula XXXXIIIB may be prepared by the reaction of compounds of formula XXXXIVB:

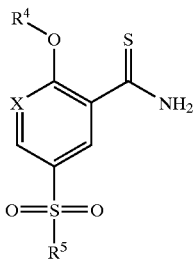

XXXXIVB wherein $R^4$ and $R^5$ are as defined previously for compounds of formula XXXXIIIB, with a methylating agent (e.g. iodomethane) in a suitable solvent (e.g. acetone) at between 20° C. and reflux temperature.

Compounds of formula XXXXIVB may be prepared by the reaction of compounds of formula XXXXIIB with Lawesson's reagent in a suitable solvent (e.g. toluene) at between 20° C. and reflux temperature.

Compounds of formulae IIIA, IIIC, IIID, IIIE, VII, X, XII (where X represents CH), XII, XV, XXIA, XXIC, XXID, XXIE, XXIVE, XXVE, XXVIE, XXXIB, XXXIIB and XXXVB and derivatives thereof, when not commercially available or not subsequently described, may be obtained either by analogy with the processes described hereinbefore, or by conventional synthetic procedures, in accordance with standard techniques, from readily available starting materials using appropriate reagents and reaction conditions. For example, compounds of formula XXIVE may be prepared by, or by analogy with, methods described in U.S. Pat. No. 4,039,544.

Substituents on the aryl and Het groups in the above-mentioned compounds may be introduced, and interconverted, using techniques which are known to those skilled in the art.

Further standard substituent or functional group interconversions and transformations that may be performed on compounds of formulae I, IA, IB, IC, ID, IE and their precursors include procedures described hereinafter. In this respect:

(i) alkoxycarbonyl may be hydrolysed to carboxy under acidic or basic conditions;

(ii) amino may be alkylated (either by reaction with an alkylating agent or by reductive alkylation) to give alkylamino or dialkylamino;

(iii) amino may be acylated to give acylamino or sulfonated to give sulfonylamino.

In addition, certain acyclic groups may be converted to certain heterocyclic groups using reagents and conditions known to those skilled in the art, for example as described in Comprehensive Heterocyclic Chemistry II, edited by A R Katritsky, C W Rees and EFV Scriven, 1$^{st}$ Edition, Elsevier Science Ltd., Volumes 1–11 (1996).

The compounds of the invention may be isolated from their reaction mixtures using conventional techniques.

It will be appreciated by those skilled in the art that, in the course of carrying out the above processes described above, the functional groups of intermediate compounds may need to be protected by protecting groups.

Functional groups which it is desirable to protect include hydroxy, amino and carboxylic acid. Suitable protecting groups for hydroxy include trialkylsilyl and diarylalkylsilyl groups (e.g. tert-butyldimethylsilyl, tert-butyldiphenylsilyl or trimethylsilyl), alkyl (e.g. methyl or methoxyethyl) and tetrahydropyranyl. Suitable protecting groups for amino include tert-butyloxycarbonyl, 9-fluorenylmethoxycarbonyl or benzyloxycarbonyl. Suitable protecting groups for carboxylic acid include $C_{1-6}$ alkyl or benzyl esters.

The protection and deprotection of functional groups may take place before or after any of the reaction steps described hereinbefore.

Protecting groups may be removed in accordance with techniques which are known to those skilled in the art.

The use of protecting groups is fully described in "Protective Groups in Organic Chemistry", edited by J W F McOmie, Plenum Press (1973), "Protective Groups in Organic Synthesis", 2$^{nd}$ edition, T W Greene & P G M Wutz, Wiley-Interscience (1991) and "Protecting Groups" by Philip J. Kocienski, Thieme, 1994.

Persons skilled in the art will also appreciate that, in order to obtain compounds of formulae I, IA, IB, IC, ID and IE, in an alternative, and, on some occasions, more convenient, manner, the individual process steps mentioned hereinbefore may be performed in a different order, and/or the individual reactions may be performed at a different stage in the overall route (i.e. substituents may be added to and/or chemical transformations performed upon, different intermediates to those mentioned hereinbefore in conjunction with a particular reaction). This will depend inter alia on factors such as the nature of other functional groups present in a particular substrate, the availability of key intermediates and the protecting group strategy (if any) to be adopted. Clearly, the type of chemistry involved will influence the choice of reagent that is used in the said synthetic steps, the need, and type, of protecting groups that are employed, and the sequence for accomplishing the synthesis.

Pharmaceutically acceptable acid addition salts of the compounds of formulae I, IA, IB, IC, ID and IE which contain a basic centre may be prepared in a conventional manner. For example, a solution of the free base may be treated with the appropriate acid, either neat or in a suitable solvent, and the resulting salt may then be isolated either by filtration of by evaporation under vacuum of the reaction solvent. Pharmaceutically acceptable base addition salts can be obtained in an analogous manner by treating a solution of a compound of formulae I, IA, IB, IC, ID and IE with the appropriate base. Both types of salt may be formed or interconverted using ion-exchange resin techniques.

The present invention also includes all suitable isotopic variations of a compound of formulae I, IA, IB, IC, ID or IE or a pharmaceutically acceptable salt thereof. An isotopic variation of a compound of formulae 1, IA, IB, IC, ID or IE, or a pharmaceutically acceptable salt thereof is defined as one in which at least one atom is replaced by an atom having the same atomic number but an atomic mass different from the atomic mass usually found in nature. Examples of isotopes that can be incorporated into compounds of formulae I, IA, IB, IC, ID or IE, and pharmaceutically acceptable salts thereof include isotopes of hydrogen, carbon, nitrogen, oxygen, phosphorus, sulphur, fluorine and chlorine such as $^2H$, $^3H$, $^{13}C$, $^{14}C$, $^{15}N$, 17O, 18O, 31p, 32p, $^{35}S$, $^{18}F$ and $^{36}Cl$, respectively. Certain isotopic variations of the compounds of formulae I, IA, IB, IC, ID or IE and pharmaceutically acceptable salts thereof, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as deuterium, i.e., H, may afford certain therapeutic advantages resulting from greater metabolic stability, for example, increased in vivo half-life or reduced dosage requirements and hence may be preferred in some circumstances. Isotopic variations of the compounds of formulae I, IA, IB, IC, ID or IE, and pharmaceutically acceptable salts thereof of this invention can generally be prepared by conventional procedures such as by the illustrative methods or by the preparations described in the Examples and Preparations hereafter using appropriate isotopic variations of suitable reagents.

It will be appreciated by those skilled in the art that certain protected derivatives of compounds of formulae I, IA, IB, IC, ID and IE, which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". Further, certain compounds of formulae I, IA, IB, IC, ID and IE may act as prodrugs of other compounds of formulae I, IA, IB, IC, ID and IE respectively.

All protected derivatives, and prodrugs, of compounds of formulae I, IA, IB, IC, ID and IE are included within the scope of the invention.

The present invention additionally comprises the combination of a cGMP $PDE_5$ inhibitor compound of the general formulae I, IA, IB, IC, ID or IE, wherein said combination can be administered by sequential, simultaneous or joint administration of a compound of the general formulae I, IA, IB, IC, ID or IE, with:

(1) one or more naturally occurring or synthetic prostaglandins or esters thereof. Suitable prostaglandins for use herein include compounds such as alprostadil, prostaglandin $E_1$, prostaglandin $E_0$, 13, 14-dihydroprostaglandin $E_1$, prostaglandin $E_2$, eprostinol, natural synthetic and semi-synthetic prostaglandins and derivatives thereof including those described in U.S. Pat. No. 6,037,346 issued on Mar. 14, 2000 and incorporated herein by reference, $PGE_0$, $PGE_1$, $PGA_1$, $PGB_1$, $PGF_1$ α, 19-hydroxy $PGA_1$, 19-hydroxy-$PGB_1$, $PGE_2$, $PGB_2$, 19-hydroxy-$PGA_2$, 19-hydroxy-$PGB_2$, $PGE_3$α, carboprost tromethamine dinoprost, tromethamine, dinoprostone, lipo prost, gemeprost, metenoprost, sulprostune, tiaprost and moxisylate; and/or (2) one or more α-adrenergic receptor antagonist compounds also known as α-adrenoceptors or α-receptors or α blockers. Suitable compounds for use herein include: the α-adrenergic receptors as described in PCT application WO99/30697 published on Jun. 14, 1998, the disclosures of which relating to a-adrenergic receptors are incorporated herein by reference and include, selective $α_1$-adrenoceptors or $α_2$-adrenoceptors and non-selective adrenoceptors, suitable $α_1$-adrenoceptors include: phentolamine, phentolamine mesylate, trazodone, alfuzosin, indoramin, naftopidil, tamsulosin, dapiprazole, phenoxybenzamine, idazoxan, efaraxan, yohimbine, rauwolfa alkaloids, Recordati 15/2739, SNAP 1069, SNAP 5089, RS17053, SL 89.0591, doxazosin, terazosin, abanoquil and prazosin; $α_2$-blockers from U.S. Pat. No. 6,037,346 [Mar. 14, 2000] dibenarnine, tolazoline, trimazosin and dibenarnine; α-adrenergic receptors as described in U.S. Pat. Nos. 4,188,390; 4,026,894; 3,511,836; 4,315,007; 3,527,761; 3,997,666; 2,503,059; 4,703,063; 3,381,009; 4,252,721 and 2,599,000 each of which is incorporated herein by reference; $α_2$-Adrenoceptors include: clonidine, papaverine, papaverine hydrochloride, optionally in the presence of a cariotonic agent such as pirxamine; and/or (3) one or more NO-donor (NO-agonist) compounds. Suitable NO-donor compounds for use herein include organic nitrates, such as mono- di or tri-nitrates or organic nitrate esters including glyceryl brinitrate (also known as nitroglycerin), isosorbide 5-mononitrate, isosorbide dinitrate, pentaerythritol tetranitrate, erythrityl tetranitrate, sodium nitroprusside (SNP), 3-morpholinosydnonimine molsidomine, S-nitroso-N-acetyl penicilliamine (SNAP) S-nitroso-N-glutathione (SNO-GLU), N-hydroxy-L-arginine, amylnitrate, linsidomine, linsidomine chlorohydrate, (SIN-1) S-nitroso-N-cysteine, diazenium diolates, (NONOates), 1,5-pentanedinitrate, L-arginene, ginseng, zizphi fructus, molsidomine, Re-2047, nitrosylated maxisylyte derivatives such as NMI-678-11 and NMI-937 as described in published PCT application WO 0012075; and/or (4) one or more potassium channel openers. Suitable potassium channel openers for use herein include nicorandil, cromokalim, levcromakalim, lemakalim, pinacidil, cliazoxide, minoxidil, charybdotoxin, glyburide, 4-amini pyridine, $BaCl_2$; and/or (5) one or more dopaminergic agents, preferably apomorphine or a selective D2, D3 or D2/D3 agonist such as pramipexol and ropirinol (as claimed in WO 0023056), L-Dopa or carbi dopa, PNU 95666 (as claimed in WO 0040226); and/or (6) one or more vasodilator agents. Suitable vasodilator agents for use herein include nimodepine, pinacidil, cyclandelate, isoxsuprine, chloroprumazine, halo peridol, Rec 15/2739, trazodone; and/or (7) one or more thromboxane A2 agonists; and/or (8) one or more ergot alkoloids; Suitable ergot alkaloids are described in U.S. Pat. No. 6,037,346 issued on Mar.

14, 2000 and include acetergamine, brazergoline, bromerguride, cianergoline, delorgotrile, disulergine, ergonovine maleate, ergotamine tartrate, etisulergine, lergotrile, lysergide, mesulergine, metergoline, metergotamine, nicergoline, pergolide, propisergide, proterguride, terguride; and/or (9) one or more compounds which modulate the action of atrial natruretic factor (also known as atrial naturetic peptide), B and C type naturetic factors such as inhibitors or neutral endopeptidase; and/or

(10) one or more compounds which inhibit angiotensin-converting enzyme such as enapril, and one or more combined inhibitors of angiotensin-converting enzyme and neutral endopeptidase such as omapatrilat; and/or

(11) one or more angiotensin receptor antagonists such as losartan; and/or

(12) one or more substrates for NO-synthase, such as L-arginine; and/or

(13) one or more calcium channel blockers such as amlodipine; and/or

(14) one or more antagonists of endothelin receptors and inhibitors or endothelin-converting enzyme; and/or

(15) one or more cholesterol lowering agents such as statins (e.g. atorvastatin/Lipitor—trade mark) and fibrates; and/or

(16) one or more antiplatelet and antithrombotic agents, e.g. tPA, uPA, warfarin, hirudin and other thrombin inhibitors, heparin, thromboplastin activating factor inhibitors; and/or

(17) one or more insulin sensitising agents such as rezulin and hypoglycaemic agents such as glipizide; and/or

(18) one or more COX 2 inhibitors; and/or

(19) pregabalene; and/or

(20) gabapentene; and/or

(21) one or more acetylcholinesterase inhibitors such as donezipil; and/or

(22) one or more steroidal anti-inflammatory agents; and/or

(23) one or more estrogen agonists and/or estrogen antagonists, preferably raloxifene or lasofoxifene, (−)-cis-6-phenyl-5-[4-(2-pyrrolidin-1-yl-ethoxy)-phenyl]-5,6,7,8-tetrahydronaphthalene-2-ol and pharmaceutically acceptable salts thereof (compound A below) the preparation of which is detailed in WO 96/21656.

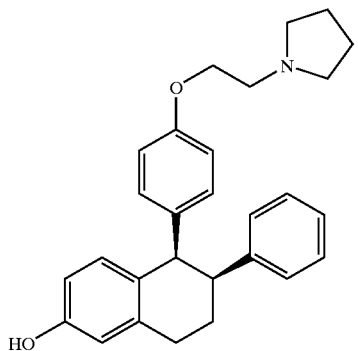

Compound A

(24) one or more one or more of a further PDE inhibitor, more particularly a PDE 2, 4, 7 or 8 inhibitor, preferably PDE2 inhibitor, said inhibitors preferably having an IC50 against the respective enzyme of less than 100 nM: and/or

(25) one or more of an NPY (neuropeptide Y) inhibitor, more particularly NPY1 or NPY5 inhibitor, preferably NPY1 inhibitor, preferably said NPY inhibitors (including NPY Y1 and NPY Y5) having an IC50 of less than 100 nM, more preferably less than 50 nM, suitable NPY and in particular NPY1 inhibitor compounds are described in EP-A-1097718; and/or

(26) one or more of vasoactive intestinal peptide (VIP), VIP mimetic, more particularly mediated by one or more of the VIP receptor subtypes VPAC1, VPAC or PACAP (pituitary adenylate cyclase activating peptide), one or more of a VIP receptor agonist or a VIP analogue (eg Ro-125-1553) or a VIP fragment, one or more of a α-adrenoceptor antagonist with VIP combination (eg Invicorp, Aviptadil); and/or

(27) one or more of a melanocortin receptor agonist or modulator or melanocortin ehancer, such as melanotan II, PT-14, PT-141 or compounds claimed in WO-09964002, WO-00074679, WO-09955679, WO-00105401, WO-00058361, WO-00114879, WO-00113112, WO-09954358; and/or

(28) one or more of a serotonin receptor agonist, antagonist or modulator, more particularly agonists, antagonists or modulators for 5HT1A (including VML 670), 5HT2A, 5HT2C, 5HT3 and/or 5HT6 receptors, including those described in WO-09902159, WO-00002550 and/or WO-00028993; and/or

(29) one or more of a modulator of transporters for noradrenaline, dopamine and/or serotonin, such as bupropion, GW-320659; and/or

(30) one or more of a purinergic receptor agonist and/or modulator; and/or

(31) one or more of a neurokinin (NK) receptor antagonist, including those described in WO-09964008; and/or

(32) one or more of an opioid receptor agonist, antagonist or modulator, preferably agonists for the ORL-1 receptor; and/or

(33) one or more of an agonist or modulator for oxytocin/vasopressin receptors, preferably a selective oxytocin agonist or modulator; and/or

(34) one or more modulators of cannabinoid receptors; and/or

(35) one or more of an NEP inhibitor, preferably wherein said NEP is EC 3.4.24.11 and more preferably wherein said NEP inhibitor is a selective inhibitor for EC 3.4.24.11, more preferably a selective NEP inhibitor is a selective inhibitor for EC 3.4.24.11, which has an $IC_{50}$ of less than 100 nM (e.g. ompatrilat, sampatrilat) suitable NEP inhibitor compounds are described in EP-A-1097719; and/or

(36) one or more compounds which inhibit angiotensin-converting enzyme such as enalapril, and one or more combined inhibitors of angiotensin-converting enzyme and neutral endopeptidase such as omapatrilat; and/or

(37) one or more tricyclic antidepressants, e.g. amitriptiline; and/or

(38) one or more non-steroidal anti-inflammatory agents; and/or

(39) one or more angiotensin-converting enzyme (ACE) inhibitors, e.g. quinapril; and/or

(40) one or more anti-depressants (such as clomipramine and SSRls (such as paroxetine and sertaline).

wherein said combination can be in the form of co-administration, simultaneous administration, concurrent administration, or stepwise administration.

Medical Use

The compounds of the invention are useful because they possess pharmacological activity in animals, especially mammals, including humans. They are therefore indicated as pharmaceuticals, as well as for use as animal medicaments.

In particular, compounds of the invention have been found to be potent and selective inhibitors of cGMP PDE5, for example as demonstrated in the tests described below, and are thus useful in the treatment of medical conditions in humans and other animals, in which cGMP PDE5 is indicated, and in which inhibition of cGMP PDE5 is desirable.

By the term "treatment", we include both therapeutic (curative), palliative or prophylactic treatment.

Thus, according to a further aspect of the invention there is provided the use of the compounds of the invention in the manufacture of a medicament for the treatment of a medical condition in which cGMP PDE5 is indicated. There is further provided the use of the compounds of the invention in the manufacture of a medicament for the treatment of a medical condition in which inhibition of cGMP PDE5 is desirable.

The compounds of the invention are expected to be useful for the curative, palliative or prophylactic treatment of mammalian sexual disorders or any of the other conditions or disorders detailed hereinbefore. In particular, the compounds are of value in the treatment of mammalian sexual dysfunctions such as male erectile dysfunction (MED), impotence, female sexual dysfunction (FSD), clitoral dysfunction, female hypoactive sexual desire disorder, female sexual arousal disorder, female sexual pain disorder or female sexual orgasmic dysfunction (FSOD) as well as sexual dysfunction due to spinal cord injury or selective serotonin re-uptake inhibitor (SSRI) induced sexual dysfunction but, clearly, will be useful also for treating other medical conditions for which a potent and selective cGMP PDE5 inhibitor is indicated. Such conditions include premature labour, dysmenorrhoea, benign prostatic hyperplasia (BPH), bladder outlet obstruction, incontinence, stable, unstable and variant (Prinzmetal) angina, hypertension, pulmonary hypertension, chronic obstructive pulmonary disease, coronary artery disease, congestive heart failure, atherosclerosis, conditions of reduced blood vessel patency, e.g. post-percutaneous transluminal coronary angioplasty (post-PTCA), peripheral vascular disease, stroke, nitrate induced tolerance, bronchitis, allergic asthma, chronic asthma, allergic rhinitis, diseases and conditions of the eye such as glaucoma, optic neuropathy, macular degeneration, elevated intra-ocular pressure, retinal or arterial occulsion and diseases characterised by disorders of gut motility, e.g. irritable bowel syndrome (IBS).

Further medical conditions for which a potent and selective cGMP PDE5 inhibitor is indicated, and for which treatment with compounds of the present invention may be useful include pre-eclampsia, Kawasaki's syndrome, nitrate tolerance, multiple sclerosis, diabetic nephropathy, peripheral diabetic neuropathy, Alzheimer's disease, acute respiratory failure, psoriasis, skin necrosis, cancer, metastasis, baldness, nutcracker oesophagus, diabetes mellitus, the insulin resistance syndrome, anal fissure, haemorrhoids, hypoxic vasoconstriction as well as the stabilisation of blood pressure during haemodialysis.

Particularly preferred conditions include MED and FSD.

Thus, the invention provides a method of treating or preventing a medical condition for which a cGMP PDE5 inhibitor is indicated, in an animal (e.g. a mammal, including a human being), which comprises administering a therapeutically effective amount of a compound of the invention to an animal in need of such treatment.

Pharmaceutical Preparations

The compounds of the invention will normally be administered orally or by any parenteral route, in the form of pharmaceutical preparations comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

The compounds of the invention may also be combined with any other drugs useful in the inhibition of cGMP-PDEs, such as cGMP-PDE5.

The compounds of the invention, their pharmaceutically acceptable salts, and pharmaceutically acceptable solvates of either entity can be administered alone but, in human therapy will generally be administered in admixture with a suitable pharmaceutical excipient diluent or carrier selected with regard to the intended route of administration and standard pharmaceutical practice.

For example, the compounds of the invention or salts or solvates thereof can be administered orally, buccally or sublingually in the form of tablets, capsules (including soft gel capsules), ovules, elixirs, solutions or suspensions, which may contain flavouring or colouring agents, for immediate-, delayed-, controlled-release such as modified-, dual-, sustained-, or pulsatile delivery applications. The compounds of the invention may also be administered via intracavernosal injection. The compounds of the invention may also be administered via fast dispersing or fast dissolving dosages forms.

Such tablets may contain excipients such as microcrystalline cellulose, lactose, sodium citrate, calcium carbonate, dibasic calcium phosphate, glycine and starch (preferably corn, potato or tapioca starch), disintegrants such as sodium starch glycollate, croscarmellose sodium and certain complex silicates, and granulation binders such as polyvinylpyrrolidone, hydroxypropylmethyl cellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

Modified release and pulsatile release dosage forms may contain excipients such as those detailed for immediate release dosage forms together with additional excipients that act as release rate modifiers, these being coated on and/or included in the body of the device. Release rate modifiers include, but are not exclusively limited to, hydroxypropylmethyl cellulose, methyl cellulose, sodium carboxymethylcellulose, ethyl cellulose, cellulose acetate, polyethylene oxide, Xanthan gum, Carbomer, ammonio methacrylate copolymer, hydrogenated castor oil, carnauba wax, paraffin wax, cellulose acetate phthalate, hydroxypropylmethyl cellulose phthalate, methacrylic acid copolymer and mixtures thereof. Modified release and pulsatile release dosage forms may contain one or a combination of release rate modifying excipients. Release rate modifying excipients maybe present both within the dosage form i.e. within the matrix, and/or on the dosage form i.e. upon the surface or coating.

Fast dispersing or dissolving dosage formulations (FDDFs) may contain the following ingredients: aspartame, acesulfame potassium, citric acid, croscarmellose sodium, crospovidone, diascorbic acid, ethyl acrylate, ethyl cellulose, gelatin, hydroxypropylmethyl cellulose, magnesium stearate, mannitol, methyl methacrylate, mint flavouring, polyethylene glycol, fumed silica, silicon dioxide, sodium starch glycolate, sodium stearyl fumarate, sorbitol, xylitol. The terms dispersing or dissolving as used herein to describe FDDFs are dependent upon the solubility of the drug substance used i.e. where the drug substance is insoluble a fast dispersing dosage form can be prepared and where the drug substance is soluble a fast dissolving dosage form can be prepared.

The compounds of the invention can also be administered parenterally, for example, intracavernosally, intravenously, intra-arterially, intraperitoneally, intrathecally, intraventricularly, intraurethrally intrasternally, intracranially, intramuscularly or subcutaneously, or they may be administered by infusion techniques. For such parenteral administration they are best used in the form of a sterile aqueous solution which may contain other substances, for example, enough salts or glucose to make the solution isotonic with blood.

The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

For oral and parenteral administration to human patients, the daily dosage level of the compounds of the invention or salts or solvates thereof will usually be from 10 to 500 mg (in single or divided doses).

Thus, for example, tablets or capsules of the compounds of the invention or salts or solvates thereof may contain from 5 mg to 250 mg of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention. The skilled person will also appreciate that, in the treatment of certain conditions (including MED and FSD), compounds of the invention may be taken as a single dose on an "as required" basis (i.e. as needed or desired).

Example Tablet Formulation

In general a tablet formulation could typically contain between about 0.01 mg and 500 mg of a compound according to the present invention (or a salt thereof) whilst tablet fill weights may range from 50 mg to 1000 mg. An example formulation for a 10 mg tablet is illustrated:

| Ingredient | % w/w |
|---|---|
| Compound of Example 19 | 10.000* |
| Lactose | 64.125 |
| Starch | 21.375 |
| Croscarmellose Sodium | 3.000 |
| Magnesium Stearate | 1.500 |

*This quantity is typically adjusted in accordance with drug activity.

Such tablets can be manufactured by standard processes, for example, direct compression or a wet or dry granulation process. The tablet cores may be coated with appropriate overcoats.

The compounds of the invention can also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A [trade mark] or 1,1,1,2,3,3,3-heptafluoropropane (HFA 227EA [trade mark]), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

Aerosol or dry powder formulations are preferably arranged so that each metered dose or "puff" contains from 1 to 50 mg of a compound of the invention for delivery to the patient. The overall daily dose with an aerosol will be in the range of from 1 to 50 mg which may be administered in a single dose or, more usually, in divided doses throughout the day.

The compounds of the invention may also be formulated for delivery via an atomiser. Formulations for atomiser devices may contain the following ingredients as solubilisers, emulsifiers or suspending agents: water, ethanol, glycerol, propylene glycol, low molecular weight polyethylene glycols, sodium chloride, fluorocarbons, polyethylene glycol ethers, sorbitan trioleate, oleic acid.

Alternatively, the compounds of the invention or salts or solvates thereof can be administered in the form of a suppository or pessary, or they may be applied topically in the form of a gel, hydrogel, lotion, solution, cream, ointment or dusting powder. The compounds of the invention or salts or solvates thereof may also be dermally administered. The compounds of the invention or salts or solvates thereof may also be transdermally administered, for example, by the use of a skin patch. They may also be administered by the ocular, pulmonary or rectal routes.

For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the compounds of the invention or salts or solvates thereof can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The compounds of the invention may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO-A-91/11172, WO-A-94/02518 and WO-A-98/55148.

Generally, in humans, oral administration of the compounds of the invention is the preferred route, being the most convenient and, for example in MED, avoiding the well-known disadvantages associated with intracavernosal (i.c.) administration. A preferred oral dosing regimen in MED for a typical man is from 25 to 250 mg of compound when required. In circumstances where the recipient suffers from a swallowing disorder or from impairment of drug absorption after oral administration, the drug may be administered parenterally, sublingually or buccally.

For veterinary use, a compound of the invention, or a veterinarily acceptable salt thereof, or a veterinarily acceptable solvate or pro-drug thereof, is administered as a suitably acceptable formulation in accordance with normal veterinary practice and the veterinary surgeon will determine the dosing regimen and route of administration which will be most appropriate for a particular animal.

Thus, according to a further aspect of the invention there is provided a pharmaceutical formulation including a compound of the invention in admixture with a pharmaceutically or veterinarily acceptable adjuvant, diluent or carrier.

In addition to the fact that compounds of the invention inhibit cyclic guanosine 3',5'-monophosphate phosphodiesterases (cGMP PDEs) and in particular, are potent and selective inhibitors of cGMP PDE5, compounds of the invention may also have the advantage that they may be more efficacious than, be less toxic than, have a broader range of activity than, be more potent than, produce fewer side effects than, be more easily absorbed than, or they may have other useful pharmacological properties over, compounds known in the prior art.

Bioavailability

Preferably the compounds of the invention are orally bioavailable. Oral bioavailablity refers to the proportion of an orally administered drug that reaches the systemic circulation. The factors that determine oral bioavailability of a drug are dissolution, membrane permeability and metabolic stability. Typically, a screening cascade of firstly in vitro and then in vivo techniques is used to determine oral bioavailablity.

Dissolution, the solubilisation of the drug by the aqueous contents of the gastro-intestinal tract (GIT), can be predicted from in vitro solubility experiments conducted at appropriate pH to mimic the GIT. Preferably the compounds of the invention have a minimum solubility of 50 mcg/ml. Solubility can be determined by standard procedures known in the art such as described in Adv. Drug Deliv. Rev. 23, 3–25, 1997.

Membrane permeability refers to the passage of the compound through the cells of the GIT. Lipophilicity is a key property in predicting this and is defined by in vitro Log $D_{7.4}$ measurements using organic solvents and buffer. Preferably the compounds of the invention have a Log $D_{7.4}$ of –2 to +4, more preferably –1 to +2. The log D can be determined by standard procedures known in the art such as described in J. Pharm. Pharmacol. 1990, 42:144.

Cell monolayer assays such as caco-2 add substantially to prediction of favourable membrane permeability in the presence of efflux transporters such as p-glycoprotein, so-called caco-2 flux. Preferably, compounds of the invention have a caco-2 flux of greater than $2\times10^{-6}$ $cms^{-1}$, more preferably greater than $5\times10^{-6}$ $cms^{-1}$. The caco flux value can be determined by standard procedures known in the art such as described in J. Pharm. Sci, 1990, 79, 595–600

Metabolic stability addresses the ability of the GIT or the liver to metabolise compounds during the absorption process: the first pass effect. Assay systems such as microsomes, hepatocytes etc. are predictive of metabolic liability. Preferably the compounds of the Examples show metabolic stablity in the assay system that is commensurate with an hepatic extraction of less then 0.5. Examples of assay systems and data manipulation are described in Curr. Opin. Drug Disc. Devel., 201, 4, 36–44, Drug Met. Disp., 2000, 28, 1518–1523

Because of the interplay of the above processes further support that a drug will be orally bioavailable in humans can be gained by in vivo experiments in animals. Absolute bioavailability is determined in these studies by administering the compound separately or in mixtures by the oral route. For absolute determinations (% absorbed) the intravenous route is also employed. Examples of the assessment of oral bioavailability in animals can be found in Drug Met. Disp., 2001, 29, 82–87; J. Med Chem, 1997, 40, 827–829, Drug Met. Disp., 1999, 27, 221–226

The biological activities of the compounds of the present invention were determined by the following test methods.

Phosphodiesterase (PDE) Inhibitory Activity

The compounds of the present invention are potent and selective cGMP PDE5 inhibitors. In vitro PDE inhibitory activities against cyclic guanosine 3',5'-monophosphate (cGMP) and cyclic adenosine 3',5'-monophosphate (cAMP) phosphodiesterases were determined by measurement of their $IC_{50}$ values (the concentration of compound required for 50% inhibition of enzyme activity).

The required PDE enzymes were isolated from a variety of sources, including human corpus cavernosum, human platelets, human cardiac ventricle, human skeletal muscle and human and canine retina, essentially by the method of W. J. Thompson and M. M. Appleman (Biochem., 1971, 10, 311). In particular, the cGMP-specific PDE (PDE5) and the cGMP-inhibited cAMP PDE (PDE3) were obtained from human corpus cavernosum tissue or human platelets; the cGMP-stimulated PDE (PDE2) was obtained from human corpus cavernosum or human platelets; the calcium/calmodulin (Ca/CAM)-dependent PDE (PDE1) from human cardiac ventricle; the cAMP-specific PDE (PDE4) from recombinant clone or human skeletal muscle; and the photoreceptor PDE (PDE6) from canine or human retina. Phosphodiesterases 7–11 were generated from full length human recombinant clones transfected into SF9 cells.

Assays were performed either using a modification of the "batch" method of W. J. Thompson et al. (Biochem., 1979, 18, 5228) or using a scintillation proximity assay for the direct detection of AMP/GMP using a modification of the protocol described by Amersham plc under product code TRKQ7090/7100. In summary, the effect of PDE inhibitors was investigated by assaying a fixed amount of enzyme in the presence of varying inhibitor concentrations and low substrate, (cGMP or cAMP in a 3:1 ratio unlabelled to [$^3$H]-labeled at a conc ~½ $K_m$) such that $IC_{50} \cong K_i$. The final assay volume was made up to 102 µl with assay buffer [20 mM Tris-HCl pH 7.4, 5 mM $MgCl_2$, 1 mg/ml bovine serum albumin]. Reactions were initiated with enzyme, incubated for 30–60 min at 30° C. to give <30% substrate turnover and terminated with 50 µl yttrium silicate SPA beads (containing 3 mM of the respective unlabelled cyclic nucleotide for PDEs 3, 9 and 11). Plates were resealed and shaken for 20 min, after which the beads were allowed to settle for 30 min in the dark and then counted on a TopCount plate reader (Packard, Meriden, Conn.). Radioactivity units were converted to % activity of an uninhibited control (100%), plotted against inhibitor concentration and inhibitor $IC_{50}$ values obtained using the 'Fit Curve' Microsoft Excel extension or inhouse equivalent. Results from these tests show that the compounds of the present invention are potent and selective inhibitors of cGMP-specific PDE5.

Functional Activity

This can be assessed in vitro by determining the capacity of a compound of the invention to enhance sodium nitroprusside-induced relaxation of pre-contracted rabbit corpus cavernosum tissue strips, as described by S. A. Ballard et al. (Brit. J. Pharmacol., 1996, 118 (suppl.), abstract 153P).

In Vivo Activity

This can be assessed by screening the compounds of the invention in anaesthetised dogs to determine their capacity, after i.v. administration, to enhance the pressure rises in the corpora cavernosa of the penis induced by intracavernosal injection of sodium nitroprusside, using a method based on that described by Trigo-Rocha et al. (Neurourol. and Urodyn., 1994, 13, 71).

Safety Profile

Compounds of the invention can be tested at varying i.v and p.o. doses in animals such as mouse and dog, observing for any untoward effects.

In Vitro Metabolism

In vitro metabolism experiments were carried out in the hepatic microsomal fractions from man. Transplant-quality human liver tissue was obtained from the International Institute for the Advancement of Medicine (Exton, Pa., USA). Microsomes were prepared according to the method described in *Biochemical Pharmacology*, 1966, 48, 2147–2156 and stored at −80° C. The concentrations of protein and cytochrome P450 were determined by standard methods described in *Journal of Biological Chemistry*, 1951, 193, 265–275 and *Journal of Biological Chemistry*, 1964, 239, 2370–2378.

Microsomal incubations (1.5 ml) were prepared containing 0.5 µM cytochrome P450, 200 mM phosphate buffer (pH 7.4), 0.1 M $MgCl_2$, 0.1 M isocitric acid, 1 unit/ml isocitrate dehydrogenase and 20 mM β-NADP. Compounds under study were added after a 5 min preincubation at 37° C. to give an initial substrate concentration of 1 µM. The mixture was incubated at 37° C. and samples (100 µl) were removed for analysis for up to 60 min. Metabolism in samples was terminated by the addition of NaOH (0.1 M) containing an internal standard (chosen to have similar physicochemical properties to compounds under study), followed by extraction into ethyl acetate (2 ml). The extracts were evaporated to dryness and analysed by LC-MS/MS (Hewlett Packard HP1100 binary pump, Hypersil HS100 C18, 5 cm by 4.6 mm internal diameter, 5 µm column using a mobile phase of 2 mM ammonium acetate in 90:10 methanol/water, aqueous portion adjusted to pH 4 with glacial acetic acid, and a flowrate of 1 ml/min). The mass spectrometer was a Sciex API 2000 with TurbolonSpray interface using a positive ion multiple reaction monitoring (MRM) detection mode. Nitrogen was used as curtain, nebuliser, TurbolonSpray and collision gases, and the TurbolonSpray temperature was 100° C. Typical voltages were as follows: IS=5.2 kV; RNG=380 V; Q0=−10 V; IQ1=−11 V; ST=−15;RO1=−11 V; MU=gain adjusted as per Sciex user manual. Collision energy was 55 eV for high MRM, OR=65 V. Dwell time was 200 msec with a 50 msec pause. Data was acquired using MSExpress v 1.1 and processed using Macquan 1.5 (PE Sciex)). Disappearance rate constants (k) in human microsomal preparations were determined by linear regression of the log ratio (compound under study/internal standard) versus time. The in vitro human microsomal half-lives were determined according to the equation $t_{1/12}$=In 2/k. Results from these studies show that the compounds of the present invention have human liver microsome (HLM) half-lives greater than the HLM half-lives of known compounds of the art.

Thus a particular advantage of the compounds of the invention is that they have longer in vitro microsomal half-lives than compounds of the art. Such improved in vitro microsomal half-lives are indicative of reduced clearance in vivo.

Preferred compounds of the present invention, such as those of Examples 1–22, 24–26 and 28–29 have $IC_{50}$ values of less than about 30 nM for the PDE5 enzyme. More preferred compounds, such as those of Examples 1–3,5, 7–19, 24–25 and 28–29 have $IC_{50}$ values of less than about 10 nM for the PDE5 enzyme.

Especially preferred herein are compounds which have an $IC_{50}$ value of less than about 30 nM, and more preferably less than 10 nM for the PDE5 enzyme and especially less than 5 nM for the PDE5 enzyme in combination with selectivity of greater than 10-fold, more preferably greater than 50-fold, more preferably greater than 100-fold and most preferably greater than 200-fold selectivity for the PDE5 enzyme versus the PDE6 enzyme.

An especially preferred subset of the compounds described in the previous paragraph are compounds with human liver microsome (HLM) half-lives greater than about 30 minutes, more preferably greater than 60 minutes, and most preferably greater than 120 minutes—when measured according to the methods detailed hereinbefore. Preferred compounds herein having HLM half-lifes greater than or equal to about 30 minutes include the compounds of examples 1, 2, 9, 11, 12, 14, 18 and 19.

Those skilled in the art will recognise that an increase in HLM half-life is predictive of reduced clearance in man for compounds cleared predominantly by cytochrome P450 mediated metabolism.

EXAMPLES AND PREPARATIONS

The synthesis of the compounds of the invention and of the intermediates for use therein are illustrated by the following Examples and Preparations.

$^1$H nuclear magnetic resonance (NMR) spectra were recorded using either a Varian Unity 300 or a Varian Inova 400 spectrometer and were in all cases consistent with the proposed structures. Characteristic chemical shifts (δ) are given in parts-per-million downfield from tetramethylsilane using conventional abbreviations for designation of major peaks: e.g. s, singlet; d, doublet; t, triplet; q, quartet; m, multiplet; br, broad.

Mass spectra (m/z) were recorded using a Fisons Instruments Trio mass spectrometer in the thermospray ionisation mode (TSP) or using a Finnigan navigator in electrospray ionisation mode (ES)—positive and/or negative ionisation mode.

Optical rotations were measured on a Perkin Elmer 341 polarimeter.

As used herein, the term "column chromatography" refers to normal phase chromatography using silica gel (0.04–0.06 mm).

Glossary

| | |
|---|---|
| DCM | Dichloromethane |
| DMF | Dimethylformamide |
| DMSO | Dimethylsulphoxide |
| Et | Ethyl |
| EtOAc | Ethyl acetate |
| KHMDS | Potassium bis(trimethylsilyl)amide |
| Me | Methyl |
| mp | melting point |
| nOe | nuclear Overhauser effect |

Synthesis of Intermediates

Preparation 1

Methyl 2-hydroxy-5-(methylsulfonyl)benzoate

A solution of 2-hydroxy-5-(methylsulfonyl)benzoic acid (5.80 g, 26.8 mmol, prepared using procedure in *J. Chem. Soc., Perkin Trans* 1 1978, 6, 633–638) in MeOH (150 ml) at 0° C. was saturated with HCl (g). The solution was warmed to r.t. and heated to reflux for 3 h. The solid which formed upon cooling was filtered and dried to afford the title compound (4.40 g, 19.1 mmol, 71%).

$^1$H NMR (400 MHz, $d_6$-DMSO) δ 11.10 (s, 1H), 8.20 (s, 1H), 7.90 (d, 1H), 7.15 (d, 1H), 3.85 (s, 3H), 3.10 (s, 3H). MS (TSP) m/z 248 ($MNH_4^+$).

Preparation 2

Methyl 2-ethoxy-5-(methylsulfonyl)benzoate

A mixture containing the title compound of preparation 1 (4.40 g, 19.1 mmol), iodoethane (4.88 g, 31.2 mmol), $K_2CO_3$ (3.10 g, 22.5 mmol) in MeCN (100 ml) was heated to 70° C. for 18 h. The mixture was cooled, filtered, and the filtrate was concentrated in vacuo to afford the title compound as a white solid (4.70 g, 18.2 mmol, 95%).

$^1$H NMR (400 MHz, $CDCl_3$) δ 8.35 (s, 1H), 8.00 (d, 1H), 7.10 (d, 1H), 4.20 (q, 2H), 3.90 (s, 3H), 3.00 (s, 3H), 1.50 (t, 3H). MS (TSP) m/z 276 ($MNH_4^+$), 259 ($MH^+$).

Preparation 3

2-Ethoxy-5-(methylsulfonyl)benzoic acid

A solution of the title compound of preparation 2 (4.80 g, 18.6 mmol) in MeOH (80 ml) and 1M NaOH (22 ml, 22 mmol) was stirred at 20° C. for 24 h. The solution was concentrated in vacuo, and water (20 ml) was added to the residue. The mixture was acidified to pH 1 with 2M HCl and was extracted with EtOAc (2×50 ml). The extracts were dried ($MgSO_4$), filtered and concentrated in vacuo to give a yellow solid. Trituration with ethyl ether afforded the title compound as a white solid (3.80 g, 15.6 mmol, 84%); mp 139–141° C.

$^1$H NMR (400 MHz, $CDCl_3$) δ 8.70 (s, 1H), 8.10 (d, 1H), 7.15 (d, 1H), 4.40 (q, 2H), 3.05 (s, 3H), 1.60 (t, 3H). MS (TSP) m/z 262 ($MNH_4^+$). Anal. Calcd for $C_{10}H_{12}O_5S$: C, 49.17; H, 4.95. Found: C, 49.07; H, 4.90.

Preparation 4

3-Ethyl-1-(2-methoxyethyl)-4-nitro-1H-pyrazole-5-carboxamide and

Preparation 5

5-Ethyl-1-(2-methoxyethyl)-4-nitro-1H-pyrazole-3-carboxamide

A mixture of 3-ethyl-4-nitro-1H-pyrazole-5-carboxamide (1.62 g, 8.80 mmol, prepared using procedure in WO9849166), 2-bromoethyl methyl ether (1.23 g, 8.85 mmol) and cesium carbonate (2.90 g, 8.92 mmol) in N,N-dimethylformamide (20 ml) was stirred at 20° C. for 20 h. The reaction mixture was concentrated in vacuo and the residue was partitioned between EtOAc (125 ml) and brine (100 ml). The phases were separated, and the organic layer was dried ($Na_2SO_4$), filtered and concentrated in vacuo. The crude product was purified by column chromatography (EtOAc/MeOH, 97:3) to afford the title compound of preparation 4 (831 mg, 3.43 mmol, 39%).

$^1$H NMR (400 MHz, $d_6$-DMSO) δ 8.38 (s, 1H), 8.18 (s, 1H), 4.22 (t, 2H), 3.68 (t, 2H), 3.20 (s, 3H), 2.82 (q, 2H), 1.19 (t, 3H). MS m/z 260 ($MNH_4^+$)
and the title compound of preparation 5 (793 mg, 3.27, 37%).

$^1$H NMR (400 MHz, $CDCl_3$) δ 7.94 (s, 1H), 7.65 (s, 1H), 4.28 (t, 2H), 3.70 (t, 2H), 3.22 (s, 3H), 2.98 (q, 2H), 1.18 (t, 3H). MS m/z 243 ($MH^+$).

Preparation 6

4-amino-5-ethyl-1-(2-methoxyethyl)-1H-pyrazole-3-carboxamide

A mixture of the title compound from preparation 5 (500 mg, 2.07 mmol) and 10% palladium on charcoal (50 mg) in ethanol (20 ml) was hydrogenated at 50 psi and 20° C. for 18 h. The reaction mixture was filtered through Arbocel®, and the filtrate was concentrated in vacuo to afford the title compound as a white solid (395 mg, 1.86 mmol, 90%).

$^1$H NMR (400 MHz, $d_6$-DMSO) δ 7.01 (s, 1H), 6.90 (s, 1H), 4.39 (s, 2H), 4.09 (t, 2H), 3.63 (t, 2H), 3.20 (s, 3H), 2.57 (q, 2H), 1.03 (t, 3H). MS m/z 213 ($MH^+$).

Preparation 7

4-{[2-Ethoxy-5-(methylsulfonyl)benzoyl]amino}-5-ethyl-1-(2-methoxyethyl)-1H-pyrazole-3-carboxamide A mixture of the title compound of preparation 3 (244 mg, 1.00 mmol), the title compound from preparation 6 (212 mg, 1.00 mmol), 1-hydroxybenzotriazole hydrate (135 mg, 1.00 mmol), 1-(3-dimethylaminopropyl)-3-ethylcarbodiimide hydrochloride (192 mg, 1.00 mmol) and Et$_3$N (101 mg, 1.00 mmol) in DCM (10 ml) was stirred at 20° C. for 18 h. Further DCM (10 ml) and water (10 ml) was added, the mixture was shaken and the layers separated. The organic phase was dried (MgSO$_4$), filtered and concentrated in vacuo. The residue was triturated with EtOAc to afford the title compound as a white solid (260 mg, 0.59 mmol, 59%); mp 190–192° C.

$^1$H NMR (400 MHz, d$_6$-DMSO) δ 10.10 (s, 1H), 8.30 (s, 1H), 8.00 (d, 1H), 7.40 (d, 1H), 7.35 (s, 1H), 7.25 (s, 1H), 4.35 (q, 2H), 4.20 (t, 2H), 3.70 (t, 2H), 3.20 (s, 3H), 3.15 (s, 3H), 2.70 (q, 2H), 1.40 (t, 3H), 1.05 (t, 3H). MS (TSP) m/z 439 (MH$^+$). High resolution MS m/z calcd for C$_{19}$H$_{27}$N$_4$O$_6$S: 439.1646; found: 439.1644 (MH$^+$).

Preparation 8

Methyl 2-isobutoxy-5-(methylsulfonyl)benzoate

Cesium carbonate (12.4 g, 38.1 mmol) was added to a solution of the title compound of preparation 1 (6.00 g, 25.2 mmol) in MeCN (200 ml) and the mixture was stirred at 20° C. for 1 h. 1-Iodo-2-methylpropane (15.1 g, 82.0 mmol) was added and the mixture was heated to reflux for 18 h. The mixture was filtered and the filtrate was concentrated in vacuo. DCM (200 ml) and water (150 ml) were added and the mixture was shaken. The organic phase was dried (Na$_2$SO$_4$), filtered and concentrated in vacuo to afford the title compound as a white solid (6.85 g, 23.9 mmol, 95%); mp 76–81° C.

$^1$H NMR (300 MHz, CDCl$_3$) δ 8.40 (s, 1H), 8.00 (d, 1H), 7.10 (d, 1H), 3.95 (s, 3H), 3.90 (d, 2H), 3.05 (s, 3H), 2.20 (nonet, 1H), 1.10 (d, 6H). MS (TSP) m/z 304 (MNH$_4^+$). Anal. Calcd for C$_{13}$H$_{18}$O$_5$S.0.2H$_2$O: C, 53.85; H, 6.40. Found: C, 54.06; H, 6.26.

Preparation 9

2-Isobutoxy-5-(methylsulfonyl)benzoic acid

Prepared in 81% yield from the title compound of preparation 8 by following the same method used to produce the title compound of preparation 3; mp 149–153° C.

$^1$H NMR (300 MHz, CDCl$_3$) δ 8.70 (s, 1H), 8.10 (d, 1H), 7.20 (d, 1H), 4.10 (d, 2H), 3.10 (s, 3H), 2.30 (nonet, 1H), 1.15 (d, 6H). MS (TSP) m/z 290 (MH$^+$). Anal. Calcd for C$_{12}$H$_{16}$O$_5$S.0.125H$_2$O: C, 52.49; H. 5.97. Found: C, 52.35; H, 5.82.

Preparation 10

3-Ethyl-4-{[2-isobutoxy-5-(methylsulfonyl)benzoyl]amino}-1-(2-pyridinylmethyl)-1H-pyrazole-5-carboxamide Prepared in 59% yield by reacting the title compound of preparation 9 with 4-amino-3-ethyl-1-(2-pyridinylmethyl)-1H-pyrazole-5-carboxamide (prepared using the procedure in WO9954333) using the same method used to prepare the title compound of preparation 7; mp 225–227° C.

$^1$H NMR (300 MHz, CDCl$_3$) δ 9.70 (br s, 1H), 9.45 (br s, 1H), 8.80 (s, 1H), 8.55 (d, 1H), 8.05 (d, 1H), 7.75 (t, 1H), 7.40 (d, 1H), 7.30 (obscured, 1H), 7.20 (d, 1H), 5.70 (brs, 1H), 5.60 (s, 2H), 4.10 (d, 2H), 3.10 (s, 3H), 2.70 (q, 2H), 2.40 (nonet, 1H), 1.20 (t, 3H), 1.10 (d, 6H). MS (TSP) m/z 500 (MH$^+$). Anal. Calcd for C$_{24}$H$_{29}$N$_5$O$_5$S: C, 57.69; H, 5.85; N, 14.02. Found: C, 57.64; H, 5.82; N, 14.03.

Preparation 11

Methyl 2-(2-methoxyethoxy)-5-(methylsulfonyl)benzoate

A mixture of the title compound of preparation 1 (2.00 g, 8.69 mmol), 1-bromo-2-methoxyethane (2.55 g, 18.4 mmol) and K$_2$CO$_3$ (1.44 g, 10.4 mmol) in MeCN (30 ml) was heated at 70° C. for 4 days. The mixture was filtered and the filtrate concentrated in vacuo. The crude product was purified by column chromatography (100% DCM) to afford the title compound (2.33 g, 8.09 mmol, 93%).

$^1$H NMR (300 MHz, CDCl$_3$) δ 8.35 (s, 1H), 8.00 (d, 1H), 7.15 (d, 1H), 4.30 (t, 2H), 3.90 (s, 3H), 3.80 (t, 2H), 3.45 (s, 3H), 3.05 (s, 3H). MS (ES+) m/z 306 (MNH$_4^+$), 289 (MH$^+$). Anal. Calcd for C$_{12}$H$_{16}$O$_6$S.0.15H$_2$O: C, 49.53; H, 5.65. Found: C, 49.49; H, 5.47.

Preparation 12

2-(2-Methoxyethoxy)-5-(methylsulfonyl)benzoic acid

Prepared from the title compound of preparation 12 by following the same method used to produce the title compound of preparation 3, in 86% yield;

$^1$H NMR (300 MHz, CD$_3$OD) δ 8.30 (s, 1H), 8.05 (d, 1H), 7.35 (d, 1H), 4.35 (t, 2H), 3.90 (t, 2H), 3.45 (s, 3H), 3.10 (s, 3H). MS (ES+) m/z 292 (MNH$_4^+$), 275 (MH$^+$). Anal. Calcd for C$_{11}$H$_{14}$O$_6$S: C, 48.16; H, 5.14. Found: C, 47.83; H, 5.08.

Preparation 13

3-Ethyl-4-{[2-(2-methoxyethoxy)-5-(methylsulfonyl)benzoyl]amino-}-1-(2-pyridinylmethyl)-1H-pyrazole-5-carboxamide Prepared by reacting the title compound of preparation 12 with 4-amino-3-ethyl-1-(2-pyridinylmethyl)-1H-pyrazole-5-carboxamide (prepared using the procedure in WO9954333) using the same method used to prepare the title compound of preparation 7, in 44% yield.

$^1$H NMR (300 MHz, CDCl$_3$) δ 9.80 (br s, 1H), 8.85 (br s, 1H), 8.80 (s, 1H), 8.50 (br m, 1H), 8.05 (d, 1H), 7.70 (t, 1H), 7.20 (three obscured multiplets, 3H), 5.65 (s, 2H), 4.45 (br m, 2H), 3.90 (br m, 2H), 3.35 (s, 3H), 3.05 (s, 3H), 2.65 (q, 2H), 1.20 (t, 3H). MS (ES+) m/z 502 (MH$^+$).

Preparation 14

Methyl 2-butoxy-5-(methylsulfonyl)benzoate

Prepared in 94% yield by following an analogous procedure used for the synthesis of the title compound of preparation 11, but using iodobutane as the alkylating agent.

$^1$H NMR (300 MHz, CDCl$_3$) δ 8.35 (s, 1H), 8.00 (d, 1H), 7.05 (d, 1H), 4.15 (t, 2H), 3.90 (s, 3H), 3.05 (s, 3H), 1.85 (quintet, 2H), 1.55 (sextet, 2H), 1.00 (t, 3H) MS (ES+) m/z 304 (MNH$_4^+$), 287 (MH$^+$). Anal. Calcd for C$_{13}$H$_{18}$O$_5$S: C, 54.53; H, 6.34. Found: C, 54.31; H, 6.33.

Preparation 15

2-Butoxy-5-(methylsulfonyl)benzoic acid

Prepared in 93% yield from the title compound of preparation 14 by following the same method used to produce the title compound of preparation 3.

¹H NMR (300 MHz, CD₃OD) δ 8.30 (s, 1H), 8.05 (d, 1H), 7.30 (d, 1H), 4.20 (t, 2H), 3.10 (s, 3H), 1.85 (quintet 2H), 1.55 (hextet, 2H), 1.00 (t, 3H). MS (ES+) m/z 290 (MNH₄⁺), 273 (MH⁺). Anal. Calcd for $C_{12}H_{16}O_5S$: C, 52.93; H, 5.92. Found: C, 52.67; H, 5.85.

Preparation 16

4-{[2-Butoxy-5-(methylsulfonyl)benzoyl]amino}-3-ethyl-1-(2-pyridinylmethyl)-1H-pyrazole-5-carboxamide Prepared in 60% yield by reacting the title compound of preparation 15 with 4-amino-3-ethyl-1-(2-pyridinylmethyl)-1H-pyrazole-5-carboxamide (prepared using the procedure in WO9954333) using the same method used to prepare the title compound of preparation 7.

¹H NMR (300 MHz, CDCl₃) δ 9.80 (br s, 1H), 9.45 (br s, 1H), 8.80 (s, 1H), 8.55 (br m, 1H), 8.05 (d, 1H), 7.75 (t, 1H), 7.40 (d, 1H), 7.25 (obscured multiplet, 1H), 7.20 (d, 1H), 5.70 (br s, 1H), 5.60 (s, 2H), 4.35 (t, 2H), 3.05 (s, 3H), 2.70 (q, 2H), 2.00 (quintet, 2H), 1.55 (sextet, 2H), 1.20 (t, 3H), 1.00 (t, 3H). MS (ES+) m/z 500 (MH⁺).

Preparation 17

Methyl 5-(methylsulfonyl)-2-(2-pyridinylmethoxy)benzoate

Prepared in 22% yield by following an analogous procedure used for the synthesis of the title compound of preparation 11, but using 2-(bromomethyl)pyridine hydrobromide as the alkylating agent; mp 189–192° C.

¹H NMR (400 MHz, d₆-DMSO) δ 8.55 (d, 1H), 8.20 (s, 1H), 8.05 (d, 1H), 7.85 (t, 1H), 7.60 (d, 1H), 7.50 (d, 1H), 7.35 (t, 1H), 5.40 (s, 2H), 3.85 (s, 3H) (s, 3H). MS (TSP) m/z 322 (MH⁺). Anal. Calcd for $C_{15}H_{15}NO_5S$: C, 56.06; H, 4.71; N, 4.36. Found: C, 55.89; H, 4.59; N, 4.38.

Preparation 18

5-(Methylsulfonyl)-2-(2-pyridinylmethoxy)benzoic acid

Prepared in 78% yield from the title compound of preparation 17 by following the same method used to produce the title compound of preparation 3.

¹H NMR (300 MHz, d₆-DMSO) δ 8.55 (d, 1H), 7.80 (two obscured multiplets, 2H), 7.70 (d, 1H), 7.65 (d, 1H), 7.30 (t, 1H), 7.15 (d, 1H), 5.25 (s, 2H), 3.10 (s, 3H).

Preparation 19

3-Ethyl-4-{[5-(methylsulfonyl)-2-(2-pyridinylmethoxy)benzoyl]amino}-1H-pyrazole-5-carboxamide Prepared in 50% yield by reacting the title compound of preparation 18 with 4-amino-3-ethyl-1H-pyrazole-5-carboxamide (prepared using the procedure in WO9849166) using the same method used to prepare the title compound of preparation 7; mp 134–138° C.

¹H NMR (300 MHz, d₆-DMSO) δ 13.00 (br s, 1H), 10.60 (br s, 1H), 8.55 (br s, 1H), 8.40 (br s, 1H), 8.00 (d, 1H), 7.80 (t, 1H), 7.60 (d, 1H), 7.40–7.50 (two multiplets, 2H), 7.35 (br m, 1H), 7.25 (br m, 1H), 5.60 (s, 2H), 3.20 (s, 3H), 2.75 (q, 2H), 1.15 (t, 3H). Anal. Calcd for $C_{20}H_{21}N_5O_5S \cdot 1.0$ EtOAc: C, 54.22; H, 5.50; N, 13.18. Found: C, 53.92; H, 5.50; N, 13.11.

Preparation 20

3-Ethyl-4-{[2-isobutoxy-5-(methylsulfonyl)benzoyl]amino}-1-1-[(1-methyl-1H imidazol-2-yl)methyl]1H-pyrazole-5-carboxamide Prepared in 55% yield by reacting the title compound of preparation 9 with 4-amino-3-ethyl-1-[(1-methyl-1H-imidazol-2-yl)methyl]-1H-pyrazole-5-carboxamide (prepared using the procedure in WO9954333) using the same method used to prepare the title compound of preparation 7; mp 207–214° C.

¹H NMR (400 MHz, d₆-DMSO) δ 9.55 (s, 1H), 8.10 (s, 1H), 7.95 (d, 1H), 7.85 (br s, 1H), 7.75 (br s, 1H), 7.40 (d, 1H), 7.00 (s, 1H), 6.75 (s, 1H), 5.55 (s 4.00 (d, 2H), 3.70 (s, 3H), 3.15 (s, 3H), 2.40 (obscured multiplet, 2H), 2.10 (nonet, 1H), 1.05 (t, 3H), 0.95 (d, 6H). MS (TSP) m/z 503 (MH⁺). Anal. Calcd for $C_{23}H_{30}N_6O_5S \cdot 0.1H_2O$: C, 54.76; H, 6.04; N, 16.66. Found: C, 54.37; H, 6.19; N, 17.06.

Preparation 21

3-Ethyl-1-[2-(4-morpholinyl)ethyl]-4-nitro-1H-pyrazole-5-carboxamide and

Preparation 22

5-Ethyl-1-[2-(4-morpholinyl)ethyl]-4-nitro-1H-pyrazole-3-carboxamide

A mixture of 3-ethyl-4-nitro-1H-pyrazole-5-carboxamide (20.0 g, 109 mmol, prepared using procedure in WO9849166), 4-(2-chloroethyl)morpholine hydrochloride (22.2 g, 120 mmol), $K_2CO_3$ (29.9 g, 217 mmol) and cesium carbonate (7.08 g, 21.7 mmol) in N,N-dimethylformamide (100 ml) was stirred at 55° C. for 18 h. The reaction mixture was concentrated in vacuo and the residue was partitioned between EtOAc (350 ml) and water (500 ml). The phases were separated, and the aqueous layer extracted with further EtOAc (150 ml). The organic phases were combined, dried ($Na_2SO_4$), filtered and concentrated in vacuo. The crude product was purified by column chromatography (EtOAc/MeOH, 100:0–80:20, followed by EtOAc/MeOH/NH₃, 80:20:1) to afford the title compound of preparation 21 (16.21 g, 54.5 mmol, 50%); mp 132–133° C.

¹H NMR (400 MHz, CDCl₃) δ 7.60 (br s, 1H), 6.40 (br s, 1H), 4.45 (t, 2H), 3.60 (m, 4H), 2.90 (q, 2H), 2.75 (t, 2H), 2.45 (m, 4H), 1.25 (t, 3H). MS (TSP) m/z 298 (MH⁺). Anal. Calcd for $C_{12}H_{19}N_5O_4$: C, 48.48; H, 6.44; N, 23.56. Found: C, 48.44; H, 6.46; N, 23.48. and the title compound of preparation 22 (7.83 g, 26.3 mmol, 24%); 145–147° C. Note the regioisomers were assigned on the basis on nOe studies.

¹H NMR (400 MHz, CDCl₃) δ 7.20 (br s, 1H), 6.00 (br s, 1H), 4.20 (t, 2H), 3.65 (m, 4H), 3.00 (q, 2H), 2.85 (t, 2H), 2.50 (m, 4H), 1.30 (t, 3H). MS (TSP) m/z 298 (MH⁺). Anal. Calcd for $C_{12}H_{19}N_5O_4$: C, 48.48; H, 6.44; N, 23.56. Found: C, 48.46; H, 6.45; N, 23.33.

Preparation 23

4-Amino-5-ethyl-1-[2-(4-morpholinyl)ethyl]-1H-pyrazole-3-carboxamide

White crystals of the title compound were formed in 91% yield from the title compound of preparation 22 by using the same method used to prepare the title compound of preparation 6; mp 152–153° C.

¹H NMR (400 MHz, CDCl₃) δ 6.55 (br s, 1H), 5.20 (br s, 1H), 4.05 (t, 2H), 3.90 (s, 2H), 3.65 (m, 4H), 2.75 (t, 2H), 2.60 (q, 2H), 2.45 (m, 4H), 1.20 (t, 3H) MS (TSP) m/z 268 (MH$^+$). Anal. Calcd for $C_{12}H_{21}N_5O_2$: C, 53.92; H, 7.98; N, 26.20. Found: C, 53.73; H, 8.01; N, 25.85.

Preparation 24

4-{[2-Butoxy-5-(methylsulfonyl)benzoyl]amino}-5-ethyl-1-[2-(4-morpholinyl)ethyl]-1H-pyrazole-3-carboxamide Prepared in 67% yield by reacting the title compound of preparation 23 with the title compound of preparation 15 using the same method used to prepare the title compound of preparation 7; mp 182–185° C.

$^1$H NMR (400 MHz, d$_6$-DMSO) δ 10.00 (s, 1H), 8.30 (s, 1H), 8.00 (d, 1H), 7.40 (d, 1H), 7.30 (br s, 1H), 7.20 (br s, 1H), 4.25 (t, 2H), 4.15 (t, 2H), 3.50 (m, 4H), 3.15 (s, 3H), 2.70 (two multiplets, 4H), 2.45 (m, 4H), 1.80 (quintet, 2H), 1.40 (sextet, 2H), 1.05 (t, 3H), 0.85 (t, 3H). MS (TSP) m/z 522 (MH$^+$). Anal. Calcd for $C_{24}H_{35}N_5O_6S.0.25H_2O$: C, 54.78; H, 6.80; N, 13.31. Found: C, 54.62; H, 6.91; N, 13.36.

Preparation 25

5-Ethyl-4-{[2-isobutoxy-5-(methylsulfonyl)benzoyl]amino}-1-[(1-methyl-1H-imidazol-2-yl)methyl]-1H-pyrazole-3-carboxamide Prepared in 66% yield by reacting the title compound of preparation 9 with 4-amino-5-ethyl-1-[(1-methyl-1H-imidazol-2-yl)methyl]-1H-pyrazole-3-carboxamide (prepared using the procedure in WO9954333) using the same method used to prepare the title compound of preparation 7; mp 201–206° C.

$^1$H NMR (400 MHz, d$_6$-DMSO) δ 9.85 (s, 1H), 8.25 (s, 1H), 8.00 (d, 1H), 7.40 (d, 1H), 7.30 (brs, 1H), 7.20 (brs, 1H), 7.10 (s, 1H), 6.80 (s, 1H), 5.40 (s, 2H), 4.00 (d, 2H), 3.70 (s, 3H), 3.15 (s, 3H), 2.80 (q, 2H), 2.15 (nonet, 1H), 1.00 (t, 3H), 0.90 (d, 6H). MS (TSP) m/z 503 (MH$^+$). Anal. Calcd for $C_{23}H_{30}N_6O_5S.0.5H_2O$: C, 53.99; H, 6.11; N, 16.43. Found: C, 53.64; H, 6.20; N, 16.59.

Preparation 26

5-Ethyl-4-{[2-isobutoxy-5-(methylsulfonyl)benzoyl]amino}-1-[2-(4-morpholinyl)ethyl]-1H-pyrazole-3-carboxamide Prepared in 68% yield by reacting the title compound of preparation 9 with the title compound of preparation 23 using the same method used to prepare the title compound of preparation 7; mp 200–203° C.

$^1$H NMR (400 MHz, d$_6$-DMSO) δ 9.85 (s, 1H), 8.25 (s, 1H), 8.00 (d, 1H), 7.40 (d, 1H), 7.30 (br s, 1H), 7.20 (br s, 1H), 4.15 (t, 2H), 4.00 (d, 2H), 3.50 (m, 4H), 3.15 (s, 3H), 2.70 (two multiplets, 4H), 2.40 (m, 4H), 2.15 (nonet, 1H), 1.05 (t, 3H), 0.90 (d, 6H). MS (TSP) m/z 522 (MH$^+$). Anal. Calcd for $C_{24}H_{35}N_5O_6S.0.5H_2O$: C, 54.32; H, 6.84; N, 13.20. Found: C, 54.20; H, 7.00; N, 13.33.

Preparation 27

Methyl 5-(methylsulfonyl)-2-propoxybenzoate

Prepared in 76% yield by following an analogous procedure used for the synthesis of the title compound of preparation 11, but using 1-bromopropane as the alkylating agent.

$^1$H NMR (300 MHz, CDCl$_3$) δ 8.35 (s, 1H), 8.00 (d, 1H), 7.10 (d, 1H), 4.10 (t, 2H), 3.95 (s, 3H), 3.05 (s, 3H), 1.90 (sextet, 2H), 1.10 (t, 3H). MS (TSP) m/z 290 (MNH$_4^+$), 273 (MH$^+$).

Preparation 28

5-(Methylsulfonyl)-2-propoxybenzoic acid

Prepared in 73% yield from the title compound of preparation 27 by following the same method used to produce the title compound of preparation 3; mp 148–152° C.

$^1$H NMR (400 MHz, CDCl$_3$) δ 8.70 (s, 1H), 8.10 (d, 1H), 7.20 (d, 1H), 4.30 (t, 2H), 3.05 (s, 3H), 2.00 (sextet, 2H), 1.15 (t, 3H). MS (ES+) m/z 281 (MNa$^+$). Anal. Calcd for $C_{11}H_{14}O_5S.0.1H_2O$: C, 50.80; H, 5.50. Found: C, 50.74; H, 5.38.

Preparation 29

3-Ethyl-4-{[5-(methylsulfonyl)-2-propoxybenzoyl]amino}-1-(2-pyridinylmethyl)-1H-pyrazole-5-carboxamide Prepared in 69% yield by reacting the title compound of preparation 28 with 4-amino-3-ethyl-1-(2-pyridinylmethyl)-1H-pyrazole-5-carboxamide (prepared using the procedure in WO9954333) using the same method used to prepare the title compound of preparation 7.

$^1$H NMR (300 MHz, CDCl$_3$) δ 9.80 (s, 1H), 9.50 (br s, 1H), 8.80 (s, 1H), 8.55 (d, 1H), 8.05 (d, 1H), 7.75 (t, 1H), 7.40 (d, 1H), 7.30 (obscured, 1H), 7.20 (d, 1H), 5.70 (br s, 1H), 5.60 (s, 2H), 4.30 (t, 2H), 3.10 (s, 3H), 2.70 (q, 2H), 2.10 (sextet, 2H), 1.20 (t, 3H), 1.10 (t, 3H). MS (TSP) m/z 486 (MH$^+$). Anal. Calcd for $C_{23}H_{27}N_5O_5S.0.2H_2O$: C, 56.47; H, 5.65; N, 14.32. Found: C, 56.37; H, 5.59; N, 14.37.

Preparation 30

1-(Cyclopropylmethyl)-3-ethyl-4-nitro-1H-pyrazole-5-carboxamide and

Preparation 31

1-(Cyclopropylmethyl)-5-ethyl-4-nitro-1H-pyrazole-3-carboxamide

A suspension of 3-ethyl-4-nitro-1H-pyrazole-5-carboxamide (40.0 g, 217 mmol, prepared using procedure in WO9849166) in dry DMF (300 ml) was treated with cesium carbonate (77.8 g, 239 mmol). To this, in a single portion, was added cyclopropylmethyl bromide (32.2 g, 239 mmol) and the resultant suspension stirred at 20° C. for 6 h. After concentrating in vacuo, the residue was partitioned between EtOAc (200 ml) and water (200 ml), and the insoluble material removed by filtration. The solid was partitioned between water (200 ml) and DCM (200 ml), and undissolved solid removed by filtration. Combined organics were washed with brine (100 ml), dried (MgSO$_4$), filtered and concentrated in vacuo to a solid (~40 g). The two regioisomers were separated by crystallisation of the crude mixture. The more lipophilic component (Rf=0.27, DCM:MeOH 98:2) crystallised from a mixture of DCM (50 ml) and diisopropylether (200 ml) to give 1-(cyclopropylmethyl)-3-ethyl-4-nitro-1H-pyrazole-5-carboxamide (11.9 g, 50.0 mmol, 23%). Crystallisation of the mother liquors from MeCN gave the more polar component (Rf=0.19, DCM:MeOH 98:2) (10.0 g, 42.0 mmol) which was confirmed as 1-(cyclopropylmethyl)-5-ethyl-4-nitro-1H-pyrazole-3-carboxamide by nOe studies. The mother liquors contained further material as a mixture of regioisomers (20.0 g, 84.0 mmol). 1-(cyclopropylmethyl)-3-ethyl-4-nitro-1H-pyrazole-5-carboxamide:

$^1$H NMR (400 MHz, CDCl$_3$) δ 7.15 (br s, 1H), 6.00 (br s, 1H), 4.20 (d, 2H), 2.90 (q, 2H), 1.30 (m, 1H), 1.25 (t, 3H), 0.55 (m, 2H), 0.40 (m, 2H). MS (TSP) m/z 239 (MH$^+$). Anal. Calcd for $C_{10}H_{14}N_4O_3$: C, 50.41; H, 5.92; N, 23.52. Found C, 50.38; H, 5.93; N, 23.12.

1-(cyclopropylmethyl)-5-ethyl-4-nitro-1H-pyrazole-3-carboxamide $^1$H NMR (400 MHz, CDCl$_3$) δ 7.20 (br s, 1H), 5.85 (br s, 1H), 4.00 (d, 2H), 2.95 (q, 2H), 1.25 (obscured multiplet, 1H), 1.25 (t, 3H), 0.60 (m, 2H), 0.40 (m, 2H). MS (TSP) m/z 239 (MH$^+$). Anal. Calcd for $C_{10}H_{14}N_4O_3$: C, 50.41; H, 5.92; N, 23.52. Found C, 50.30; H, 5.90; N, 23.39.

Preparation 32

4-Amino-1-(cyclopropylmethyl)-5-ethyl-1H-pyrazole-3-carboxamide

Prepared in 92% yield from the title compound of preparation 31 using the method used to prepare the title compound of preparation 6; mp143–145° C.

$^1$H NMR (400 MHz, d$_6$-DMSO): δ 7.00 (br s, 1H), 6.90 (br s, 1H), 4.40 (br s, 2H), 3.80 (d, 2H), 2.50 (q, 2H), 1.10 (m, 1H), 1.00 (t, 3H), 0.40 (m, 2H), 0.03 (m, 2H). MS (TSP) m/z 209 (MH$^+$). Anal. Calcd for $C_{10}H_{16}N_4O$: C, 57.67; H, 7.74; N, 26.91. Found C, 57.58; H, 7.78; N, 26.76.

Preparation 33

1-(Cyclopropylmethyl)-5-ethyl-4-{[5-(methylsulfonyl)-2-propoxybenzoyl]amino}-1H-pyrazole-3-carboxamide Prepared in 26% yield by reacting the title compound of preparation 28 with the title compound of preparation 32 using the same method used to prepare the title compound of preparation 7; mp185–186° C.

$^1$H NMR (300 MHz, CDCl$_3$): δ 10.30 (brs, 1H), 8.80 (s, 1H), 8.05 (d, 1H), 7.15 (d, 1H), 6.70 (br s, 1H), 5.25 (br s, 1H), 4.30 (t, 2H), 4.00 (d, 2H), 3.10 (s, 3H), 2.95 (q, 2H), 2.05 (sextet, 2H), 1.30 (m, 1H), 1.20 (t, 3H), 1.10 (t, 3H), 0.65 (m, 2H), 0.45 (m, 2H). MS (TSP) m/z 449 (MH$^+$). Anal. Calcd for $C_{21}H_{28}N_4O_5S.0.2H_2O$: C, 55.79; H, 6.33; N, 12.39. Found C, 55.66; H, 6.33; N, 12.49.

Preparation 34 tert-Butyl (2S)-2-{[5-(aminocarbonyl)-3-ethyl-4-nitro-1H-pyrazol-1-yl]methyl}-1-pyrrolidinecarboxylate and

Preparation 35 tert-Butyl (2S)-2-{[3-(aminocarbonyl)-5-ethyl-4-nitro-1H-pyrazol-1-yl]methyl}-1-pyrrolidinecarboxylate A mixture of 3-ethyl-4-nitro-1H-pyrazole-5-carboxamide (8.20 g, 44.6 mmol, prepared using procedure in WO9849166), tert-butyl (2S)-2-({[(4-methylphenyl)sulfonyl]oxy}methyl)-1-pyrrolidinecarboxylate (17.4 g, 49.0 mmol, prepared using procedure in WO9926944) and cesium carbonate (16.0 g, 49.2 mmol) in N,N-dimethylformamide (100 ml) was stirred at 20° C. for 4 days and then at 50° C. for 18 h. The reaction mixture was concentrated in vacuo and the residue was partitioned between EtOAc (300 ml) and water (300 ml). The phases were separated, and the aqueous layer extracted with further EtOAc (2×200 ml). The organic phases were combined, dried (Na$_2$SO$_4$), filtered and concentrated in vacuo. The crude product was partially purified by column chromatography (DCM/MeOH, 100:0–91:9) and then the regioisomers were separated by further column chromatography (Et$_2$O/EtOAc, 100:0–50:50) to afford the title compound of preparation 34 (1.23 g, 3.35 mmol, 7.5%); mp 68–75° C.

$^1$H NMR (400 MHz, CDCl$_3$) δ 7.85 (br s, 1H), 5.90 (br s, 1H), 4.35 (m, 2H), 4.10 (m, 1H), 3.30 (m, 2H), 2.90 (q, 2H), 1.70–2.00 (two multiplets, 4H), 1.30 (s, 9H), 1.25 (t, 3H). MS (ES+) m/z 390 (MNa$^+$), 368 (MH$^+$). Anal. Calcd for $C_{16}H_{25}N_5O_5.0.15$ Et$_2$O: C, 52.29; H, 7.07; N, 18.25. Found: C, 52.29; H, 7.07; N, 18.26.

and the title compound of preparation 35 (5.32 g, 14.5 mmol, 33%).

$^1$H NMR (400 MHz, CDCl$_3$) δ 7.10 (br s, 1H), 6.25 (br s, 1H), 4.20–4.40 (m, 1H), 4.05 (m, 2H), 3.20–3.40 (m, 2H), 2.90–3.10 (m, 2H), 1.60–1.90 (two multiplets, 4H), 1.40 (s, 9H), 1.20 (t, 3H). MS (TSP) m/z 385 (MH$_4^+$), 368 (MH$^+$). Anal. Calcd for $C_{16}H_{25}N_5O_5$: C, 52.31; H, 6.86; N, 19.06. Found: C, 51.95; H, 6.92; N, 18.94.

Preparation 36

3-Ethyl-1-{[(2S)-1-methylpyrrolidinyl]methyl}-4-nitro-1H-pyrazole-5-carboxamide

HCl was bubbled through a solution of the title compound of preparation 34 (2.52 g, 6.87 mmol) in EtOAc (100 ml) at 0° C. for 10 min. The solution was stirred at 0° C. for 90 min and then concentrated in vacuo. DCM (150 ml) and 10% Na$_2$CO$_3$ (150 ml) were added, and the mixture was shaken. The organic phase was dried (Na$_2$SO$_4$), filtered and concentrated in vacuo to give a crude sample of 3-ethyl-4-nitro-1-[(2S)-pyrrolidinylmethyl]-1H-pyrazole-5-carboxamide (1.21 g, ~4.5 mmol) as a viscous yellow oil. This was dissolved in DCM (100 ml) and 37% aqueous solution of formaldehyde (0.91 ml, 13.5 mmol) was added. NaBH(OAc)$_3$ (2.39 g, 11.3 mmol) was added and the mixture was stirred at 20° C. for 75 min. DCM (150 ml) and sat. NaHCO$_3$ (150 ml) were added and the mixture shaken. The aqueous phase was further extracted with DCM (50 ml), and the combined organic phases were washed with brine (50 ml), dried (Na$_2$SO$_4$), filtered and concentrated in vacuo. The crude product was purified by column chromatography (DCM/MeOH, 98:2–90:10) to afford the title compound as a white solid (349 mg, 1.24 mmol, 18%); mp 148–150° C.

$^1$H NMR (400 MHz, CDCl$_3$) δ 9.20 (br s, 1H), 6.20 (br s, 1H), 4.20 (dd, 1H), 4.10 (dd, 1H), 3.00 (m, 2H), 2.90 (q, 2H), 2.35 (m, 1H), 2.00 (s, 3H), 2.00 (obscured multiplet, 1H), 1.80 (m, 1H), 1.60 (m, 2H), 1.25 (t, 3H). MS (TSP) m/z 282 (MH$^+$). Anal. Calcd for $C_{12}H_{19}N_5O_3.0.1H_2O$: C, 50.91; H, 6.84; N, 24.74. Found: C, 51.01; H, 6.82; N, 24.45.

Preparation 37

4-Amino-3-ethyl-1-{[(2S)-1-methylpyrrolidinyl]methyl}-1H-pyrazole-5-carboxamide

Prepared in 83% yield from the title compound of preparation 36 using the method used to prepare the title compound of preparation 6.

$^1$H NMR (400 MHz, CDCl$_3$) δ 4.20 (dd, 1H), 4.10 (dd, 1H), 3.80 (br s, 2H), 3.05 (m, 1H), 3.00 (m, 1H), 2.50 (q, 2H), 2.30 (m, 1H), 2.00 (s, 3H), 1.60–1.80 (m, 4H), 1.20 (t, 3H). MS (TSP) m/z 252 (MH$^+$).

Preparation 38 tert-Butyl (2R)-2-{[5-(aminocarbonyl)-3-ethyl-4-nitro-1H-pyrazol-1-yl]methyl}-1-pyrrolidinecarboxylate and

Preparation 39 tert-Butyl (2R)-2-{[3-(aminocarbonyl)-5-ethyl-4-nitro-1H-pyrazol-1-yl]methyl}-1-pyrrolidinecarboxylate Prepared from 3-ethyl-4-nitro-1H-pyrazole-5-carboxamide (prepared using procedure in WO9849166)

and tert-butyl (2R)-2-({[(4-methylphenyl)sulfonyl]oxy}methyl)-1-pyrrolidinecarboxylate (prepared using procedure in WO9926944) by following the method used for the synthesis of the title compounds of preparations 34 and 35.

tert-Butyl (2R)-2-{[5-(aminocarbonyl)-3-ethyl-4-nitro-1H-pyrazol-1-yl]methyl}-1-pyrrolidinecarboxylate was obtained in 14% yield:

$^1$H NMR (400 MHz, CDCl$_3$) δ 7.85 (br s, 1H), 6.10 (br s, 1H), 4.35 (m, 2H), 4.10 (m, 1H), 3.30 (m, 2H), 2.90 (m, 2H), 1.70–2.00 (two multiplets, 4H), 1.30 (s, 9H), 1.25 (t, 3H). MS (ES+) m/z 390 (MNa$^+$), 368 (MH$^+$). Anal. Calcd for C$_{16}$H$_{25}$N$_5$O$_5$.0.25 Et$_2$O.0.25H$_2$O: C, 52.30; H, 7.23; N, 17.94. Found: C, 52.49; H, 7.14; N, 17.60.

tert-Butyl (2R)-2-{[3-(aminocarbonyl)-5-ethyl-4-nitro-1H-pyrazol-1-yl]methyl}-1-pyrrolidinecarboxylate was obtained in 28% yield:

$^1$H NMR (400 MHz, CDCl$_3$) δ 7.10 (br s, 1H), 6.60 (br s, 1H), 4.20–4.40 (m, 1H), 4.05 (m, 2H), 3.20–3.40 (m, 2H), 2.90–3.10 (m, 2H), 1.60–1.90 (two multiplets, 4H), 1.40 (s, 9H), 1.20 (t, 3H). MS (ES+) m/z 390 (MNa$^+$), 368 (MH$^+$). Anal. Calcd for C$_{16}$H$_{25}$N$_5$O$_5$.0.2H$_2$O.0.2EtOAc: C, 51.92; H, 7.00; N, 18.02. Found: C, 51.60; H, 7.05; N, 18.10.

Preparation 40

5-Ethyl-4-nitro-1-[(2R)-pyrrolidinylmethyl]-1H-pyrazole-3-carboxamide

HCl was bubbled through a solution of the title compound of preparation 39 (4.03 g, 11.0 mmol) in EtOAc (150 ml) at 0° C. for 10 min. The solution was stirred at 0° C. for 60 min and then concentrated in vacuo. DCM (150 ml) and 10% Na$_2$CO$_3$ (150 ml) were added, and the mixture was shaken. After separation the aqueous phase was extracted with DCM (50 ml). The organic phases were combined, dried (Na$_2$SO$_4$), filtered and concentrated in vacuo to afford the title compound as a crystalline solid (1.78 g, 6.64 mmol, 61%); mp 151–153° C.

$^1$H NMR (400 MHz, CDCl$_3$) δ 7.20 (br s, 1H), 6.15 (br s, 1H), 4.05 (dd, 1H), 3.90 (dd, 1H), 3.70 (m, 1H), 3.00 (m, 2H), 2.90 (m, 2H), 1.90 (m, 1H), 1.65–1.85 (m, 2H), 1.45 (m, 1H), 1.25 (t, 3H). MS (TSP) m/z 268 (MH$^+$).

Preparation 41

5-Ethyl-1-{[(2R)-1-methylpyrrolidinyl]methyl}-4-nitro-1H-pyrazole-3-carboxamide

Formaldehyde (37% aqueous solution, 1.60 ml, 19.8 mmol) was added to a solution of the title compound of preparation 40 (1.78 g, 6.64 mmol) in DCM (75 ml) and stirred at 20° C. for 15 min. NaBH(OAc)$_3$ (3.49 g, 16.5 mmol) was added and the mixture stirred for a further 4 h. DCM (75 ml) and sat. NaHCO$_3$ (100 ml) were added and the mixture shaken. After separation the aqueous phase was extracted with DCM (50 ml). The organic phases were combined, washed with brine (50 ml), dried (Na$_2$SO$_4$) and concentrated in vacuo. The crude product was purified by column chromatography (DCM/MeOH, 96:4–90:10) to afford the title compound as a cream solid (1.35 g, 4.80 mmol, 73%); mp 111–116° C.

$^1$H NMR (400 MHz, CDCl$_3$) δ 7.15 (br s, 1H), 6.30 (br s, 1H), 4.10 (dd, 1H), 4.00 (dd, 1H), 3.00 (m, 3H), 2.90 (m, 1H), 2.25 (q, 1H), 2.20 (s, 3H), 1.85 (m, 1H), 1.55–1.70 (m, 3H), 1.20 (t, 3H). MS (TSP) m/z 282 (MH$^+$).

Preparation 42

4-Amino-5-ethyl-1-{[(2R)-1-methylpyrrolidinyl]methyl}-1H-pyrazole-3-carboxamide

Prepared in 83% yield from the title compound of preparation 41 using the method used to prepare the title compound of preparation 6; mp 130–133° C.

$^1$H NMR (400 MHz, CDCl$_3$) δ 6.60 (br s, 1H), 5.20 (br s, 1H), 4.05 (dd, 1H), 3.95 (br s, 2H), 3.85 (dd, 1H), 3.10 (m, 1H), 2.70 (m, 1H), 2.60 (q, 2H), 2.20 (obscured multiplet, 1H), 2.20 (s, 3H), 1.60–1.90 (m, 4H), 1.20 (t, 3H). MS (TSP) m/z 252 (MH$^+$). Anal. Calcd for C$_{12}$H$_{21}$N$_5$O.0.2H$_2$O: C, 56.54; H, 8.46; N, 27.47. Found: C, 56.86; H, 8.42; N, 27.41.

Preparation 43

3-Ethyl-4-nitro-1-(3-pyridazinylmethyl)-1H-pyrazole-5-carboxamide and

Preparation 44

5-Ethyl-4-nitro-1-(3-pyridazinylmethyl)-1H-pyrazole-3-carboxamide

A mixture of 3-ethyl-4-nitro-1H-pyrazole-5-carboxamide (15.7 g, 85.6 mmol, prepared using procedure in WO9849166), 3-(chloromethyl)pyridazine (11.0 g, 85.6 mmol, prepared using procedure in WO0023449) and cesium carbonate (27.8 g, 85.6 mmol) in N,N-dimethylformamide (200 ml) was stirred at 20° C. for 18 h. The reaction mixture was concentrated in vacuo and the residue was partitioned between DCM (200 ml) and 10% aqueous Na$_2$CO$_3$ (100 ml). The phases were separated, and the aqueous layer extracted with further DCM (6×50 ml). The organic phases were combined, dried (Na$_2$SO$_4$), filtered and concentrated in vacuo. The crude product was purified by column chromatography (EtOAc/MeOH, 95:5–9010) to afford the title compound of preparation 43 (Note, the regioisomers were assigned on the basis of nOe experiments) (4.09 g, 14.8 mmol, 17%):

$^1$H NMR (400 MHz, d$_6$-DMSO) δ 9.20 (d, 1H), 8.50 (br s, 1H), 8.20 (br s, 1H), 7.70 (m, 1H), 7.55 (d, 1H), 5.65 (s, 2H), 2.85 (q, 2H), 1.20 (t, 3H). MS (ES+) m/z 299 (MNa$^+$), 277 (MH$^+$). Anal. Calcd for C$_{11}$H$_{12}$N$_6$O$_3$: C, 47.82; H, 4.38; N, 30.42. Found: C, 47.71; H, 4.31; N, 30.24.

and the title compound of preparation 44 (8.00 g, 29.0 mmol, 34%):

$^1$H NMR (400 MHz, d$_6$-DMSO) δ 9.20 (d, 1H), 8.00 (br s, 1H), 7.70 (m, 2H), 7.65 (d, 1H), 5.80 (s, 2H), 3.05 (q, 2H), 1.10 (t, 3H). MS (ES+) m/z 299 (MNa$^+$), 277 (MH$^+$). Anal. Calcd for C$_{11}$H$_{12}$N$_6$O$_3$: C, 47.82; H, 4.38; N, 30.42. Found: C, 47.70; H, 4.31; N, 30.13.

Preparation 45

4-Amino-5-ethyl-1-(3-pyridazinylmethyl)-1H-pyrazole-3-carboxamide

The title compound was formed as a cream coloured solid in 34% yield from the title compound of preparation 44 by following the method used to prepare the title compound of preparation 6; mp 177–185° C.

$^1$H NMR (400 MHz, d$_6$-DMSO) δ 9.20 (d, 1H), 7.65 (m, 1H), 7.25 (d, 1H), 7.15 (br s, 1H), 7.00 (br s, 1H), 5.55 (s, 2H), 3.30 (s, 1H), 3.28 (s, 1H), 2.60 (q, 2H), 0.90 (t, 3H). MS (TSP) m/z 264 (MNH$_4^+$), 247 (MH$^+$). Anal. Calcd for C$_{11}$H$_{14}$N$_6$O.0.16H$_2$O: C, 53.38; H, 5.85; N, 34.08. Found: C, 53.20; H, 5.78; N, 33.75.

Preparation 46

5-Ethyl-4-{[2-isobutoxy-5-(methylsulfonyl)benzoyl]amino}-1-(3-pyridazinylmethyl)-1H-pyrazole-3-carboxamide Oxalyl chloride (233 mg, 1.84 mmol) was added to a solution of the title compound of preparation 9 (250 mg, 0.92 mmol) and N,N-dimethylformamide (20 mg) in DCM (5 ml) at 0° C. The solution was warmed to 20° C., stirred for 3 h and concentrated in vacuo. The residue was redissolved in DCM (5 ml) and the title compound from preparation 45 (253 mg, 0.92 mmol) and pyridine (145 mg, 1.84 mmol) were added. The mixture was stirred at 20° C. for 18 h, DCM (40 ml) and sat. NaHCO$_3$ (30 ml) were then added and the mixture shaken. The aqueous layer was separated and extracted with DCM (2×10 ml). The organic phases were combined, dried (Na$_2$SO$_4$), filtered and concentrated in vacuo. The crude product was purified by column chromatography (DCM/MeOH, 99:1–90:10) to afford the title compound as cream coloured crystals (360 mg, 0.77 mmol, 81%).

$^1$H NMR (400 MHz, CDCl$_3$) δ 10.20 (s, 1H), 9.20 (d, 1H), 8.75 (s, 1H), 8.00 (d, 1H), 7.50 (m, 1H), 7.20 (d, 1H), 7.15 (d, 1H), 6.70 (br s, 1H), 5.70 (s, 2H), 5.40 (br s, 1H), 4.10 (d, 2H), 3.05 (s, 3H), 2.90 (q, 2H), 2.40 (nonet, 1H), 1.10 (t, 3H), 1.05 (d, 6H). MS (TSP) m/z 518 (MNH$_4^+$), 501 (MH$^+$). Anal. Calcd for C$_{23}$H$_{28}$N$_6$O$_5$S.1.5H$_2$O: C, 52.36; H, 5.92; N, 15.93. Found: C, 52.48; H, 5.55; N, 15.74.

Preparation 47

4-Amino-3-ethyl-1-(3-pyridazinylmethyl)-1H-pyrazole-5-carboxamide

The title compound was formed as a pale pink solid in 41% yield from the title compound of preparation 43 by following the method used to prepare the title compound of preparation 6; mp 171–174° C.

$^1$H NMR (400 MHz, d$_6$-DMSO) δ 9.10 (d, 1H), 7.60 (m, 1H), 7.55 (br s, 2H), 7.00 (d, 1H), 5.80 (s, 2H), 2.50 (q, 2H), 1.10 (t, 3H). MS (TSP) m/z 247 (MH$^+$). Anal. Calcd for C$_{11}$H$_{14}$N$_6$O: C, 53.64; H, 5.73; N, 34.13. Found: C, 53.53; H, 5.74; N, 33.87.

Preparation 48

3-Ethyl-4-{[2-isobutoxy-5-(methylsulfonyl)benzoyl]amino}-1-(3-pyridazinylmethyl)-1H-pyrazole-5-carboxamide The title compound was formed in 85% yield by reacting the title compound of preparation 9 with the title compound of preparation 47 by following the same method used to synthesise the title compound of preparation 46; mp 196–200° C.

$^1$H NMR (400 MHz, CDCl$_3$) δ 9.50 (s, 1H), 9.15 (d, 1H), 8.80 (s, 1H), 8.20 (br s, 1H), 8.10 (d, 1H), 7.50 (m, 1H), 7.45 (d, 1H), 7.20 (d, 1H), 5.90 (s, 2H), 5.70 (br s, 1H), 4.10 (d, 2H), 3.10 (s, 3H), 2.80 (q, 2H), 2.30 (nonet, 1H), 1.20 (t, 3H), 1.10 (d, 6H). MS (ES+) m/z 523 (MNa$^+$), 501 (MH$^+$). Anal. Calcd for C$_{23}$H$_{28}$N$_6$O$_5$S.1.15H$_2$O: C, 52.99; H, 5.86; N, 16.12. Found: C, 52.74; H, 5.93; N, 16.14.

Preparation 49

5-Ethyl-4-{[2-isobutoxy-5-(methylsulfonyl)benzoyl]amino-}-1-(2-pyridinylmethyl)-1H-pyrazole-3-carboxamide Prepared in 57% yield by reacting the title compound of preparation 9 with 4-amino-5-ethyl-1-(2-pyridinylmethyl)-1H-pyrazole-3-carboxamide (prepared using the procedure in WO9954333) by following the same method used to synthesise the title compound of preparation 7.

$^1$H NMR (300 MHz, CDCl$_3$) δ 10.20 (br s, 1H), 8.75 (s, 1H), 8.60 (d, 1H), 8.00 (d, 1H), 7.65 (t, 1H), 7.20 (t, 1H), 7.15 (d, 1H), 6.95 (d, 1H), 6.75 (br s, 1H), 5.50 (br s, 1H), 5.45 (s, 2H), 4.10 (d, 2H), 3.05 (s, 3H), 2.85 (q, 2H), 2.40 (nonet, 1H), 1.05 (obscured multiplet, 3H), 1.05 (d, 6H). MS (TSP) m/z 500 (MH$^+$). Anal. Calcd for C$_{24}$H$_{29}$N$_5$O$_5$S.0.25DCM.0.6H$_2$O: C, 54.79; H, 5.82; N, 13.17. Found: C, 54.68; H, 5.64; N, 13.10.

Preparation 50

3-Ethyl-1-{[(2S)-1-methylpyrrolidinyl]methyl}-4-{[5-(methylsulfonyl)-2-propoxybenzoyl]amino-}-1H-pyrazole-5-carboxamide Prepared as a white solid in 64% yield by reacting the title compound of preparation 28 with the title compound of preparation 37 by following the same method used to synthesise the title compound of preparation 46; mp 217–221° C.

$^1$H NMR (300 MHz, CDCl$_3$) δ 10.30 (br s, 1H), 9.85 (s, 1H), 8.80 (s, 1H), 8.05 (d, 1H), 7.20 (d, 1H), 5.60 (br s, 1H), 4.20–4.40 (m, 4H), 3.15 (m, 1H), 3.10 (s, 3H), 3.10 (obscured multiplet, 1H), 2.75 (q, 2H), 2.40 (m, 1H), 2.05 (s, 3H), 2.05 (obscured multiplet, 2H), 1.80 (m, 1H), 1.70 (m, 2H), 1.60 (m, 1H), 1.25 (t, 3H), 1.10 (t, 3H). MS (TSP) m/z 492 (MH$^+$). High resolution MS m/z calcd for C$_{23}$H$_{34}$N$_5$O$_5$S: 492.2275; found: 492.2265 (MH$^+$).

Preparation 51

1-(1-Benzhydryl-3-azetidinyl)-3-ethyl-4-nitro-1H-pyrazole-5-carboxamide and

Preparation 52

1-(1-Benzhydryl-3-azetidinyl)-5-ethyl-4-nitro-1H-pyrazole-3-carboxamide

1-Benzhydryl-3-azetidinyl methanesulfonate (8.03 g, 25.3 mmol, prepared according to the procedure in J. Org. Chem. 1991, 56, 6729–30) was added to a mixture of 3-ethyl-4-nitro-1H-pyrazole-5-carboxamide (4.64 g, 25.3 mmol, prepared using procedure in WO9849166) and cesium carbonate (8.24 g, 25.3 mmol) in MeCN (170 ml). The mixture was heated to 75° C. for 2 h and concentrated in vacuo. Water (200 ml) and EtOAc (200 ml) were added, and the mixture shaken. The insoluble solid at the interface was filtered off and dried to afford the title compound of preparation 52. The two layers of the filtrate were separated and the organic phase was dried (MgSO$_4$), filtered and concentrated in vacuo. The residue was triturated with EtOAc (50 ml) and the resultant solid was filtered off, washed with hot DCM/MeOH (90:10, 50 ml) and dried to afford more of the title compound of preparation 52. The liquors and washings were combined and concentrated in vacuo. The residue was purified by column chromatography (DCM/MeOH, 98:2–95:5) to afford the title compound of preparation 51 plus a further small quantity of the title compound of preparation 52. The identity of the regioisomers was confirmed by nOe studies.

Total yield for the title compound of preparation 51: 5.80 g, 14.3 mmol, 56%; mp 178–180° C.

$^1$H NMR (400 MHz, d$_6$-DMSO) δ 8.35 (br s, 1H), 8.20 (br s, 1H), 7.40 (d, 4H), 7.20 (t, 4H), 7.15 (t, 2H), 4.90 (quintet, 1H), 4.50 (s, 1H), 3.50 (t, 2H), 3.35 (t, 2H), 2.85 (q, 2H), 1.20 (t, 3H). Anal. Calcd for C$_{22}$H$_{23}$N$_5$O$_3$.0.125H$_2$O: C, 64.80; H, 5.74; N, 17.18. Found: C, 65.14; H, 5.70; N, 16.82.

Total yield for the title compound of preparation 52: 2.90 g, 7.16 mmol, 28%; mp 254–257° C.

¹H NMR (400 MHz, d₆-DMSO) δ 7.90 (br s, 1H), 7.65 (br s, 1H), 7.40 (d, 4H), 7.20 (t, 4H), 7.15 (t, 2H), 5.20 (quintet, 1H), 4.55 (s, 1H), 3.60 (t, 2H), 3.40 (t, 2H), 2.90 (q, 2H), 1.05 (t, 3H). Anal. Calcd for $C_{22}H_{23}N_5O_3 \cdot 0.25H_2O$: C, 64.46; H, 5.78; N, 17.08. Found: C, 64.57; H, 5.68; N, 16.77.

Preparation 53

5-Ethy-1-(1-isopropyl-3-azetidinyl)-4-nitro-1H-pyrazole-3-carboxamide

1-Chloroethyl chloroformate (1.03 g, 7.20 mmol) was added to a solution of the title compound of preparation 52 (2.92 g, 7.20 mmol) in DCM (80 ml) at 0° C. The solution was warmed to 20° C. over 30 min and then heated to reflux for 1 h. The reaction mixture was concentrated in vacuo and azeotroped with DCM (80 ml). The residue was dissolved in MeOH (80 ml) and heated to reflux for 45 min. The reaction mixture was concentrated in vacuo and redissolved in THF (60 ml). Acetone (1.25 g, 21.6 mmol) and $Et_3N$ (0.73 g, 7.22 mmol) were added and the solution stirred at 20° C. for 30 min. $Na(OAc)_3BH$ (1.68 g, 7.92 mmol) and AcOH (0.23 ml) were added and the mixture stirred at 20° C. for 1 h. Further acetone was added (1.25 g) and the mixture stirred at 20° C. for 18 h. Sat $NaHCO_3$ (100 ml) and EtOAc (100 ml) were added and the mixture shaken. The organic layer was separated, dried ($MgSO_4$), filtered and concentrated in vacuo. The crude product was purified by column chromatography (DCM/MeOH, 95:5–90:10) to afford the title compound as a crystalline solid (1.14 g, 4.05 mmol, 56%); mp 184–187° C.

¹H NMR (400 MHz, CDCl₃) δ 6.95 (br s, 1H), 5.75 (br s, 1H), 4.90 (quintet, 1H), 3.80 (t, 2H), 3.55 (t, 2H), 2.95 (q, 2H), 2.50 (heptet, 1H), 1.25 (t, 3H), 1.00 (d, 6H). MS (TSP) m/z 282 (MH⁺). Anal. Calcd for $C_{12}H_{19}N_5O_3 \cdot 0.01Et_2O \cdot 0.12H_2O$: C, 50.88; H, 6.86; N, 24.64. Found: C, 51.26; H, 6.89; N, 24.30.

Preparation 54

4-Amino-5-ethyl-1-(1-isopropyl-3-azetidinyl)-1H-pyrazole-3-carboxamide

Prepared in 56% yield from the title compound of preparation 53 by the same procedure used to form the title compound of preparation 6; mp 195–200° C.

¹H NMR (400 MHz, CDCl₃) δ 6.60 (br s, 1H), 5.20 (br s, 1H), 4.75 (quintet, 1H), 3.90 (br s, 2H), 3.70 (t, 2H), 3.45 (t, 2H), 2.50 (q, 2H), 2.45 (heptet, 1H), 1.10 (t, 3H), 0.95 (d, 6H). MS (TSP) m/z 252 (MH⁺). Anal. Calcd for $C_{12}H_{21}N_5O \cdot 0.15H_2O$: C, 56.74; H, 8.45; N, 27.57. Found: C, 56.97; H, 8.52; N, 27.24.

Preparation 55

4-{[2-Butoxy-5-(methylsulfonyl)benzoyl]amino-}-5-ethyl-1-(1-isopropyl-3-azetidinyl)-1H-pyrazole-3-carboxamide Prepared in 62% yield by reacting the title compound of preparation 15 with the title compound of preparation 54 by following the same method used to synthesise the title compound of preparation 7; mp 198–201° C.

¹H NMR (300 MHz, d₆-DMSO) δ 10.00 (s, 1H), 8.30 (s, 1H), 8.05 (d, 1H), 7.50 (br s, 1H), 7.45 (d, 1H), 7.35 (br s, 1H), 5.00 (quintet, 1H), 4.30 (t, 2H), 3.80 (m, 2H), 3.50 (m, 2H), 3.20 (s, 3H), 3.00 (m, 1H), 2.70 (q, 2H), 1.80 (quintet, 2H), 1.40 (sextet, 2H), 1.10 (t, 3H), 0.95 (d, 6H), 0.90 (t, 3H). MS (TSP) m/z 506 (MH⁺). High resolution MS m/z calcd for $C_{24}H_{36}N_5O_5S$: 506.2432; found: 506.2424 (MH⁺).

Preparation 56

3-Ethyl-1-(1-isopropyl-3-azetidinyl)-4-nitro-1H-pyrazole-5-carboxamide

Prepared in 42% yield from the title compound of preparation 51 using the method used to prepare the title compound of preparation 53; mp 153–156° C.

¹H NMR (400 MHz, CDCl₃) δ 7.10. (br s, 1H), 6.05 (br s, 1H), 5.10 (quintet, 1H), 3.75 (t, 2H), 3.50 (t, 2H), 2.90 (q, 2H), 2.45 (heptet, 1H), 1.25 (t, 3H), 0.95 (d, 6H). Anal. Calcd for $C_{12}H_{19}N_5O_3 \cdot 0.125H_2O$: C, 50.82; H, 6.84; N, 24.70. Found: C, 51.05; H, 6.78; N, 24.44.

Preparation 57

4-Amino-3-ethyl-1-(1-isopropyl-3-azetidinyl)-1H-pyrazole-5-carboxamide

Prepared as a pale pink solid in 69% yield from the title compound of preparation 56 using the method used to prepare the title compound of preparation 6; mp 150–156° C.

¹H NMR (400 MHz, CDCl₃) δ 5.70 (quintet,1H), 3.80 (t, 2H), 3.50 (t, 2H), 2.90 (br s, 2H), 2.60 (q, 2H), 2.50 (heptet, 1H), 1.25 (t, 3H), 1.00 (d, 6H). MS (TSP) m/z 252 (MH⁺). Anal. Calcd for $C_{12}H_{21}N_5O \cdot 0.125H_2O$: C, 56.83; H, 8.45; N, 27.62. Found: C, 57.01; H, 8.62; N, 27.37.

Preparation 58

3-Ethyl-4-{[2-isobutoxy-5-(methylsulfonyl)benzoyl]amino-}-1-(1-isopropyl-3-azetidinyl)-1H-pyrazole-5-carboxamide Prepared in 71% yield by reacting the title compound of preparation 9 with the title compound of preparation 57 following the same method used to synthesise the title compound of preparation 7; mp 185–189° C.

¹H NMR (400 MHz, d₆-DMSO) δ 9.55 (s, 1H), 8.05 (s, 1H), 8.00 (d, 1H), 7.80 (br s, 1H), 7.40 (d, 1H), 7.35 (br s, 1H), 5.25 (quintet, 1H), 4.00 (d, 2H), 3.80 (m, 2H), 3.40 (m, 2H), 3.20 (s, 3H), 3.00 (m, 1H), 2.50 (q, 2H), 2.10 (m, 1H) 1.15 (t, 3H), 1.00 (d, 6H), 0.90 (d, 6H). MS (TSP) m/z 506 (MH⁺). Anal. Calcd for $C_{24}H_{35}N_5O_5S \cdot 0.4H_2O$: C, 56.21; H, 7.04; N, 13.66. Found: C, 56.01; H, 7.12; N, 13.89.

Preparation 59

3-Ethyl-4-{[2-isobutoxy-5-(methylsulfonyl)benzoyl]amino-}-1H-pyrazole-5-carboxamide Prepared as a white solid in 79% yield by reacting the title compound of preparation 9 with 4-amino-3-ethyl-1H-pyrazole-5-carboxamide (prepared using the procedure in WO9849166) by following the same method used to synthesise the title compound of preparation 46; mp 154–162° C.

¹H NMR (400 MHz, CD₃OD) δ 8.55 (s, 1H), 8.05 (d, 1H), 7.40 (d, 1H), 4.10 (d, 2H), 3.10 (s, 3H), 2.80 (q, 2H), 2.30 (nonet, 1H), 1.25 (t, 3H), 1.05 (d, 6H) MS (ES+) m/z 431 (MNa⁺), 409 (MH⁺). Anal. Calcd for $C_{18}H_{24}N_4O_5S \cdot 0.94H_2O \cdot 0.75CH_2Cl_2$: C, 46.04; H, 5.64; N, 11.45. Found: C, 46.39; H, 5.27; N, 11.36.

Preparation 60 tert-Butyl 4-(3-(aminocarbonyl)-5-ethyl-4-{[2-isobutoxy-5-(methylsulfonyl)benzoyl]amino-}-1H-pyrazol-1-yl)-1-piperidinecarboxylate $CsCO_3$ (1.40 g, 4.41 mmol) was added to a solution of the title compound of preparation 59 (1.50 g, 3.67 mmol) in N, N-dimethylformamide (15 ml) and was stirred at 20° C. for 15 min. tert-Butyl 4-[(methylsulfonyl)oxy]-1-piperidinecarboxylate (1.80 g, 6.61 mmol, prepared using procedure in *Bioorg. Med. Chem. Lett.* 1999, 9, 1285–1290) was added and the mixture heated to 80° C. for 9 h. The reaction mixture was concentrated in vacuo and then partitioned between EtOAc (50 ml) and H$_2$O (50 ml). The organic layer was dried (MgSO$_4$), filtered and concentrated in vacuo to give a brown oil. The crude product was purified by column chromatography (DCM/MeOH, 98:2 to 94:6) to afford the title compound (583 mg, 0.98 mmol, 27%); mp 134–141° C.

$^1$H NMR (400 MHz, CDCl$_3$) δ 10.10 (s, 1H), 8.75 (s, 1H), 8.00 (d, 1H), 7.15 (d, 1H), 6.60 (br s, 1H), 5.20 (br s, 1H), 4.30–4.20 (m, 3H), 4.10 (d, 2H), 3.85 (m, 1H), 3.05 (s, 3H), 2.90 (q, 2H), 2.90 (obscured m, 1H), 2.40 (nonet, 1H), 2.15 (m, 2H), 1.90 (m, 2H), 1.50 (s, 9H), 1.20 (t, 3H), 1.05 (d, 6H). MS (ES−) m/z 590 (M−H$^+$). Anal. Calcd for C$_{28}$H$_{41}$N$_5$O$_7$S.0.76H$_2$O: C, 55.55; H, 7.08; N, 11.57. Found: C, 55.33; H, 7.01; N, 11.19.

Preparation 61 tert-Butyl 4-{3-ethyl-5-[2-isobutoxy-5-(methylsulfonyl)phenyl]-7-oxo-6,7-dihydro-2H-pyrazolo[4,3-d]pyrimidin-2-yl}-1-piperidinecarboxylate Prepared as a white solid in 62% from the title compound of preparation 60 by following the method used to prepare the title compound of example 3.

$^1$H NMR (400 MHz, CDCl$_3$) δ 10.40 (s, 1H), 8.90 (s, 1H), 8.00 (d, 1H), 7.15 (d, 1H), 4.40–4.20 (m, 3H), 4.00 (d, 2H), 3.05 (s, 3H), 3.05 (q, 2H), 2.90 (m, 2H), 2.40 (m, 2H), 2.30 (nonet, 1H), 1.90 (m, 2H), 1.45 (s, 9H), 1.35 (t, 3H), 1.10 (d, 6H). MS (ES+) m/z 596 (MNa$^+$), 574 (MH$^+$). Anal. Calcd for C$_{28}$H$_{39}$N$_5$O$_6$S.0.8H$_2$O: C, 57.18; H; 6.96; N, 11.91. Found: C, 56.90; H, 6.91; N, 11.76.

Preparation 62

3-Ethyl-5-[2-isobutoxy-5-(methylsulfonyl)phenyl]-2-(4-piperidinyl)-2,6-dihydro-7H-pyrazolo[4,3-d]pyrimidin-7-one HCl was bubbled through a solution of the title compound of preparation 61 (352 mg, 0.61 mmol) in DCM (10 ml) at 0° C. for 15 min. The reaction mixture was then warmed to 20° C. and stirred for a further 1 h. The mixture was concentrated in vacuo and partitioned between sat. NaHCO$_3$ soln. (20 ml) and DCM (50 ml). The organic phase was dried (MgSO$_4$), filtered and concentrated in vacuo to give a white solid. The crude product was purified by column chromatography (DCM/MeOH/NH$_3$, 96:4:1 to 92:8:1) to afford the title compound as a white solid (160 mg, 0.34 mmol, 55%); mp 263–265° C.

$^1$H NMR (400 MHz, CDCl$_3$) δ 8.90 (s, 1H), 8.00 (d, 1H), 7.20 (d, 1H), 4.40 (m, 1H), 4.00 (d, 2H), 3.30 (d, 2H), 3.10 (s, 3H), 3.05 (q, 2H), 2.80 (t, 2H), 2.30 (m, 3H), 1.95 (d, 2H), 1.40 (t, 3H), 1.10 (d, 6H). MS (ES+) m/z 474 (MH$^+$). Anal. Calcd for C$_{23}$H$_{31}$N$_5$O$_4$S.0.8H$_2$O: C, 56.61; H, 6.73; N, 14.35. Found: C, 56.53; H, 6.85; N, 13.96.

Preparation 63

5-Amino-2-ethoxynicotinic acid

A solution of 2-ethoxy-5-nitronicotinic acid (12.0 g, 56.6 mmol, prepared by the method described in WO9954333) in a mixture of EtOH (150 ml), H$_2$O (150 ml), NaHCO$_3$ (4.80 g, 57.0 mmol) and 10% palladium on carbon (1.0 g) was hydrogenated at 60 psi and at 60° C. for 6 h. The mixture was cooled, filtered and acidified with AcOH. The mixture was concentrated in vacuo and the residue triturated with DCM/MeOH (95:5) to afford the title compound as a brown/purple solid (5.0 g, 27.5 mmol, 48%); mp 260–262° C.

$^1$H NMR (400 MHz, d$_6$-DMSO) δ 7.30 (s, 1H), 7.00 (s, 1H), 4.10 (q, 2H), 1.20 (t, 3H). MS (ES−) m/z 181 (M−H$^+$).

Preparation 64

2-Ethoxy-5-(methylsulfanyl)nicotinic acid

A solution of NaNO$_2$ (380 mg, 5.50 mmol) in H$_2$O (1 ml) was added dropwise to a solution of the title compound of preparation 63 (1.0 g, 5.50 mmol) in AcOH (5 ml) and H$_2$O (2 ml) at 0° C., whilst keeping the temperature below 5° C. After 30 min at 0° C., methyldisulphide (1.0 ml, 12.0 mmol) and CuBr$_2$ (50 mg, 0.22 mmol) were added and the mixture was warmed to 20° C. over 2 h. The mixture was concentrated in vacuo and partitioned between EtOAc (30 ml) and H$_2$O (30 ml). The organic phase was dried (Na$_2$SO$_4$), filtered and concentrated in vacuo. The crude product was purified by column chromatography (DCM/MeoH/AcOH, 95:5:10 to 90:10:10) followed by trituration with iPr$_2$O to afford the title compound as an orange solid (580 mg, 2.72 mmol, 50%); mp 78–92° C.

$^1$H NMR (400 MHz, CDCl$_3$) δ 8.40 (s, 1H), 8.30 (s, 1H), 4.65 (q, 2H), 2.50 (s, 3H), 1.50 (t, 3H). MS (ES−) m/z 212 (M−H$^+$). Anal. Calcd for C$_9$H$_{11}$NO$_3$S: C, 50.69; H, 5.20; N, 6.57. Found: C, 50.40; H, 5.08; N, 6.58.

Preparation 65

2-Ethoxy-5-(methylsulfonyl)nicotinic acid mCPBA (1.80 g of 50–55%, 5.20 mmol) was added to a solution of the title compound of preparation 64 (550 mg, 2.58 mmol) in DCM (15 ml) at 0° C., and the mixture was stirred at 0° C. for 2 h and then warmed to 20° C. for 1 h. The reaction was partitioned between DCM (50 ml) and 5% Na$_2$S$_2$O$_5$ soln. (50 ml), separated, and the aqueous phase extracted with DCM (2×50 ml). The aqueous phase was acidified to pH1 with conc. HCl and extracted with DCM (4×50 ml). The combined organic phases were dried (Na$_2$SO$_4$), filtered and concentrated in vacuo. The crude product was purified by column chromatography (DCM/MeOH/AcOH, 98:2:10 to 92:8:10) to afford the title compound (510 mg, 2.08 mmol, 81%); mp 175–176° C.

$^1$H NMR (400 MHz, CDCl$_3$) δ 8.90 (s, 2H), 4.75 (q, 2H), 3.10 (s, 3H), 1.55 (t, 3H). MS (ES−) m/z 244 (M−H$^+$). Anal. Calcd for C$_9$H$_{11}$NO$_5$S: C, 44.08; H, 4.52; N, 5.71. Found: C, 44.40; H, 4.42; N, 5.43.

Preparation 66 tert-Butyl (2S)-2-{[5-(aminocarbonyl)-4-({[2-ethoxy-5-(methylsulfonyl)-3-pyridinyl]carbonyl}amino)-3-ethyl-1H-pyrazol-1-yl]methyl}-1-pyrrolidinecarboxylate 10% Palladium on carbon (400 mg) was added to a solution of the title compound of preparation 34 (3.10 g, 8.45 mmol) in EtOH (100 ml) and hydrogenated at 60 psi and 20° C. for 4 h. The mixture was filtered and concentrated in vacuo to afford tert-butyl (2S)-2-{[4-amino-5-(aminocarbonyl)-3-ethyl-1H-pyrazol-1-yl]methyl}-1-pyrrolidinecarboxylate (2.70 g, 8.00 mmol, 95%). This was taken on crude in the following step.

Oxalyl chloride (0.21 ml, 2.40 mmol) was added to a solution of the title compound of preparation 65 (250 mg, 1.02 mmol) in DCM (10 ml) and N,N-dimethylformamide (10 ml) at −5° C. The solution was stirred at −5° C. for 30 min and then warmed to 20° C. over 3 h. The solution was concentrated in vacuo and azeotroped with DCM (2×50 ml). The residue was dissolved in DCM, tert-butyl (2S)-2-{[4-amino-5-(aminocarbonyl)-3-ethyl-1H-pyrazol-1-yl]methyl}-1-pyrrolidinecarboxylate (400 mg, 1.18 mmol) and pyridine (0.20 ml) were added and the mixture was stirred at 20° C. for 18 h. The mixture was diluted with DCM (50 ml) and washed with 2M HCl (50 ml). The organic phase was dried ($Na_2SO_4$), filtered and concentrated in vacuo. The crude product was purified by column chromatography (DCM/MeOH, 99:1 to 94:6) to afford the title compound (385 mg, 0.68 mmol, 67%).

$^1$H NMR (400 MHz, $CDCl_3$) δ 9.75 (br s, 0.5H), 9.20 (br s, 0.5H), 8.95 (s, 1H), 8.80 (s, 1H), 7.80 (br s, 0.5H), 7.40 (br s, 0.5H), 5.95 (br s, 1H), 4.75 (q, 2H) 4.40–4.50 (m, 2H), 4.20 (m, 1H), 3.30 (m, 2H), 3.10 (s, 3H), 2.60 (m, 2H), 1.70–2.00 (m, 4H), 1.50 (t, 3H), 1.40 (s, 9H), 1.20 (t, 3H). MS (ES−) m/z 563 (M−H$^+$).

Preparation 67 tert-Butyl (2S)-2-({3-ethyl-5-[5-(methylsulfonyl)-2-propoxy-3-pyridinyl]-7-oxo-6,7-dihydro-1H-pyrazolo[4,3-d]pyrimidin-1-yl}methyl)-1-pyrrolidinecarboxylate A mixture of the title compound of preparation 66 (380 mg, 0.67 mmol), propanol (5 ml), propyl acetate (0.80 ml, 0.69 mmol) and KOtBu (230 mg, 2.05 mmol) was heated to reflux for 2.5 h. The mixture was cooled and partitioned between EtOAc (50 ml) and $H_2O$ (30 ml) using solid $CO_2$ to neutralise. The organic phase was dried ($Na_2SO_4$), filtered and concentrated in vacuo. The crude product was purified by column chromatography (DCM/MeOH, 99:1 to 95:5) to afford the title compound (330 mg, 0.59 mmol, 88%), mp 98–104° C.

$^1$H NMR (400 MHz, $CDCl_3$) δ 9.30 (s, 1H), 8.80 (s, 1H), 4.70 (t, 3H), 4.70 (obscured m, 2H), 4.40 (m, 1H), 3.40 (m, 1H), 3.30 (m, 1H), 3.20 (s, 3H), 3.00 (q, 2H), 2.00 (sextet, 2H), 1.80 (m, 4H), 1.40 (m, 12H), 1.15 (t, 3H). MS (TSP) m/z 561 (MH$^+$). Anal. Calcd for $C_{26}H_{36}N_6O_6S \cdot 0.28H_2O$: C, 55.20; H, 6.51; N, 14.86. Found: C, 55.22; H, 6.50; N, 14.56.

Preparation 68

3-Ethyl-5-[5-(methylsulfonyl)-2-propoxy-3-pyridinyl]-1-[(2S)-pyrrolidinylmethyl]-1,6-dihydro-7H-pyrazolo[4,3-d]pyrimidin-7-one hydrochloride HCl was bubbled through a solution of the title compound of preparation 67 (320 mg, 0.57 mmol) in EtOAc (20 ml) at −5° C. for 25 min. The solution was concentrated in vacuo and triturated with $Et_2O$ to afford the title compound as a solid (220 mg, 0.43 mmol, 76%); mp 246–248° C.

$^1$H NMR (400 MHz, $d_6$-DMSO) δ 8.80 (s, 1H), 8.40 (s, 1H), 4.90 (dd, 1H), 4.80 (dd, 1H), 4.40 (t, 3H), 3.95 (m, 1H), 3.30 (s, 3H), 3.25 (m, 1H), 3.15 (m, 1H 2.85 (q, 2H), 2.00 (m, 1H), 1.90 (m, 2H), 1.70 (m, 3H), 1.30 (t, 3H), 0.90 (t, 3H). MS (ES−) m/z 459 (M−H$^+$). Anal. Calcd for $C_{21}H_{28}N_6O_4S \cdot 0.5H_2O \cdot HCl$: C, 49.85; H, 5.98; N, 16.61. Found: C, 49.80; H, 5.90; N, 16.47.

Preparation 69

3-Ethyl-4-{[5-(methylsulfonyl)-2-propoxybenzoyl]amino}-1H-pyrazole-5-carboxamide Prepared in 68% yield from the title compound of preparation 28 and 4-amino-3-ethyl-1H-pyrazole-5-carboxamide (prepared using the procedure in WO9849166) by following the same method used to synthesise the title compound of preparation 46; mp 209–210° C.

$^1$H NMR (400 MHz, $CDCl_3$) δ 10.30 (s, 1H), 8.75 (s, 1H), 8.00 (d, 1H), 7.15 (d, 1H), 4.25 (t, 2H), 3.05 (s, 3H), 2.80 (q, 2H), 2.30 (br s, 3H), 2.00 (sextet, 2H), 1.20 (t, 3H), 1.00 (t, 3H). MS (TSP) m/z 395 (MH$^+$).

Preparation 70

3-Ethyl-5-[5-(methylsulfonyl)-2-propoxyphenyl]-1,6-dihydro-7H-pyrazolo[4,3-d]pyrimidin-7-one Prepared as a white solid in 86% yield from the title compound of preparation 69 by following the procedure used to form the title compound of preparation 18, except that hot EtOH was used to triturate the crude product; mp 276–277° C.

$^1$H NMR (400 MHz, $CDCl_3$) δ 8.90 (s, 1H), 8.00 (d, 1H), 7.20 (d, 1H), 4.25 (t, 2H), 3.10 (s, 3H), 3.00 (q, 2H), 2.20 (br s, 2H), 2.00 (sextet, 2H), 1.40 (t, 3H), 1.10 (t, 3H). MS (ES+) m/z 399 (MNa$^+$), 377 (MH$^+$). Anal. Calcd for $C_{17}H_{20}N_4O_4S$: C, 54.24; H, 5.36; N, 14.88. Found: C, 54.11; H, 5.35; N, 14.73.

Preparation 71

7-Chloro-3-ethyl-5-[5-(methylsulfonyl)-2-propoxyphenyl]-1H-pyrazolo[4,3-d]pyrimidine Dimethylaniline (5.6 ml, 44.1 mmol) was added over 5 min to a suspension of the title compound of preparation 70 (8.0 g, 21.0 mmol) in $POCl_3$ (100 ml) at 20° C. The reaction mixture was heated to 65° C. and kept at this temperature for 2.5 h to give a very dark blue solution. This was cooled, concentrated in vacuo, dissolved in DCM (100 ml) and washed with 2M HCl (2×50 ml), $H_2O$ (100 ml) and then sat. $NaHCO_3$ soln. (100 ml). The DCM solution was dried ($Na_2SO_4$), filtered and concentrated in vacuo to afford the title compound as a blue/purple foam (7.2 g, 18.2 mmol, 87%).

$^1$H NMR (400 MHz, $CDCl_3$) δ 8.30 (s, 1H), 8.00 (d, 1H), 7.10 (d, 1H), 4.10 (t, 2H), 3.10 (q, 2H), 3.05 (s, 3H), 1.80 (sextet, 2H), 1.45 (t, 3H), 1.00 (t, 3H). MS (ES−) m/z 393 (M−H$^+$).

Preparation 72

3-Ethyl-7-methoxy-5-[5-(methylsulfonyl)-2-propoxyphenyl]-1H-pyrazolo[4,3-d]pyrimidine KOtBu (6.0 g, 53.5 mmol) was added to a solution of the title compound of preparation 71 (7.20 g, 18.2 mmol) in MeOH (200 ml), the mixture was heated to reflux for 2 h and then left at 20° C. for 18 h. The mixture was concentrated in vacuo and partitioned between DCM (150 ml) and $H_2O$ (100 ml) neutralised with 2M HCl and then sat. $NaHCO_3$ soln. The organic phase was dried ($Na_2SO_4$), filtered and concentrated in vacuo. The crude product was purified by column chromatography (DCM/MeOH, 99:1 to 96:4) and crystallisation from $Et_2O$ to afford the title compound (5.3 g, 13.6 mmol, 75%); mp 137–139° C.

$^1$H NMR (400 MHz, $CDCl_3$) δ 10.10 (br s, 1H), 8.35 (s, 1H), 7.95 (d, 1H), 7.15 (d, 1H), 4.20 (s, 3H), 4.05 (t, 2H), 3.10 (q, 2H), 3.05 (s, 3H), 1.80 (sextet, 2H), 1.45 (t, 3H), 1.00 (t, 3H). MS (ES+) m/z 413 (MNa$^+$), 391 (MH$^+$). Anal. Calcd for $C_{18}H_{22}N_4O_4S$: C, 55.37; H, 5.68; N, 14.35. Found: C, 55.15; H, 5.66; N, 14.31.

Preparation 73

5-(Chlorosulfonyl)-2-propoxybenzoic acid

A solution of 2-n-propoxybenzoic acid (20 g, 111 mmol) in DCM (40 ml) was added dropwise over 30 min to a mixture of chlorosulphonic acid (30 ml, 440 mmol) and thionyl chloride (8.1 ml, 110 mmol) at −10° C. whilst keeping the temperature below 0° C. The mixture was slowly warmed to 20° C. and stirred for 18 h. The reaction mixture was cautiously poured onto crushed ice (260 g), keeping the temperature below 0° C. The ice slurry was stirred for 20 min and then the precipitated white solid was filtered, washed with $H_2O$ (20 ml), dissolved in DCM (200 ml), dried ($MgSO_4$), filtered and concentrated in vacuo to afford the title compound as a yellow solid (31.2 g, 103 mmol, 92%); mp 121–124° C.

$^1$H NMR (400 MHz, $CDCl_3$) δ 8.80 (s, 1H), 8.20 (d, 1H), 7.20 (d, 1H), 4.30 (t, 2H), 2.00 (sextet, 2H), 1.10 (t, 3H). MS (TSP) m/z 296 ($MNH_4^+$). Anal. Calcd for $C_{10}H_{11}O_5SCl.0.6HCl.0.2H_2O$: C, 39.49; H, 3.98. Found: C, 39.42; H, 3.97.

Preparation 74

2-Propoxy-5-sulfinobenzoic acid

The title compound of preparation 73 (10 g, 36 mmol) and $NaHCO_3$ (5.50 g, 65.5 mmol) were added to a solution of $NaHCO_3$ (0.50 g, 6.00 mmol) and $Na_2SO_3$ (9.0 g, 72 mmol) in $H_2O$ (60 ml) portionwise over 1 h at 20° C. The reaction was stirred for 1.5 h and then cooled to 0° C. The mixture was acidified to pH 2 with 6N HCl and left for 18 h. The resultant crystals were filtered, washed with ice water (5 ml) and dried to afford the title compound (6.5 g, 26.6 mmol, 74%).

$^1$H NMR (400 MHz, $d_6$-DMSO) δ 7.80 (s, 1H), 7.70 (d, 1H), 7.20 (d, 1H), 4.00 (t, 2H), 1.70 (sextet, 2H), 0.95 (t, 3H). Anal. Calcd for $C_{10}H_{12}O_5S.0.2H_2O$: C, 48.46; H, 5.04. Found: C, 48.39; H, 4.84.

Preparation 75

5-(Ethylsulfonyl)-2-propoxybenzoic acid $Na_2CO_3$ (2.8 g, 26 mmol) was added portionwise to a solution of the title compound of preparation 74 (3.1 g, 13 mmol) in EtOH (50 ml) and $H_2O$ (50 ml). Ethyl iodide (5.1 ml, 63 mmol) was added and the mixture heated to reflux for 5 h. The mixture was cooled and 2N NaOH soln. (32 ml, 64 mmol) was added. The mixture was heated to reflux for 1 h, and the stirred at 20° C. for 18 h. The mixture was concentrated in vacuo to remove the EtOH, cooled to 0° C., acidified to pH 2 with 6N HCl and the precipitate filtered and dried to afford the title compound (2.7 g, 9.9 mmol, 76%).

$^1$H NMR (400 MHz, $d_6$-DMSO) δ 8.00 (s, 1H), 7.90 (d, 1H), 7.30 (d, 1H), 4.05 (t, 2H), 3.20 (q, 2H), 1.70 (sextet, 2H), 1.05 (t, 3H), 0.95 (t, 3H). MS (TSP) m/z 290 ($MNH_4^+$), 273 ($MH^+$). Anal. Calcd for $C_{12}H_{16}O_5S$: C, 52.93; H, 5.92. Found: C, 52.74; H, 5.91.

Preparation 76 tert-Butyl (2S)-2-[(5-(aminocarbonyl)-3-ethyl-4-{[5-(ethylsulfonyl)-2-propoxybenzoyl]amino}-1H-pyrazol-1-yl)methyl]-1-pyrrolidinecarboxylate Prepared as a beige foam in 95% yield by reacting tert-butyl (2S)-2-{[4-amino-5-(aminocarbonyl)-3-ethyl-1H-pyrazol-1-yl]methyl}-1-pyrrolidinecarboxylate (described in the synthesis of the title compound of preparation 66) with the title compound of preparation 75 following the method used to prepare the title compound of preparation 7 except that the crude product was purified by column chromatography (DCM/MeOH, 90:10).

$^1$H NMR (400 MHz, $CDCl_3$) δ 9.50 (br s, 0.5H), 9.20 (br s, 0.5H), 8.75 (s, 1H), 8.00 (d, 1H), 7.80 (br s, 0.5H), 7.60 (br s, 0.5H), 7.15 (d, 1H), 5.50 (br s, 1H), 4.50 (m, 1H), 4.40 (m, 1H), 4.25 (t, 2H), 4.20 (m, 1H), 3.30 (m, 2H), 3.10 (q, 2H), 2.55 (m, 2H), 1.95 (sextet, 2H), 1.70–1.90 (m, 4H), 1.45 (s, 9H), 1.25 (t, 3H), 1.20 (t, 3H), 1.05 (t, 3H). MS (ES−) m/z 590 (M−H$^+$). High resolution MS m/z calcd for $C_{28}H_{41}N_5O_7S$: 614.2619; found: 614.2629 ($MNa^+$).

Preparation 77 tert-Butyl (2S)-2-({3-ethyl-5-[5-(ethylsulfonyl)-2-propoxyphenyl]-7-oxo-6,7-dihydro-1H-pyrazolo[4,3-d]pyrimidin-1-yl}methyl)-1-pyrrolidinecarboxylate Prepared as a white solid in 61% yield from the title compound of preparation 76 by following the procedure used to synthesise the title compound of example 11; mp 170–172° C.

$^1$H NMR (400 MHz, $d_6$-DMSO) δ 12.10 (br s, 1H), 7.95 (m, 2H), 7.35 (d, 1H), 4.50 (m, 2H), 4.20 (m, 1H), 4.05 (t, 2H), 3.20 (m, 4H), 2.80 (q, 2H), 1.70 (m, 6H), 1.25 (s, 3H), 1.25 (t, 3H), 1.15 (s, 6H), 1.10 (t, 3H), 0.90 (t, 3H). MS (TSP) m/z 575 (MH$^+$). Anal. Calcd for $C_{28}H_{39}N_5O_6S$: C, 58.62; H, 6.85; N, 12.21. Found: C, 58.36; H, 6.84; N, 12.19.

Preparation 78

3-Ethyl-5-[5-(ethylsulfonyl)-2-propoxyphenyl]-1-[(2S)-pyrrolidinylmethyl]-1,6-dihydro-7H-pyrazolo[4,3-d]pyrimidin-7-one Trifluoroacetate Trifluoroacetic acid (1 ml) was added to a solution of the title compound of preparation 77 (145 mg, 0.25 mmol) in DCM (1 ml) at 20° C. The solution was stirred at 20° C. for 3 h, concentrated in vacuo and azeotropped with EtOAc (2×5 ml) to afford the title compound as a pale yellow gum (150 mg, 0.25 mmol, ~100%).

$^1$H NMR (400 MHz, $CDCl_3$) δ 10.25 (br s, 1H), 8.90 (s, 1H), 8.40 (br s, 1H), 8.00 (d, 1H), 7.20 (d, 1H), 4.95 (dd, 1H), 4.85 (dd, 1H), 4.30 (t, 2H), 3.50 (q, 2H), 3.30 (m, 1H), 3.15 (q, 2H), 2.95 (q, 2H), 2.35 (m, 1H), 2.10 (m, 1H), 2.00 (m, 3H), 1.75 (m, 1H), 1.35 (t, 3H), 1.30 (t, 3H), 1.15 (t, 3H). MS (ES+) m/z 474 (MH$^+$). High resolution MS m/z calcd for $C_{23}H_{31}N_5O_4S$: 474.2170; found: 474.2160 (MH$^+$).

Preparation 79

5-(Isopropylsulfonyl)-2-propoxybenzoic acid $Na_2CO_3$ (13.8 g, 130 mmol) was added portionwise to a solution of the title compound of preparation 74 (3.1 g, 13 mmol) in $H_2O$ (50 ml) and isopropanol (50 ml). Isopropyl iodide (6.3 ml, 63 mmol) was added and the mixture heated to reflux for 18 h. The reaction was cooled and 2N NaOH (32 ml, 64 mmol) was added. The mixture was heated to reflux for 1 h, cooled to 20° C. and stirred for a further 2 h. The mixture was concentrated in vacuo to remove the isopropanol, cooled to 0° C. and taken to pH 1 with 6N HCl. The precipitated solid was filtered and dried to afford the title compound (2.6 g, 9.1 mmol, 70%).

$^1$H NMR (400 MHz, $CDCl_3$) δ 8.60 (s, 1H), 8.00 (d, 1H), 7.15 (d, 1H), 4.25 (t, 2H), 3.15 (septet, 1H), 1.95 (sextet, 2H), 1.25 (d, 6H), 1.10 (t, 3H). MS (TSP) m/z 304 (MNH$_4^+$). Anal. Calcd for C$_{13}$H$_{18}$O$_5$S.0.25H$_2$O: C, 53.69; H, 6.41. Found: C, 53.62; H, 6.19.

Preparation 80 tert-Butyl (2S)-2-[(5-(aminocarbonyl)-3-ethyl-4-{[5-(isopropylsulfonyl)-2-propoxybenzoyl]amino}-1H-pyrazol-1-yl)methyl]-1-pyrrolidinecarboxylate Prepared as a white foam in 80% yield by following the procedure used to prepare the title compound of preparation 76, but using the title compound of preparation 79 in place of the title compound of preparation 75.

$^1$H NMR (400 MHz, CDCl$_3$) δ 9.50 (br s, 0.5H), 9.20 (br s, 0.5H), 8.70 (s, 1H), 8.00 (d, 1H), 7.80 (br s, 0.5H), 7.60 (br s, 0.5H), 7.15 (d, 1H), 5.50 (br s, 1H), 4.50 (m, 1H), 4.40 (m, 1H), 4.25 (t, 2H), 4.20 (m, 1H), 3.30 (m, 2H), 3.20 (septet, 1H), 2.55 (m, 2H), 1.95 (sextet, 2H), 1.70–2.00 (m, 4H), 1.45 (s, 9H), 1.30 (d, 6H), 1.20 (t, 3H), 1.05 (t, 3H). MS (ES−) m/z 604 (M−H$^+$). High resolution MS m/z calcd for C$_{29}$H$_{43}$N$_5$O$_7$S: 606.2956; found: 606.2966 (MH$^+$).

Preparation 81 tert-Butyl (2S)-2-({3-ethyl-5-[5-(isopropylsulfonyl)-2-propoxyphenyl]-7-oxo-6,7-dihydro-1H-pyrazolo[4,3-d]pyrimidin-1-yl}methyl)-1-pyrrolidinecarboxylate Prepared as a white solid in 58% yield from the title compound of preparation 80 by following the procedure used to synthesise the title compound of example 11; mp 141–143° C.

$^1$H NMR (400 MHz, d$_6$-DMSO) δ 12.10 (br s, 1H), 7.90 (m, 2H), 7.40 (d, 1H), 4.50 (m, 2H), 4.20 (m, 1H), 4.10 (t, 2H), 3.40 (heptet, 1H), 3.20 (m, 2H), 2.80 (q, 2H), 1.70 (m, 6H), 1.30 (s, 3H), 1.25 (t, 3H), 1.10 (m, 12H), 0.95 (t, 3H). MS (TSP) m/z 589 (MH$^+$). Anal. Calcd for C$_{29}$H$_{41}$N$_5$O$_6$S: C, 59.26; H, 7.03; N, 11.92. Found: C, 59.08; H, 7.07; N, 11.93.

Preparation 82

3-Ethyl-5-[5-(isopropylsulfonyl)-2-propoxyphenyl]-1-[(2S)-pyrrolidinylmethyl]-1,6-dihydro-7H-pyrazolo[4,3-d]pyrimidin-7-one Trifluoroacetate Prepared as a pale yellow gum in ~100% yield from the title compound of preparation 81 by following the procedure used to synthesise the title compound of example 78.

$^1$H NMR (300 MHz, CDCl$_3$) δ 10.00 (br s, 1H), 8.95 (s, 1H), 8.40 (br s, 1H), 8.00 (d, 1H), 7.25 (d, 1H), 5.00 (dd, 1H), 4.95 (dd, 1H), 4.35 (t, 2H), 3.60 (m, 2H), 3.40 (m, 1H), 3.30 (septet, 1H), 3.00 (q, 2H), 2.40 (m, 1H), 2.00–2.20 (m, 4H), 1.80 (m, 1H), 1.40 (t, 3H), 1.35 (d, 6H), 1.20 (t, 3H). MS (ES+) m/z 488 (MH$^+$). High resolution MS m/z calcd for C$_{24}$H$_{33}$N$_5$O$_4$S: 488.2326; found: 488.2319 (MH$^+$).

Preparation 83

(3aS)Hexahydro[1,2,3]oxathiazolo[3,4-a]pyridine 1,1-dioxide

SO$_2$Cl$_2$ (0.27 ml, 3.36 mmol) was added dropwise over 5 min to a suspension of (2S)-piperidinylmethanol hydrochloride (500 mg, 3.30 mmol) in DCM (10 ml), pyridine (1 ml) and triethylamine (0.46 ml) at −70° C. The mixture was stirred at this temperature for 30 min and then warmed to 20° C. and stirred for 2 h. DCM (50 ml) was added and the solution washed with 0.5M HCl (3×50 ml). The organic phase was dried (Na$_2$SO$_4$), filtered and concentrated in vacuo to afford the title compound as a yellow oil (80 mg, 0.45 mmol, 14%).

$^1$H NMR (400 MHz, CDCl$_3$) δ 4.45 (dd, 1H), 4.15 (dd, 1H), 3.55 (m, 1H), 3.45 (m, 1H), 2.75 (dt, 1H), 1.90 (m, 3H), 1.60 (m, 1H), 1.40 (m, 2H). MS (ES+) m/z 178 (MH$^+$).

Preparation 84

3-Ethyl-5-[5-(methylsulfonyl)-2-propoxyphenyl]-1-[(2S)-piperidinylmethyl]-1,6-dihydro-7H-pyrazolo[4,3-d]pyrimidin-7-one A mixture of the title compound of preparation 72 (165 mg, 0.423 mmol), the title compound of preparation 83 (75 mg, 0.423 mmol), K$_2$CO$_3$ (150 mg, 1.08 mmol) and N,N-dimethylformamide (1 ml) was heated to reflux for 4 h, cooled and then stirred at 20° C. for 18 h. The reaction was concentrated in vacuo, acidified to pH 1 with 2M HCl and extracted with DCM (2×50 ml). The organics were combined, dried (Na$_2$SO$_4$), filtered and concentrated in vacuo to afford (2S)-2-({3-ethyl-7-methoxy-5-[5-(methylsulfonyl)-2-propoxyphenyl]-1H-pyrazolo[4,3-d]pyrimidin-1-yl}methyl)-1-piperidinesulfonic acid as a pale yellow oil (280 mg). 6M HCl (10 ml) was added and the mixture was stirred at 50° C. for 40 h. The reaction was cooled, diluted with H$_2$O (50 ml) and basified with 0.880 NH$_3$ soln. This was extracted with DCM (2×50 ml) and the combined extracts were dried (Na$_2$SO$_4$), filtered and concentrated in vacuo to give a semi solid. The crude product was purified by column chromatography (DCM/MeOH, 96:4 to 92:8) and trituration with Et$_2$O to afford the title compound as a white solid (60 mg, 0.13 mmol, 30%); mp 207–208° C.

$^1$H NMR (400 MHz, CDCl$_3$) δ 9.00 (s, 1H), 8.00 (d, 1H), 7.20 (d, 1H), 4.65 (dd, 1H), 4.55 (dd, 1H), 4.30 (t, 2H), 3.10 (s, 3H), 3.10 (obscured m, 2H), 3.00 (q, 2H), 2.60 (t, 1H), 2.05 (sextet, 2H), 1.80 (m, 1H), 1.70 (m, 1H), 1.60 (m, 1H), 1.30–1.50 (m, 3H), 1.40 (t, 3H), 1.20 (t, 3H). MS (TSP) m/z 474 (MH$^+$). Anal. Calcd for C$_{23}$H$_{31}$N$_5$O$_4$S.0.25H$_2$O: C, 57.78; H, 6.64; N, 14.65. Found: C, 57.72; H, 6.56; N, 14.60.

Preparation 85

2-Butoxy-5-(methylsulfonyl)benzamide

Oxalyl chloride (3.47 ml, 39.4 mmol) was added dropwise to a solution of the title compound of preparation 15 (9.76 g, 35.8 mmol) in DCM (250 ml) and N,N-dimethylformamide (1 drop) at 0° C. The reaction mixture was warmed to 20° C., stirred for 6 h, concentrated in vacuo and azeotroped with DCM (2×50 ml). The resulting oil was dissolved in DCM (250 ml), cooled to 0° C. and NH$_3$ (0.5 M in dioxane, 179 ml, 89.5 mmol) was added. The reaction mixture was warmed to 20° C. and stirred for 18 h. The reaction mixture was concentrated in vacuo and partitioned between DCM (300 ml) and H$_2$O (150 ml). The organic phase was dried (Na$_2$SO$_4$), filtered and concentrated in vacuo. The resultant beige solid was triturated with Et$_2$O (50 ml) to afford the title compound as a white solid (6.86 g, 25.3 mmol, 71%); mp 146–150° C.

$^1$H NMR (400 MHz, CDCl$_3$) δ 8.80 (s, 1H), 8.00 (d, 1H), 7.65 (br s, 1H), 7.10 (d, 1H), 6.20 (br s, 1H), 4.25 (t, 2H), 3.05 (s, 3H), 1.90 (quintet, 2H), 1.55 (sextet, 2H), 1.00 (t, 3H). MS (ES+) m/z 565 (M$_2$Na$^+$). Anal. Calcd for C$_{12}$H$_{17}$NO$_4$S.0.3H$_2$O: C, 52.08; H, 6.41; N, 5.06. Found: C, 52.53; H, 6.12; N, 4.75.

Preparation 86

2-Butoxy-5-(methylsulfonyl)benzenecarbothioamide

The title compound of prepartion 85 (2.66 g, 9.80 mmol) was suspended in toluene (50 ml) and Lawesson's reagent (1.98 g, 4.90 mmol) was added. The reaction mixture was heated to 80° C. for 2 h, then left for 18 h at 20° C. The precipitated solid was filtered and dried to afford the title compound as a yellow solid (1.81 g, 6.30 mmol, 64%).

$^1$H NMR (400 MHz, CDCl$_3$) δ 9.10 (s, 1H), 8.70 (br s, 1H), 8.00 (d, 1H), 8.00 (br s, 1H), 7.10 (d, 1H), 4.20 (t, 2H), 3.05 (s, 3H), 1.90 (quintet, 2H), 1.50 (sextet, 2H), 1.00 (t, 3H). MS (ES−) m/z 286 (M−H$^+$).

Preparation 87

Methyl 2-butoxy-5-(methylsulfonyl)benzenecarbimidothioate hydroiodide

Iodomethane (0.47 ml, 7.60 mmol) was added to a solution of the title compound of preparation 86 (1.81 g, 6.30 mmol) in acetone (30 ml). The solution was stirred at 20° C. for 18 h, and the precipitated solid was filtered and dried to afford the title compound as a pink solid (1.62 g, 3.78 mmol, 60%); mp 194–198° C.

$^1$H NMR (400 MHz, d$_6$-DMSO) δ 8.15 (d, 1H), 8.00 (s, 1H), 7.50 (d, 1H), 4.20 (t, 2H), 3.25 (s, 3H), 2.75 (s, 3H), 1.70 (quintet, 2H), 1.50 (sextet, 2H), 0.90 (t, 3H). MS (ES+) m/z 302 (MH$^+$). Anal. Calcd for C$_{13}$H$_{19}$NO$_3$S$_2$.HI: C, 36.37; H, 4.70; N, 3.26. Found: C, 36.28; H, 4.62; N, 3.19.

Preparation 88

2-Butoxy-5-(methylsulfonyl)benzenecarboximidohydrazide hydroiodide

Hydrazine monohydrate (0.057 ml, 1.16 mmol) was added to a suspension of the title compound of preparation 87 (500 mg, 1.16 mmol) in THF (10 ml), and the mixture stirred at 20° C. for 18 h. The precipitated solid was filtered and dried to afford the title compound (444 mg, 0.99 mmol, 85%); mp 174–182° C.

$^1$H NMR (400 MHz, CD$_3$OD) δ 8.20 (d, 1H), 8.00 (s, 1H), 7.40 (d, 1H), 4.20 (t, 2H), 3.15 (s, 3H), 1.80 (quintet, 2H), 1.50 (sextet, 2H), 1.00 (t, 3H). MS (ES+) m/z 286 (MH$^+$). Anal. Calcd for C$_{12}$H$_{19}$N$_3$O$_3$S.HI.0.5THF: C, 37.57; H, 5.40; N, 9.37. Found: C, 37.30; H, 5.26; N, 9.20.

Preparation 89

2-(Propionylamino)-4-pentenoic acid

Propionic anhydride (18.0 ml, 140 mmol) was added dropwise to a solution of DL-2-amino-4-pentenoic acid (14.6 g, 127 mmol) and K$_2$CO$_3$ (19.3 g, 140 mmol) in H$_2$O (100 ml) at 0° C. The reaction mixture was warmed to 20° C. and stirred for 18 h. Conc. HCl was added until the pH was 1, and the mixture was extracted with DCM (2×100 ml). The combined organics were dried (Na$_2$SO$_4$), filtered and concentrated in vacuo. The crude product was triturated with pentane (100 ml) to afford the title compound as white crystals (18.9 g, 110 mmol, 87%); mp 96–98° C.

$^1$H NMR (400 MHz, CDCl$_3$) δ 6.25 (d, 1H), 5.70 (m, 1H), 5.15 (d, 2H), 4.70 (q, 1H), 2.65 (m, 1H), 2.55 (m, 1H), 2.30 (q, 2H), 1.15 (t, 3H). MS (ES+) m/z 172 (MH$^+$). Anal. Calcd for C$_8$H$_{13}$NO$_3$: C, 56.13; H, 7.65; N, 8.18. Found: C, 56.04; H, 7.56; N, 8.11.

Preparation 90

N-Methoxy-N-methyl-2-(propionylamino)-4-pentenamide

2-Chloro-4,6-dimethoxy-1,3,5-triazine (14.47 g, 82.0 mmol) was added to a solution of the title compound of preparation 89 (12.74 g, 75.0 mmol) in THF (100 ml) and N-methylmorpholine (18.2 ml, 165 mmol) at 20° C. After 1 h a white precipitate had formed. N,O-dimethylhydroxylamine hydrochloride (7.80 g, 80.0 mmol) was added and the mixture was stirred at 20° C. for 3 days. The reaction mixture was concentrated in vacuo and partitioned between DCM (150 ml) and H$_2$O (50 ml). The aqueous phase was extracted with DCM (50 ml), and the combined organics were washed with 10% Na$_2$CO$_3$ soln. (50 ml) and 2M HCl (50 ml). The DCM solution was dried (Na$_2$SO$_4$), filtered and concentrated in vacuo. The crude product was purified by column chromatography (ethyl acetate) to afford the title compound as a yellow oil (12.3 g, 57.4 mmol, 77%).

$^1$H NMR (400 MHz, CDCl$_3$) δ 6.10 (br s, 1H), 5.70 (m, 1H), 5.10 (m, 3H), 3.80 (s, 3H), 3.20 (s, 3H), 2.55 (m, 1H), 2.40 (m, 1H), 2.20 (q, 2H), 1.15 (t, 3H). MS (ES+) m/z 237 (MNa$^+$). High resolution MS m/z calcd for C$_{10}$H$_{18}$N$_2$O$_3$Na: 237.1210; found: 237.1213 (MNa$^+$).

Preparation 91

N-(1-Formyl-3-butenyl)propanamide

LiAlH$_4$ (1M in THF, 34.0 ml, 34.0 mmol) was added dropwise over 45 min to a solution of the title compound of preparation 90 (10.5 g, 49.0 mmol) in THF under N$_2$ at −10° C. The reaction was warmed to 20° C. and stirred for 3 h. KHSO$_4$ soln. (20 g in 150 ml H$_2$O) was cautiously added, and the mixture stirred for 10 min and then concentrated in vacuo to remove the THF. The aqueous phase was extracted with DCM (2×100 ml), and the combined organics were dried (Na$_2$SO$_4$), filtered and concentrated in vacuo. The crude product was purified by column chromatography (1:1, pentane/EtOAc) to afford the title compound as a yellow oil (3.30 g, 21.3 mmol, 43%).

$^1$H NMR (400 MHz, CDCl$_3$) δ 9.60 (s, 1H), 6.00 (br s, 1H), 5.70 (m, 1H), 5.10 (m, 2H), 4.60 (q, 1H2.60 (m, 2H), 2.20 (q, 2H), 1.15 (t, 3H).

Preparation 92

N-{1-[Cyano(hydroxy)methyl]-3-butenyl}propanamide

Acetone cyanohydrin (2.0 ml, 22 mmol) was added to a solution of the title compound of preparation 91 (3.30 g, 21.3 mmol) in DCM (50 ml) and Et$_3$N (3.1 ml) and the mixture was stirred for 18 h at 20° C. A further 0.5 ml of acetone cyanohydrin was added and the mixture stirred for a further 18 h. The reaction was concentrated in vacuo and the crude product purified by column chromatography (pentane/EtOAc, 60:40–40:60) to afford the title compound as a 1:1 mixture of diastereoisomers, yellow oil (2.35 g, 12.9 mmol, 61%).

$^1$H NMR (400 MHz, CDCl$_3$) δ 5.90 (m, 1H), 5.75 (m, 1H), 5.20 (m, 2H), 4.70 (m, 0.5H), 4.55 (m, 0.5H), 4.20 (m, 0.5H), 4.00 (m, 0.5H), 2.20–2.50 (m, 4H), 1.20 (m, 3H). MS (ES+) m/z 205 (MNa$^+$). High resolution MS m/z calcd for C$_9$H$_{15}$N$_2$O$_2$: 183.1128; found: 183.1134 (MH$^+$).

Preparation 93

Ethyl 2-hydroxy-3-(propionylamino)-5-hexenoate

HCl was bubbled through a solution of the title compound of preparation 92 (2.35 g, 12.9 mmol) in EtOH (40 ml) at −10° C. until saturated. The reaction was warmed to 5° C. and the vessel was sealed and left in a refrigerator at 5° C.

for 18 h. The reaction mixture was concentrated in vacuo, ice (~100 g) was added and the mixture warmed to 20° C. and stirred for 30 min. The aqueous phase was basified with 10% $Na_2CO_3$ soln. and extracted with DCM (100 ml). 2M HCl (50 ml) was added to the DCM extract and the mixture stirred for 30 min. The DCM layer was separated, washed with 10% $Na_2CO_3$ soln. (100 ml), dried ($Na_2SO_4$), filtered and concentrated in vacuo to an oil. All the aqueous phases were combined (pH ~6) and extracted with DCM (4×40 ml). The combined extracts were dried ($Na_2SO_4$), filtered and concentrated in vacuo to an oil. This was combined with the previous oil to afford the title compound (2.00 g, 8.7 mmol, 67%).

$^1$H NMR (400 MHz, $CDCl_3$) δ 5.60–5.80 (m, 2H), 5.10 (m, 2H), 4.40 (m, 1H), 4.20 (m, 3H), 3.40 (br s, 0.5H), 3.20 (br s, 0.5H), 2.40 (q, 1H), 2.20 (m, 3H), 1.30 (m, 3H), 1.10 (m, 3H). MS (ES–) m/z 228 (M–H$^+$). High resolution MS m/z calcd for $C_{11}H_{20}NO_4$: 230.1387; found: 230.1395 (MH$^+$).

Preparation 94

Ethyl 2-oxo-3-(Propionylamino)-5-hexenoate

Dess-Martin periodinane (4.25 g,10 mmol) was added to a solution of the title compound of preparation 93 (2.00 g, 8.73 mmol) in DCM (40 ml) at 20° C. After 1.5 h, satd. $Na_2S_2O_3$ soln. (50 ml) and satd. $NaHCO_3$ soln. (50 ml) were added, and the mixture stirred for 30 min. The layers were separated, and the aqueous phase was extracted with DCM (2×50 ml). The combined organics were dried ($Na_2SO_4$), filtered and concentrated in vacuo. The crude product was purified by column chromatography (pentane/EtOAc, 75:25–25:75) to afford the title compound as a pale yellow oil (1.30 g, 5.72 mmol, 65%).

$^1$H NMR (400 MHz, $CDCl_3$) δ 6.00 (br s, 1H), 5.65 (tdd, 1H), 5.25 (q, 1H), 5.15 (dd, 1H), 5.10 (dd, 1H), 4.35 (q, 2H), 2.70 (dt, 1H), 2.50 (ddd, 1H), 2.25 (q, 2H), 1.35 (t, 3H), 1.15 (t, 3H). MS (ES+) m/z 228 (MH$^+$), 250 (MNa$^+$). High resolution MS m/z calcd for $C_{11}H_{17}NO_4Na$: 250.1050; found: 250.1057 (MNa$^+$).

Preparation 95

N-(1-{3-[2-Butoxy-5-(methylsulfonyl)phenyl]-5-oxo-4,5-dihydro-1,2,4-triazin-6-yl}-3-butenyl) propanamide The title compound of preparation 94 (110 mg, 0.485 mmol), the title compound of preparation 88 (200 mg, 0.484 mmol) and $NaHCO_3$ (100 mg, 1.2 mmol) were combined in EtOH (2 ml) and heated to reflux for 18 h. A further 100 mg of $NaHCO_3$ was added and the reaction heated to reflux for a further 3 days. The reaction mixture was cooled and partitioned between DCM (50 ml) and $H_2O$ (10 ml). The pH of the aqueous phase was lowered from 9 to 8 by the addition of solid $CO_2$, and extracted with DCM (20 ml). The combined organics were dried ($Na_2SO_4$), filtered and concentrated in vacuo. The crude product was purified by column chromatography (DCM/MeOH/$NH_{3(aq)}$, 98:2:10–94:6:10) to afford the title compound as a brown solid (90 mg, 0.20 mmol, 41%).

$^1$H NMR (400 MHz, $CDCl_3$) δ 12.15 (brs, 1H), 9.15 (s, 1H), 8.15 (d, 1H), 6.80 (d, 1H), 5.70 (m, 1H), 5.20 (q, 1H), 5.10 (m, 2H), 4.40 (t, 2H), 3.10 (s, 3H) 2.70 (m, 2H), 2.25 (q, 2H), 2.00 (quintet, 2H), 1.60 (obscured m, 2H), 1.15 (t, 3H), 1.05 (t, 3H). MS (ES+) m/z 471 (MNa$^+$).

Synthesis of Compounds of Formulae IA, IB and ID

Example 1

5-[2-Ethoxy-5-(methylsulfonyl)phenyl]-1-methyl-3-propyl-1,6-dihydro-7H-pyrazolo[4,3-d]pyrimidin-7-one

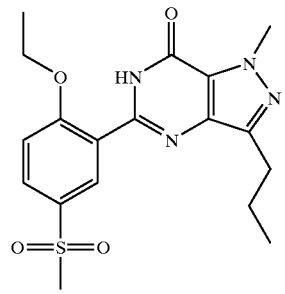

A mixture of the title compound of preparation 2 (130 mg, 0.50 mmol), 4-amino-1-methyl-3-propyl-1H-pyrazole-5-carboxamide (90 mg, 0.50 mmol, prepared using the procedure in EP463756), KHMDS (100 mg, 0.50 mmol) and potassium tert-butoxide (56 mg, 0.50 mmol) in 3-methyl-3-pentanol (3 ml) was heated at 120° C. for 3 h. The mixture was cooled and concentrated in vacuo. The residue was partitioned between EtOAc (10 ml) and water (10 ml, adjusted to pH 5 with 2M HCl). The organic layer was dried ($MgSO_4$), filtered and concentrated in vacuo. The crude product was purified by column chromatography (EtOAc/MeOH, 95:5) to afford the title compound as a solid (8 mg, 0.02 mmol, 4%); mp 235–236° C.

$^1$H NMR (400 MHz, $d_6$-DMSO) δ 12.15 (br s, 1H), 8.05 (s, 1H), 8.00 (d, 1H), 7.35 (d, 1H), 4.20 (q, 2H), 4.15 (s, 3H), 3.20 (s, 3H), 2.75 (t, 2H), 1.70 (sextet, 2H), 1.30 (t, 3H), 0.90 (t, 3H). MS (TSP) m/z 391 (MH$^+$).

Example 2

5-[2-Butoxy-5-(methylsulfonyl)phenyl]-3-ethyl-2-(2-methoxyethyl)-2,6-dihydro-7H-pyrazolo[4,3-d]pyrimidin-7-one

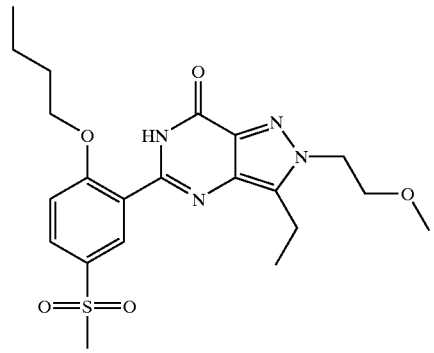

A mixture of the title compound of preparation 7 (130 mg, 0.30 mmol) and potassium tert-butoxide (100 mg, 0.89 mmol) in butanol (5 ml) was heated at reflux for 18 h. On cooling, EtOAc (20 ml) and water (20 ml) were added and the mixture shaken. The layers were separated and the organic phase was dried ($MgSO_4$), filtered and concentrated in vacuo. The crude product was purified by column chromatography (EtOAc/MeOH, 95:5) and then triturated with EtOAc to afford the title compound as a solid (12 mg, 0.027 mmol, 9%); mp 174–176° C.

$^1$H NMR (400 MHz, d$_6$-DMSO) δ 11.65 (s, 1H), 8.00 (s, 1H), 7.95 (d, 1H), 7.35 (d, 1H), 4.40 (t, 2H), 4.10 (t, 2H), 3.75 (t, 2H), 3.20 (s, 3H), 3.20 (s, 3H), 2.90 (q, 2H), 1.65 (m, 2H), 1.35 (sextet, 2H), 1.20 (t, 3H), 0.85 (t, 3H). MS (TSP) m/z 449 (MH$^+$). High resolution MS m/z calcd for C$_{21}$H$_{29}$N$_4$O$_5$S: 449.1853; found: 449.1861 (MH$^+$).

Example 3

3-Ethyl-5-[2-isobutoxy-5-(methylsulfonyl)phenyl]-1-(2-pyridinylmethyl)-1,6-dihydro-7H-pyrazolo[4,3-d]pyrimidin-7-one

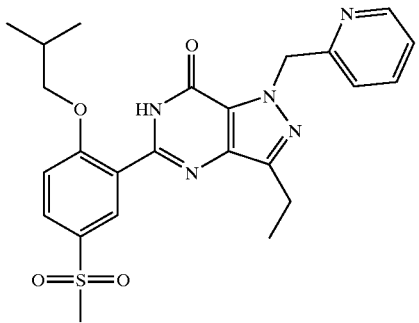

A mixture of the title compound of preparation 10 (410 mg, 0.82 mmol), KHMDS (490 mg, 2.46 mmol) and isobutyl acetate (190 mg, 1.64 mmol) in isobutanol (6 ml) was heated to reflux for 3 h. The turbid solution was cooled and acetic acid (148 mg, 2.46 mmol) was added. Toluene (100 ml) was added and the solution concentrated in vacuo. DCM (100 ml) and water (100 ml) were added to the residue and the mixture shaken. The layers were separated and the aqueous phase extracted with DCM (2×100 ml). The organic phases were combined, dried (MgSO$_4$), filtered and concentrated in vacuo. The crude product was purified by column chromatography (DCM/MeOH, 99:1–95:5) to afford the title compound as a white solid (360 mg, 0.75 mmol, 91%); mp 223–225° C.

$^1$H NMR (400 MHz, CDCl$_3$) δ 10.90 (br s, 1H), 9.05 (s, 1H), 8.60 (d, 1H), 8.00 (d, 1H), 7.60 (t, 1H), 7.20 (d, 1H), 7.15 (t, 1H), 7.00 (d, 1H), 5.95 (s, 2H), 4.05 (d, 2H), 3.10 (s, 3H), 3.00 (q, 2H), 2.35 (nonet, 1H), 1.40 (t, 3H), 1.15 (d, 6H). MS (ES+) m/z 504 (MNa$^+$), 482 (MH$^+$). Anal. Calcd for C$_{24}$H$_{27}$N$_5$O$_4$S.0.2H$_2$O: C, 59.41; H, 5.69; N, 14.43. Found: C, 59.38; H, 5.60; N, 14.41.

Example 4

3-Ethyl-5-[2-(2-methoxyethoxy)-5-(methylsulfonyl)phenyl]-1-(2-pyridinylmethyl)-1,6-dihydro-7H-pyrazolo[4,3-d]pyrimidin-7-one

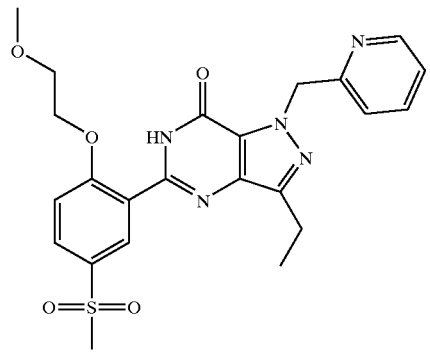

A mixture of the title compound of preparation 13 (210 mg, 0.42 mmol), KHMDS (251 mg, 1.26 mmol) and 2-methoxyethyl acetate (50 mg, 0.42 mmol) in 2-methoxyethanol (10 ml) was heated to reflux for 18 h. The mixture was concentrated in vacuo, and the residue dissolved in water (5 ml). The pH was adjusted to 7 with 2M HCl, and the precipitate was filtered and dried to afford the title compound (90 mg, 0.19 mmol, 43%); mp 166–167° C.

$^1$H NMR (300 MHz, CDCl$_3$) δ 11.10 (br s, 1H), 9.00 (s, 1H), 8.60 (d, 1H), 8.05 (d, 1H), 7.60 (t, 1H), 7.20 (two obscured multiplets, 2H), 7.00 (d, 1H), 5.95 (s, 2H), 4.45 (br m, 2H), 3.90 (br m, 2H), 3.60 (s, 3H), 3.15 (s, 3H), 3.05 (q, 2H), 1.40 (t, 3H). MS (ES+) m/z 484 (MH$^+$). Anal. Calcd for C$_{23}$H$_{25}$N$_5$O$_5$S.0.3H$_2$O: C, 56.50; H, 5.28; N, 14.32. Found: C, 56.47; H, 5.17; N, 14.25.

Example 5

5-[2-Butoxy-5-(methylsulfonyl)phenyl]-3-ethyl-1-(2-pyridinylmethyl)-1,6-dihydro-7H-pyrazolo[4,3-d]pyrimidin-7-one

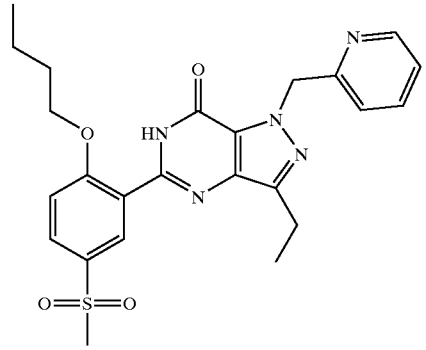

Prepared in 76% yield from the title compound of preparation 16 by following a procedure analogous to that used for the synthesis of the title compound of example 4, but using butanol as the solvent and butyl acetate as the potassium hydroxide scavenger; mp 189–191° C.

$^1$H NMR (300 MHz, CDCl$_3$) δ 10.90 (br s, 1H), 9.05 (s, 1H), 8.60 (d, 1H), 8.05 (d, 1H), 7.60 (t, 1H), 7.20 (two obscured multiplets, 2H), 7.05 (d, 1H), 5.95 (s, 2H), 4.35 (t, 2H), 3.15 (s, 3H), 3.05 (q, 2H), 2.00 (quintet, 2H), 1.60

(sextet, 2H), 1.45 (t, 3H), 1.05 (t, 3H). MS (ES+) m/z 482 (MH+). Anal. Calcd for C$_{24}$H$_{27}$N$_5$O$_4$S: C, 59.85; H, 5.65; N, 14.54. Found: C, 59.70; H, 5.69; N, 14.29.

Example 6

3-Ethyl-5-[5-(methylsulfonyl)-2-(2-pyridinylmethoxy)phenyl]-1,6-dihydro-7H-pyrazolo[4,3-d]pyrimidin-7-one

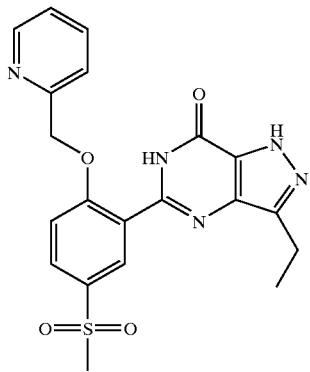

A mixture of the title compound of preparation 19 (63 mg, 0.14 mmol), potassium tert-butoxide (48 mg, 0.42 mmol) and KHMDS (168 mg, 0.84 mmol) in tert-butanol (5 ml) was heated to reflux for 9 days. The mixture was concentrated in vacuo and dissolved in water (5 ml). The pH of the solution was adjusted to 6 with 2M HCl and was extracted with EtOAc (2×50 ml). The organic phases were combined, dried (MgSO$_4$), filtered and concentrated in vacuo. The crude product was purified by column chromatography (DCM/MeOH/NH$_3$, 95:5:0.5) to afford the title compound as a solid (3 mg, 0.007 mmol, 5%); mp 283–286° C.

$^1$H NMR (400 MHz, d$_6$-DMSO) δ 13.70 (br s, 1H), 12.80 (br s, 1H), 8.55 (d, 1H), 8.15 (s, 1H), 7.95 (d, 1H), 7.75 (t, 1H), 7.50 (two multiplets, 2H), 7.30 (t, 1H), 5.45 (s, 2H), 3.20 (s, 3H), 2.80 (m, 2H), 1.25 (t, 3H). MS (TSP) m/z 426 (MH+). High resolution MS m/z calcd for C$_{20}$H$_{20}$N$_5$O$_4$S: 426.1231; found: 426.1224 (MH+).

Example 7

3-Ethyl-5-[2-isobutoxy-5-(methylsulfonyl)phenyl]-1-[(1-methyl-1H-imidazol-2-yl)methyl]-1,6-dihydro-7H-pyrazolo[4,3-d]pyrimidin-7-one

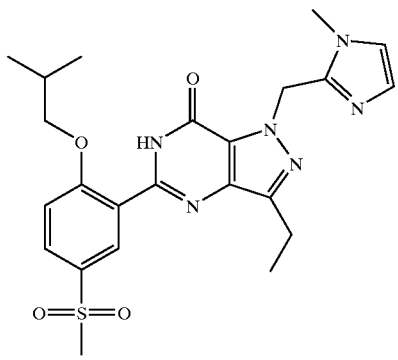

A mixture of the title compound of preparation 20 (120 mg, 0.24 mmol), potassium tert-butoxide (80 mg, 0.72 mmol) and isobutyl acetate (83 mg, 0.72 mmol) in isobutanol (8 ml) was stirred at 100° C. for 10 h. The mixture was concentrated in vacuo and dissolved in water (8 ml). The pH of the solution was adjusted to 6 with 2M HCl and the precipitate was filtered and dried to afford the title compound (85 mg, 0.18 mmol, 73%); mp 253–254° C.

$^1$H NMR (400 MHz, d$_6$-DMSO) δ 12.20 (br s, 1H), 8.00 (s, 1H), 7.95 (d, 1H), 7.35 (d, 1H), 7.05 (s, 1H), 6.70 (s,1H), 5.75 (s, 2H), 3.90 (d, 2H), 3.65 (s, 3H), 3.20 (s, 3H), 2.75 (q, 2H), 1.95 (nonet, 1H), 1.20 (t, 3H), 0.90 (d, 6H). MS (TSP) m/z 485 (MH+). High resolution MS m/z calcd for C$_{23}$H$_{29}$N$_6$O$_4$S: 485.1966; found: 4485.1980 (MH+).

Example 8

5-[2-Butoxy-5-(methylsulfonyl)phenyl]-3-ethyl-2-[2-(4-morpholinyl)ethyl]-2,6-dihydro-7H-pyrazolo[4,3-d]pyrimidin-7-one

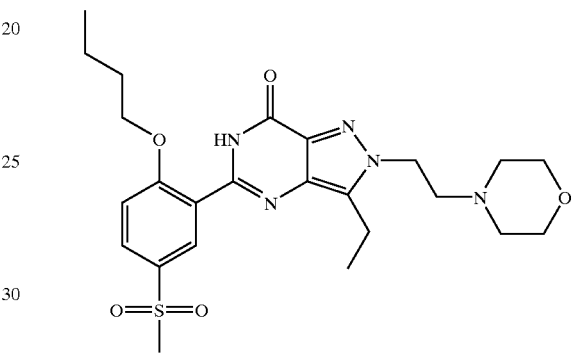

Prepared in 67% yield from the title compound of preparation 24 by following the procedure used for the synthesis of the title compound of example 5; mp 235–238° C.

$^1$H NMR (400 MHz, d$_6$-DMSO) δ 11.65 (br s, 1H), 8.00 (s, 1H), 7.95 (d, 1H), 7.30 (d, 1H), 4.35 (t, 2H), 4.10 (t, 2H), 3.50 (m, 4H), 3.15 (s, 3H), 2.95 (q, 2H), 2.75 (t, 2H), 2.40 (m, 4H), 1.65 (quintet, 2H), 1.35 (sextet, 2H), 1.25 (t, 3H), 0.80 (t, 3H). MS (TSP) m/z 504 (MH+). Anal. Calcd for C$_{24}$H$_{33}$N$_5$O$_5$S.0.75H$_2$O: C, 55.74; H, 6.72; N, 13.54. Found: C, 55.72; H, 6.53; N, 13.28.

Example 9

3-Ethyl-5-[2-isobutoxy-5-(methylsulfonyl)phenyl]-2-[(1-methyl-1H-imidazol-2-yl)methyl]-2,6-dihydro-7H-pyrazolo[4,3-d]pyrimidin-7-one

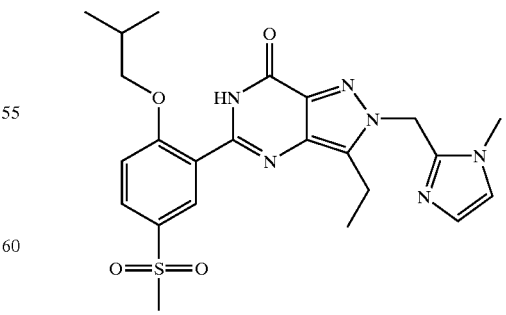

Prepared in 62% yield from the title compound of preparation 25 by following the procedure used for the synthesis of the title compound of example 7; mp 253–254° C.

¹H NMR (400 MHz, d₆-DMSO) δ 11.70 (s, 1H), 8.00 (s, 1H), 7.95 (d, 1H), 7.30 (d, 1H), 7.10 (s, 1H), 6.80 (s, 1H), 5.60 (s, 2H), 3.90 (d, 2H), 3.70 (s, 3H), 3.15 (s, 3H), 3.00 (q, 2H), 1.95 (nonet,1H), 1.20 (t, 3H), 0.85 (d, 6H). MS (TSP) m/z 485 (MH⁺). Anal. Calcd for $C_{23}H_{28}N_6O_4S \cdot 0.75H_2O$: C, 55.46; H, 5.97; N, 16.88. Found: C, 55.40; H, 5.94; N, 16.70.

Example 10

3-Ethyl-5-[2-isobutoxy-5-(methylsulfonyl)phenyl]-2-[2-(4-morpholinyl)ethyl]-2,6-dihydro-7H-pyrazolo[4,3-d]pyrimidin-7-one

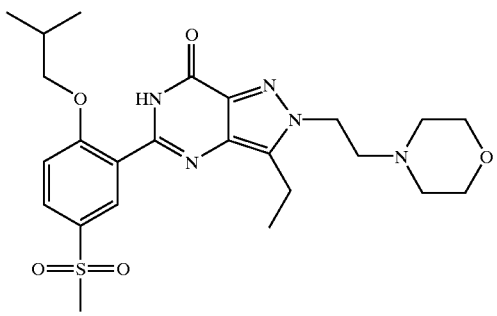

Prepared in 72% yield from the title compound of preparation 26 by following the procedure used for the synthesis of the title compound of example 7; mp 268–273° C.

¹H NMR (400 MHz, d₆-DMSO) δ 11.65 (s, 1H), 8.00 (s, 1H), 7.95 (d, 1H), 7.30 (d, 1H), 4.35 (t, 2H), 3.90 (d, 2H), 3.50 (m, 4H), 3.20 (s, 3H), 2.90 (q, 2H), 2.75 (t, 2H), 2.40 (m, 4H), 1.95 (nonet, 1H), 1.25 (t, 3H), 0.90 (d, 6H). MS (TSP) m/z 504 (MH⁺). Anal. Calcd for $C_{24}H_{33}N_5O_5S \cdot 0.5H_2O$: C, 56.23; H, 6.69; N, 13.66. Found: C, 56.49; H, 6.74; N, 13.28.

Example 11

3-Ethyl-5-[5-(methylsulfonyl)-2-propoxyphenyl]-1-(2-pyridinylmethyl)-1,6-dihydro-7H-pyrazolo[4,3-d]pyrimidin-7-one

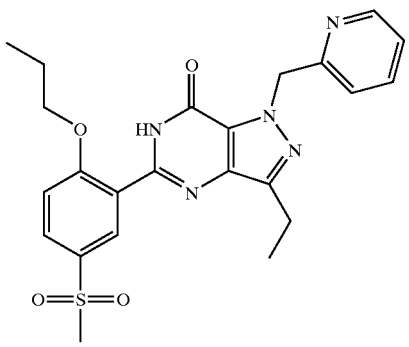

Prepared in 40% yield from the title compound of preparation 29 by following a procedure analogous to that used for the synthesis of the title compound of example 4, but using propanol as the solvent and propyl acetate as the potassium hydroxide scavenger; mp 209–211° C.

¹H NMR (300 MHz, CDCl₃) δ 10.90 (brs, 1H), 9.05 (s, 1H), 8.60 (d, 1H), 8.05 (d, 1H), 7.60 (t, 1H), 7.20 (two obscured multiplets, 2H), 7.05 (d, 1H), 5.95 (s, 2H), 4.30 (t, 2H), 3.15 (s, 3H), 3.05 (q, 2H), 2.05 (sextet, 2H), 1.45 (t, 3H), 1.20 (t, 3H). Anal. Calcd for $C_{23}H_{25}N_5O_4S$: C, 59.08; H, 5.39; N, 14.98. Found: C, 58.80; H, 5.35; N, 14.88.

Example 12

2-(Cyclopropylmethyl)-3-ethyl-5-[5-(methylsulfonyl)-2-propoxyphenyl]-2,6-dihydro-7H-pyrazolo[4,3-d]pyrimidin-7-one

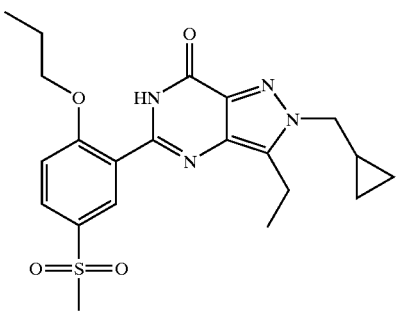

Prepared in 32% yield from the title compound of preparation 33 by following the procedure used for the synthesis of the title compound of example 11; mp 233–234° C.

¹H NMR (300 MHz, CDCl₃): δ 10.55 (br s, 1H), 9.00 (s, 1H), 8.00 (d, 1H), 7.20 (d, 1H), 4.25 (t, 2H), 4.20 (d, 2H), 3.15 (s, 3H), 3.10 (q, 2H), 2.05 (sextet, 2H), 1.45 (t, 3H), 1.40 (obscured multiplet, 1H), 1.15 (t, 3H), 1.10 (t, 3H), 0.65 (m, 2H), 0.50 (m, 2H). MS (TSP) m/z 431 (MH⁺). Anal. Calcd for $C_{21}H_{26}N_4O_4S$: C, 58.58; H, 6.09; N, 13.01. Found C, 58.25; H, 6.08; N, 12.81.

Example 13

3-Ethyl-5-[2-isobutoxy-5-(methylsulfonyl)phenyl]-1-{[(2S)-1-methylpyrrolidinyl]methyl}-1,6-dihydro-7H-pyrazolo[4,3-d]pyrimidin-7-one

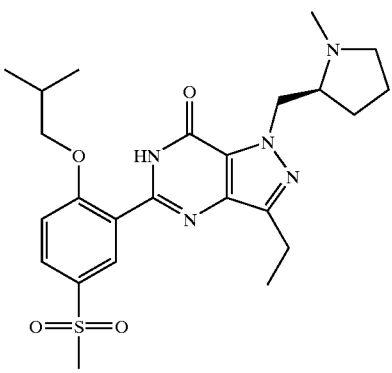

3-Ethyl-4-{[2-isobutoxy-5-(methylsulfonyl)benzoyl]amino}-1-{[(2S)-1-methylpyrrolidinyl]methyl}-1H-pyrazole-5-carboxamide was prepared by reacting the title compound of preparation 9 with title compound of preparation 37 using the same method used to synthesise the title compound of preparation 7. This intermediate was partially purified by column chromatography (DCM/MeOH, 95:5–93:7), and then cyclised to the title compound by following the procedure used to prepare the title compound of example 3 (22% yield over two steps); mp 190–194° C.

¹H NMR (400 MHz, CDCl₃) δ 10.80 (br s, 1H), 9.05 (s, 1H), 8.00 (d, 1H), 7.20 (d, 1H), 4.70 (dd, 1H), 4.50 (dd, 1H), 4.10 (d, 2H), 3.10 (s, 3H), 3.10 (obscured multiplet, 1H), 3.00 (q, 2H), 2.80 (m, 1H), 2.40 (s, 3H), 2.40 (obscured multiplet, 1H), 2.25 (m, 1H), 1.70–1.80 (m, 4H), 1.40 (t, 3H), 1.20 (d, 6H). MS (TSP) m/z 488 (MH$^+$). Anal. Calcd for $C_{24}H_{33}N_5O_4S.0.4H_2O$: C, 58.26; H, 6.89; N, 14.15. Found C, 58.53; H, 6.83; N, 14.27.

Example 14

3-Ethyl-5-[2-isobutoxy-5-(methylsulfonyl)phenyl]-2-{[(2R)-1-methylpyrrolidinyl]methyl}-2,6-dihydro-7H-pyrazolo[4,3-d]pyrimidin-7-one

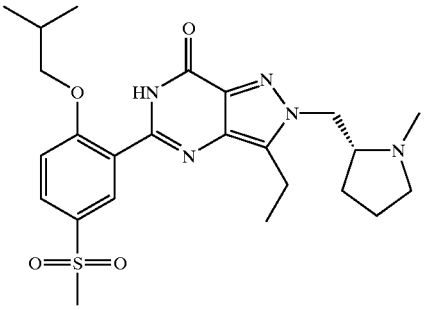

5-Ethyl-4-{[2-isobutoxy-5-(methylsulfonyl)benzoyl]amino}-1-{[(2R)-1-methylpyrrolidinyl]methyl}-1H-pyrazole-3-carboxamide was prepared by reacting the title compound of preparation 9 with title compound of preparation 42 using the same method used to synthesise the title compound of preparation 7. This intermediate was partially purified by column chromatography (DCM/MeOH, 93:7), and then cyclised to the title compound by following the procedure used to prepare the title compound of example 3 (12% yield over two steps); mp 178–180° C.

$^1$H NMR (400 MHz, CDCl$_3$) δ 10.45 (br s, 1H), 8.90 (s, 1H), 8.00 (d, 1H), 7.15 (d, 1H), 4.35 (dd, 1H), 4.15 (dd, 1H), 4.00 (d, 2H), 3.10 (s, 3H), 3.10 (obscured multiplet, 4H), 2.30 (obscured multiplet, 2H), 2.25 (s, 3H), 1.80 (m, 1H), 1.60–1.80 (m, 3H), 1.40 (t, 3H), 1.10 (d, 6H). MS (TSP) m/z 488 (MH$^+$). Anal. Calcd for $C_{24}H_{33}N_5O_4S.0.4H_2O$: C, 58.26; H, 6.89; N, 14.15. Found C, 58.60; H, 6.80; N, 14.32.

Example 15

3-Ethyl-5-[2-isobutoxy-5-(methylsulfonyl)phenyl]-2-(3-pyridazinylmethyl)-2,6-dihydro-7H-pyrazolo[4,3-d]pyrimidin-7-one

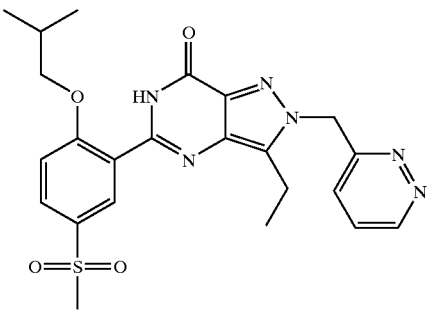

Prepared as a white solid in 54% yield from the title compound of preparation 46 by following the procedure used for the synthesis of the title compound of example 3; mp 244–247° C.

$^1$H NMR (400 MHz, CDCl$_3$) δ 10.60 (br s, 1H), 9.20 (d, 1H), 8.95 (s, 1H), 8.00 (d, 1H), 7.50 (d, 1H), 7.45 (m, 1H), 7.20 (d, 1H), 5.90 (s, 2H), 4.05 (d, 2H) 3.10 (s, 3H), 3.10 (obscured multiplet, 2H), 2.35 (nonet, 1H), 1.30 (t, 3H), 1.15 (d, 6H). MS (ES+) m/z 505 (MNa$^+$), 483 (MH$^+$). Anal. Calcd for $C_{23}H_{26}N_6O_4S.0.05H_2O$: C, 57.14; H, 5.44; N, 17.38. Found: C, 56.82; H, 5.38; N, 17.14.

Example 16

3-Ethyl-5-[2-isobutoxy-5-(methylsulfonyl)phenyl]-1-(3-pyridazinylmethyl)-1,6-dihydro-7H-pyrazolo[4,3-d]pyrimidin-7-one

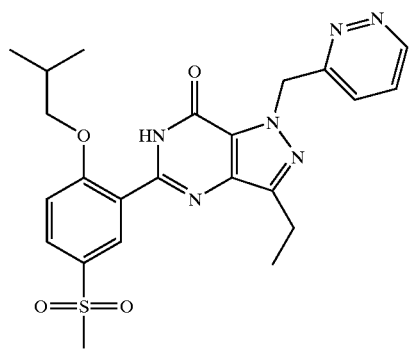

Prepared as a white solid in 71% yield from the title compound of preparation 48 by following the procedure used for the synthesis of the title compound of example 3; mp 231–234° C.

$^1$H NMR (400 MHz, CDCl$_3$) δ 11.00 (br s, 1H), 9.10 (d, 1H), 9.05 (s, 1H), 8.00 (d, 1H), 7.40 (m, 1H), 7.25 (obscured multiplet, 1H), 7.20 (d, 1H), 6.15 (s, 2H), 4.10 (d, 2H), 3.10 (s, 3H), 3.00 (q, 2H), 2.35 (nonet, 1H), 1.40 (t, 3H), 1.15 (d, 6H). MS (ES+) m/z 505 (MNa$^+$), 483 (MH$^+$). Anal. Calcd for $C_{23}H_{26}N_6O_4S$: C, 57.24; H, 5.43; N, 17.42. Found: C, 56.99; H, 5.29; N, 17.25.

Example 17

3-Ethyl-5-[2-isobutoxy-5-(methylsulfonyl)phenyl]-2-(2-pyridinylmethyl)-2,6-dihydro-7H-pyrazolo[4,3-d]pyrimidin-7-one

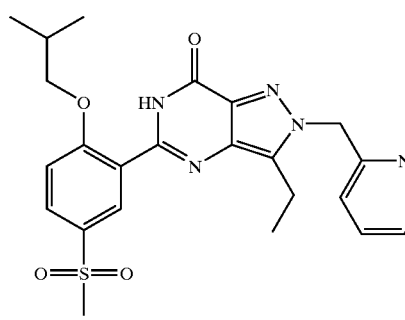

Prepared in 15% yield from the title compound of preparation 49 by following the procedure used for the synthesis of the title compound of example 3 with the exception that the reaction mixture was heated at reflux for 7 days; mp 235–238° C.

¹H NMR (300 MHz, CDCl₃) δ 10.60 (brs, 1H), 8.95 (s, 1H), 8.60 (d, 1H), 8.00 (d, 1H), 7.65 (t, 1H), 7.20 (obscured multiplets, 2H), 7.10 (d, 1H), 5.70 (s, 2H), 4.05 (d, 2H), 3.10 (s, 3H), 3.05 (q, 2H), 2.35 (nonet, 1H), 1.30 (t, 3H), 1.15 (d, 6H). MS (ES+) m/z 504 (MNa⁺), 482 (MH⁺). Anal. Calcd for C₂₄H₂₇N₅O₄S.0.06DCM: C, 59.14; H, 5.58; N, 14.37. Found: C, 59.37; H, 5.62; N, 14.28.

Example 18

3-Ethyl-1-{[(2S)-1-methylpyrrolidinyl]methyl}-5-[5-(methylsulfonyl)-2-propoxyphenyl]-1,6-dihydro-7H-pyrazolo[4,3-d]pyrimidin-7-one

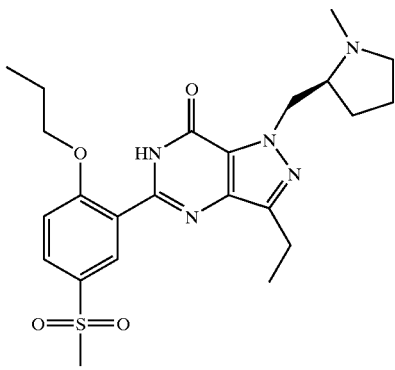

A mixture of the title compound of preparation 50 (149 mg, 0.30 mmol), potassium tert-butoxide (102 mg, 9.1 mmol) and propyl acetate (31 mg, 0.30 mmol) in propanol (4 ml) was heated to reflux for 4 h. The reaction mixture was concentrated in vacuo, dissolved in water (10 ml), neutralised by adding solid CO₂ and then extracted with DCM (2×20 ml). The organic phases were combined, dried (Na₂SO₄), filtered and concentrated in vacuo. The residue was triturated with Et₂O (3 ml), filtered and dried to afford the title compound as a white solid (67 mg, 0.14 mmol, 47%); mp 211–215° C.; [α]$_D^{25}$ –21 (c 1.66, MeOH).

¹H NMR (400 MHz, CDCl₃) δ 10.80 (br s, 1H), 9.05 (s, 1H), 8.00 (d, 1H), 7.20 (d, 1H), 4.70 (dd, 1H), 4.50 (dd, 1H), 4.30 (t, 2H), 3.10 (s, 3H), 3.10 (obscured multiplet, 1H), 3.00 (q, 2H), 2.80 (m, 1H), 2.35 (s, 3H), 2.25 (m, 1H), 2.05 (sextet, 2H), 1.80 (m, 3H), 1.70 (m, 1H), 1.40 (t, 3H), 1.15 (t, 3H). MS (ES+) m/z 496 (MNa⁺), 474 (MH⁺). Anal. Calcd for C₂₃H₃₁N₅O₄S: C, 58.33; H, 6.60; N, 14.79. Found: C, 58.10; H, 6.57; N, 14.63.

Example 19

5-[2-Butoxy-5-(methylsulfonyl)phenyl]-3-ethyl-2-(1-isopropyl-3-azetidinyl)-2,6-dihydro-7H-pyrazolo[4,3-d]pyrimidin-7-one

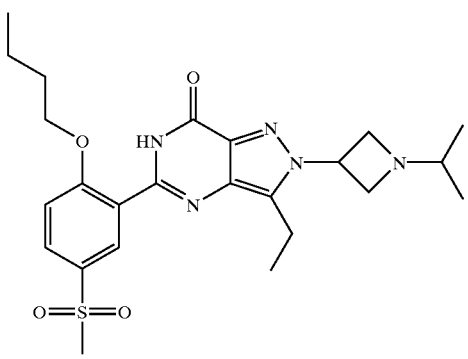

A mixture of the title compound of preparation 55 (150 mg, 0.30 mmol), potassium tert-butoxide (130 mg, 1.16 mmol) and butyl acetate (103 mg, 0.89 mmol) in butanol (8 ml) was heated at 100° C. for 18 h and then at 120° C. for 4 h. The mixture was concentrated in vacuo, and the residue dissolved in water (5 ml). The pH was adjusted to 7 with 2M HCl, and was then extracted with EtOAc (2×15 ml). The organic phases were combined, dried (MgSO₄), filtered and concentrated in vacuo. The residue was triturated with Et₂O (10 ml), filtered and dried to afford the title compound as a white solid (100 mg, 0.21 mmol, 68%); mp 209–213° C.

¹H NMR (400 MHz, d₆-DMSO) δ 11.70 (s, 1H), 8.05 (s, 1H), 8.00 (d, 1H), 7.40 (d, 1H), 5.20 (quintet, 1H), 4.15 (t, 2H), 3.75 (m, 2H), 3.50 (m, 2H), 3.20 (s, 3H), 3.20 (obscured multiplet, 1H), 2.90 (q, 2H), 1.70 (quintet, 2H), 1.40 (sextet, 2H), 1.20 (t, 3H), 0.90 (d, 6H), 0.85 (t, 3H). MS (TSP) m/z 488 (MH⁺). Anal. Calcd for C₂₄H₃₃N₅O₄S.0.3H₂O: C, 58.47; H, 6.87; N, 14.20. Found: C, 58.36; H, 6.83; N, 13.98.

Example 20

3-Ethyl-5-[2-isobutoxy-5-(methylsulfonyl)phenyl]-1-(1-isopropyl-3-azetidinyl)-1,6-dihydro-7H-pyrazolo[4,3-d]pyrimidin-7-one

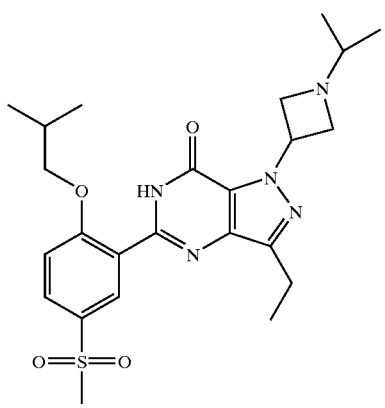

Prepared as a white solid in 75% yield from the title compound of preparation 58 by following the procedure used for the synthesis of the title compound of preparation 3, except that it was purified by triturating from Et$_2$O; mp 206–209° C.

$^1$H NMR (400 M Hz, CDCl$_3$) δ 10.80 (s, 1H), 9.00 (s, 1H), 8.00 (d, 1H), 7.15 (d, 1H), 5.75 (quintet, 1H), 4.05 (d, 2H), 3.90 (t, 2H), 3.60 (t, 2H), 3.10 (s, 3H), 3.00 (q, 2H), 2.60 (septet, 1H), 2.30 (nonet, 1H), 1.40 (t, 3H), 1.15 (d, 6H), 1.00 (d, 6H). MS (TSP) m/z 488 (MH$^+$). Anal. Calcd for C$_{24}$H$_{33}$N$_5$O$_4$S.0.1H125H$_2$O: C, 58.84; H, 6.84; N, 14.30. Found: C, 58.71; H, 6.85; N, 14.16.

Example 21

3-Ethyl-5-[2-isobutoxy-5-(methylsulfonyl)phenyl]-2-(1-methyl-4-piperidinyl)-2,6-dihydro-7H-pyrazolo[4,3-d]pyrimidin-7-one

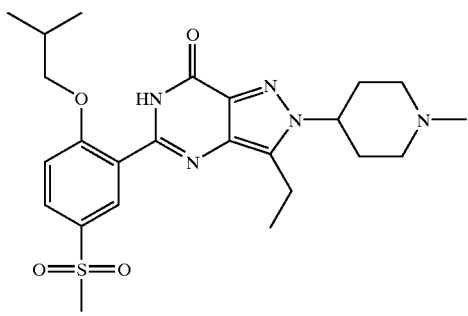

Formaldehyde (30 μl of a 37% aqu. solution, 0.36 mmol) was added to a solution of the title compound of preparation 62 (50 mg, 0.11 mmol) in DCM (5 ml) and the solution was stirred at 20° C. for 15 min. NaBH(OAc)$_3$ (70 mg, 0.33 mmol) was added and the mixture stirred for a further 1 h. The mixture was partitioned between DCM (5 ml) and sat. NaHCO$_3$ soln. (5 ml), and the organic phase was dried (Na$_2$SO$_4$), filtered and concentrated in vacuo to give a clear oil. This was recrystallised from EtOAc to afford the title compound as a white solid (19 mg, 0.039 mmol, 35%); mp 292–295° C.

$^1$H NMR (400 MHz, CDCl$_3$) δ 10.40 (s,1H), 8.90 (s, 1H), 8.00 (d,1H), 7.20 (d, 1H), 4.20 (m, 1H), 4.00 (d, 2H), 3.10 (s, 3H), 3.05 (m, 4H), 2.55 (q, 2H), 2.35 (s, 3H), 2.35 (m, 1H), 2.15 (t, 2H), 1.90 (d, 2H), 1.40 (t, 3H), 1.10 (d, 6H). MS (ES+) m/z 488 (MH$^+$). High resolution MS m/z calcd for C$_{24}$H$_{34}$N$_5$O$_4$S: 488.2326; found: 488.2306 (MH$^+$).

Example 22

3-Ethyl-5-[2-isobutoxy-5-(methylsulfonyl)phenyl]-2-(1-isopropyl-4-piperidinyl)-2,6-dihydro-7H-pyrazolo[4,3-d]pyrimidin-7-one

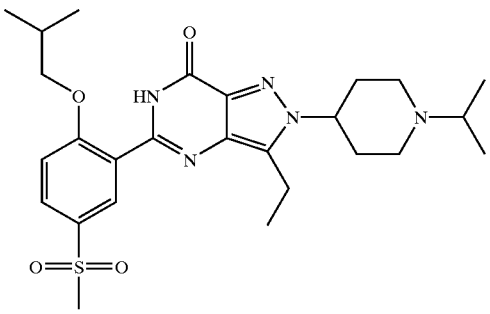

Prepared as a white solid in 26% yield from the title compound of preparation 62 following the same method used to prepare the title compound of example 21 except that acetone was used in place of formaldehyde, and the reaction was stirred at 20° C. for 2 days; mp 273–275° C.

$^1$H NMR (400 MHz, CDCl$_3$) δ 10.40 (s, 1H), 8.90 (s, 1H), 8.00 (d, 1H), 7.15 (d, 1H), 4.20 (m, 1H), 4.00 (d, 2H), 3.10 (s, 3H), 3.05 (m, 4H), 2.80 (septet, 1H), 2.45 (q, 2H), 2.30 (m, 3H), 1.90 (d, 2H), 1.35 (t, 3H), 1.10 (d, 6H), 1.00 (d, 6H). MS (ES+) m/z 538 (MNa$^+$). Anal. Calcd for C$_{26}$H$_{37}$N$_5$O$_4$S.0.8H$_2$0.0.4Et$_2$O: C, 59.23; H, 7.67; N, 12.51. Found: C, 59.38; H, 7.32; N, 12.74.

Example 23

3-Ethyl-1-{[(2S)-1-methylpyrrolidinyl]methyl}-5-[5-(methylsulfonyl)-2-propoxy-3-pyridinyl]-1,6-dihydro-7H-pyrazolo[4,3-d]pyrimidin-7-one

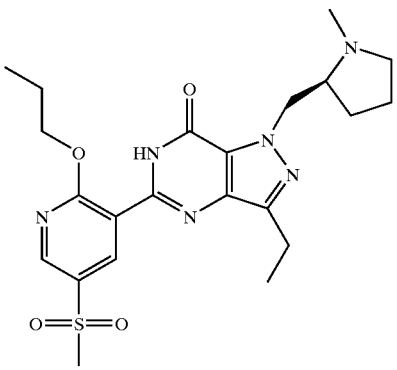

Prepared from the title compound of preparation 68 using the same method used to prepare the title compound of example 21 from the title compound of preparation 62, except the crude product was purified by column chromatography (DCM/MeOH, 97:3 to 92:8); mp 182–183° C.; [α]$_D^{25}$ –20 (c 1.66, MeOH). Note, pyridyl sulphones covered within the scope of this patent can be made by an analogous method.

$^1$H NMR (400 MHz, CDCl$_3$) δ 9.30 (s, 1H), 8.80 (s, 1H), 4.70 (dd, 1H), 4.65 (t, 2H), 4.50 (dd, 1H), 3.15 (s, 3H), 3.10 (m, 1H), 3.00 (q, 2H), 2.80 (m, 1H), 2.40 (s, 3H), 2.25 (m,

1H), 2.00 (sextet, 2H), 1.70–1.80 (m, 4H), 1.40 (t, 3H), 1.15 (t, 3H). MS (TSP) m/z 475 (MH$^+$). Anal. Calcd for $C_{22}H_{30}N_6O_4S\cdot 0.1H_2O$: C, 55.47; H, 6.39; N, 17.64. Found: C, 55.18; H, 6.36; N, 17.38.

Example 24

1-[2-(Diisopropylamino)ethyl]-3-ethyl-5-[5-(methylsulfonyl)-2-propoxyphenyl]-1,6-dihydro-7H-pyrazolo[4,3-d]pyrimidin-7-one

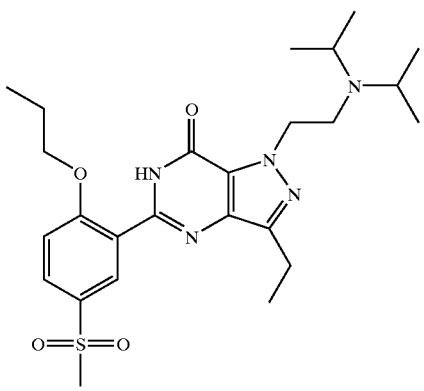

A mixture of the title compound of preparation 72 (300 mg, 0.77 mmol), 2-chloroethyldiisopropylamine hydrochloride (160 mg, 0.80 mmol) and $K_2CO_3$ (400 mg, 2.9 mmol) in N,N-dimethylformamide (3 ml) was stirred at 20° C. for 18 h. The mixture was partitioned between EtOAc (50 ml) and $H_2O$ (50 ml), and the organic phase was washed again with $H_2O$ (50 ml), dried ($Na_2SO_4$), filtered and concentrated in vacuo to afford a mixture of N-(2-{3-ethyl-7-methoxy-5-[5-(methylsulfonyl)-2-propoxyphenyl]-1H-pyrazolo[4,3-d]pyrimidin-1-yl}ethyl)-N-isopropyl-2-propanamine and N-(2-{3-ethyl-7-methoxy-5-[5-(methylsulfonyl)-2-propoxyphenyl]-2H-pyrazolo[4,3-d]pyrimidin-2-yl}ethyl)-N-isopropyl-2-propanamine in an approximate 5:1 ratio.

6M HCl (10 ml) was added to this mixture of regioisomers and the reaction was stirred at 65° C. for 16 h and then at 20° C. for 2 days. The mixture was diluted with $H_2O$ (50 ml), neutralised with $NaHCO_3$ and extracted with DCM (2×50 ml). The organic phase was dried ($Na_2SO_4$), filtered and concentrated in vacuo. The mixture of products was separated by column chromatography (EtOAc) to afford 1-[2-(diisopropylamino)ethyl]-3-ethyl-5-[5-(methylsulfonyl)-2-propoxyphenyl]-1,6-dihydro-7H-pyrazolo[4,3-d]pyrimidin-7-one (higher running spot, 160 mg, 0.32 mmol, 41%) and 2-[2-(diisopropylamino)ethyl]-3-ethyl-5-[5-(methylsulfonyl)-2-propoxyphenyl]-2,6-dihydro-7H-pyrazolo[4,3-d]pyrimidin-7-one (lower running spot, 10 mg, 0.02 mmol, 3%). Assignment of the regioisomers was on the basis of nOe experiments.

Example 24 mp 188–190° C.

$^1$H NMR (400 MHz, CDCl$_3$) δ 10.70 (br s, 1H), 9.00 (s, 1H), 8.00 (d, 1H), 7.20 (d, 1H), 4.60 (t, 2H), 4.25 (t, 2H), 3.10 (s, 3H), 3.00 (m, 4H), 2.90 (t, 2H), 2.05 (sextet, 2H), 1.40 (t, 3H), 1.20 (t, 3H), 0.95 (d, 12H). MS (ES–) m/z 502 (M–H$^+$). Anal. Calcd for $C_{25}H_{37}N_5O_4S$: C, 59.61; H, 7.40; N, 13.91. Found: C, 59.53; H, 7.43; N, 13.89.

Example 25 mp 194–195° C.

$^1$H NMR (400 MHz, CDCl$_3$) δ 10.50 (br s, 1H), 8.95 (s, 1H), 8.00 (d, 1H), 7.15 (d, 1H), 4.20 (m, 4H), 3.10 (s, 3H), 3.05 (obscured m, 2H), 2.95 (m, 4H), 2.00 (sextet, 2H), 1.40 (t, 3H), 1.10 (t, 3H), 0.95 (d, 12H). MS (ES–) m/z 502 (M–H$^+$). Anal. Calcd for $C_{25}H_{37}N_5O_4S$: C, 59.61; H, 7.40; N, 13.91. Found: C, 59.23; H, 7.36; N, 13.73.

Example 25

2,6-dihydro-7H-pyrazolo[4,3-d]pyrimidin-7-one

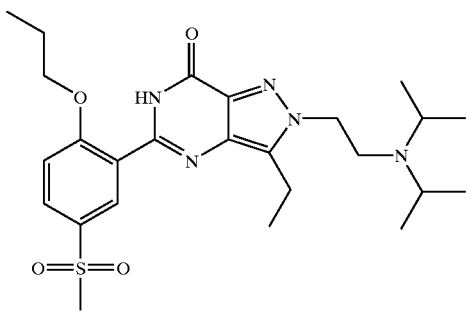

Example 26

3-Ethyl-5-[5-(ethylsulfonyl)-2-propoxyphenyl]-1-{[(2S)-1-methylpyrrolidinyl]methyl}-1,6-dihydro-7H-pyrazolo[4,3-d]pyrimidin-7-one

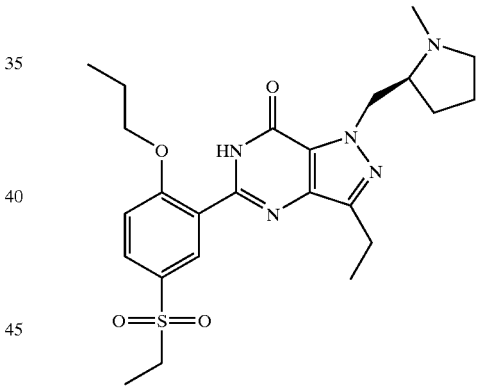

Formaldehyde (37% aqueous soln., 0.3 ml, 4.2 mmol) and Et$_3$N (0.08 ml, 0.6 mmol) were added to the title compound of preparation 78 (147 mg, 0.25 mmol) in THF (5 ml) and stirred for 15 min at 20° C. NaBH(OAc)$_3$ (192 mg, 0.9 mmol) and AcOH (0.01 ml) were added and the mixture was stirred at 20° C. for 18 h. $H_2O$ (5 ml) and EtOAc (10 ml) were added and the mixture basified with NaHCO$_3$. The organic phase was separated, dried (MgSO$_4$), filtered, concentrated and triturated with Et$_2$O to afford the title compound (36 mg, 0.074 mmol, 30%).

$^1$H NMR (400 MHz, CDCl$_3$) δ 10.80 (br s, 1H), 8.95 (s, 1H), 7.95 (d, 1H), 7.15 (d, 1H), 4.70 (dd, 1H), 4.40 (dd, 1H), 4.25 (t, 2H), 3.15 (q, 2H), 3.05 (m, 1H), 2.95 (q, 2H), 2.75 (m, 1H), 2.35 (s, 3H), 2.25 (m, 1H), 2.00 (sextet, 2H), 1.80 (m, 3H), 1.70 (m, 1H), 1.35 (t, 3H), 1.30 (t, 3H), 1.15 (t, 3H). MS (TSP) m/z 488 (MH$^+$). Anal. Calcd for $C_{24}H_{33}N_5O_4S\cdot 0.25H_2O$: C, 58.58; H, 6.86; N, 14.23. Found: C, 58.53; H, 6.80; N, 13.89.

Example 27

3-Ethyl-5-[5-(isopropylsulfonyl)-2-propoxyphenyl]-1-{[(2S)-1-methylpyrrolidinyl]methyl}-1,6-dihydro-7H-pyrazolo[4,3-d]pyrimidin-7-one

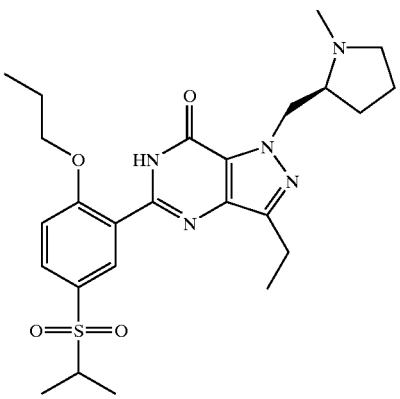

Prepared as a white solid in 30% yield from the title compound of preparation 82 by following the procedure used to prepare the title compound of example 26.

$^1$H NMR (400 MHz, CDCl$_3$) δ 10.80 (br s, 1H), 8.95 (s, 1H), 7.95 (d, 1H), 7.15 (d, 1H), 4.70 (dd, 1H), 4.45 (dd, 1H), 4.25 (t, 2H), 3.25 (septet, 1H), 3.05 (m, 1H), 2.95 (q, 2H), 2.75 (m, 1H), 2.35 (s, 3H), 2.20 (m, 1H), 2.00 (sextet, 2H), 1.80 (m, 3H), 1.70 (m, 1H), 1.35 (t, 3H), 1.30 (d, 6H), 1.15 (t, 3H). MS (TSP) m/z 502 (MH$^+$). High resolution MS m/z calcd for C$_{25}$H$_{35}$N$_5$O$_4$S: 502.2483; found: 502.2483 (MH$^+$).

Example 28

3-Ethyl-1-{[(2S)-1-methylpiperidinyl]methyl}-5-[5-(methylsulfonyl)-2-propoxyphenyl]-1,6-dihydro-7H-pyrazolo[4,3-d]pyrimidin-7-one

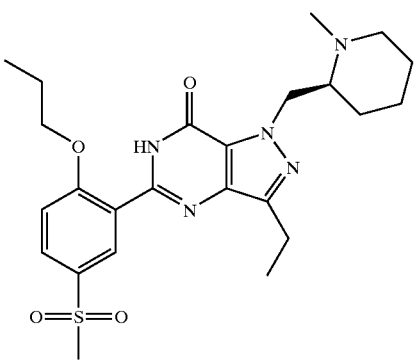

Formed as a white solid in 13% yield from the title compound of preparation 84 by following the method used to prepare the title compound of example 26, except the crude product was purified by column chromatography (DCM/MeOH/NH$_{3(aq)}$, 98:2:10 to 92:8:10) and trituration with Et$_2$O.

$^1$H NMR (400 MHz, CDCl$_3$) δ 9.05 (s, 1H), 8.00 (d, 1H), 7.20 (d, 1H), 4.90 (dd, 1H), 4.50 (dd, 1H), 4.30 (t, 2H), 3.10 (s, 3H), 3.00 (q, 2H), 2.85 (m, 1H), 2.65 (m, 1H), 2.45 (s, 3H), 2.20 (m, 1H), 2.05 (sextet, 2H), 1.50–1.70 (m, 4H), 1.4 (t, 3H), 1.35 (m, 2H), 1.20 (t, 3H). MS (TSP) m/z 488 (MH$^+$). High resolution MS m/z calcd for C$_{24}$H$_{33}$N$_5$O$_4$S: 488.2326; found: 488.2320 (MH$^+$).

Example 29

5-Allyl-2-[2-butoxy-5-(methylsulfonyl)phenyl]-7-ethylimidazo5,1-f][1,2,4]triazin-4(3H)-one

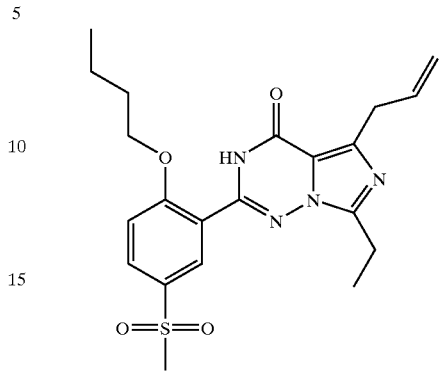

POCl$_3$ (0.15 ml, 1.6 mmol) was added to a solution of the title compound of preparation 95 (90 mg, 0.20 mmol) in 1,2-dichloroethane (2 ml) and the mixture was heated to reflux for 30 min. After cooling, DCM (40 ml) and 5% Na$_2$CO$_3$ soln. (10 ml) were added, and the mixture was thoroughly shaken. The phases were separated and the aqueous phase extracted with DCM (20 ml). The combined organics were dried (Na$_2$SO$_4$), filtered and concentrated in vacuo. The crude product was purified by column chromatography (pentane/EtOAc, 60:40–25:75) and crystallised from Et$_2$O to afford the title compound (50 mg, 0.12 mmol, 60%); mp 192–194° C.

$^1$H NMR (400 MHz, CDCl$_3$) δ 9.70 (s, 1H), 8.70 (s, 1H), 8.05 (d, 1H), 7.20 (d, 1H), 6.10 (ddt, 1H), 5.20 (d, 1H), 5.10 (d, 2H), 4.30 (t, 2H), 3.80 (d, 2H), 3.10 (s, 3H), 3.05 (obscured m, 2H), 2.00 (quintet, 2H), 1.60 (sextet, 2H), 1.40 (t, 3H), 1.05 (t, 3H). MS (ES–) m/z 429 (M–H$^+$). Anal. Calcd for C$_{21}$H$_{26}$N$_4$O$_4$S: C, 58.59; H, 6.09; N, 13.01. Found: C, 58.37; H, 6.04; N, 12.91.

Biological Activity

Table 1 illustrates the in vitro CGMP PDE5 inhibitory activities for a range of compounds of the invention.

TABLE 1

| Example | IC$_{50}$ (nM) |
|---|---|
| 1 | 5.6 |
| 2 | 6.5 |
| 3 | 1.5 |
| 5 | 3.5 |
| 7 | 1.7 |
| 8 | 10.0 |
| 9 | 3.95 |
| 10 | 7.6 |
| 11 | 1.4 |
| 12 | 1.0 |
| 13 | 6.3 |
| 14 | 8.3 |
| 15 | 7.3 |
| 16 | 9.8 |
| 17 | 4.8 |
| 18 | 5.4 |
| 19 | 6.6 |
| 20 | 13.7 |
| 21 | 12.5 |
| 22 | 13.4 |
| 24 | 6.7 |
| 25 | 5.4 |

TABLE 1-continued

| Example | IC$_{50}$ (nM) |
| --- | --- |
| 26 | 18.3 |
| 28 | 3.6 |
| 29 | 6.7 |

In Vitro Metabolism Data

HLM half-lives of examples 1 and 12 of the present invention are illustrated in

TABLE 2

| Example | HLM t$_{1/2}$ (min.) |
| --- | --- |
| 1 | 67 |
| 12 | >120 |

What is claimed is:

1. A compound of general formula I:

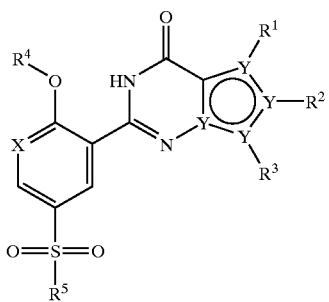

or a pharmaceutically or veterinarily acceptable salt and/or solvate thereof, wherein Y represents C or N, with N being in at least one, but not more than two, of the positions marked by Y;

X represents CH or N;

$R^1$, $R^2$ and $R^3$ where present and attached to nitrogen independently represent H, $C_1-C_6$ alkyl, Het, $C_1-C_6$ alkylHet, aryl or $C_1-C_6$ alkylaryl;

$R^1$, $R^2$ and $R^3$ where present and attached to carbon independently represent H, halo, cyano, nitro, $OR^6$, $OC(O)R^6$, $C(O)R^6$, $C(O)OR^6$, $NR^6C(O)NR^7R^8$, $NR^6C(O)OR^6$, $OC(O)NR^7R^8$, $C(O)NR^9R^{10}$, $NR^9R^{10}$, $SO_2NR^9R^{10}$, $SO_2R^{11}$, $C_1-C_6$ alkyl, Het, $C_1-C_6$ alkylHet, aryl or $C_1-C_6$ alkylaryl;

$R^4$ represents H, $C_1-C_6$ alkyl, Het, $C_1-C_6$ alkylHet, aryl or $C_1-C_6$ alkylaryl;

$R^5$ represents $C_1-C_6$ alkyl, Het, $C_1-C_6$ alkylHet, aryl or $C_1-C_6$ alkylaryl;

wherein when $R^1$, $R^2$ and $R^3$, where present, or $R^4$ or $R^5$ is a $C_1-C_6$ alkyl, Het, $C_1-C_6$ alkylHet, aryl and $C_1-C_6$ alkylaryl group, such $C_1-C_6$ alkyl, Het, $C_1-C_6$ alkylHet, aryl and $C_1-C_6$ alkylaryl group is optionally substituted and/or terminated with one or more substituents selected from halo, cyano, nitro, $OR^6$, $OC(O)R^6$, $C(O)R^6$, $C(O)OR^6$, $NR^6C(O)NR^7R^8$, $NR^6C(O)OR^6$, $OC(O)NR^7R^8$, $C(O)NR^9R^{10}$, $NR^9R^{10}$, $SO_2NR^9R^{10}$, $SO_2R^{11}$, $C_1-C_6$ alkyl, Het, $C_1-C_6$ alkylHet, aryl or $C_1-C_6$ alkylaryl which latter five substituent groups are all optionally substituted and/or terminated with one or more substituents selected from halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$, $SO_2R^{17}$;

$R^6$ represents H, $C_1-C_6$ alkyl, Het, $C_1-C_6$ alkylHet, aryl or $C_1-C_6$ alkylaryl which latter five substituent groups are all optionally substituted and/or terminated with one or more substituents selected from halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$, $SO_2R^{17}$;

$R^7$ and $R^8$ independently represent H, $C_1-C_6$ alkyl, Het, $C_1-C_6$ alkylHet, aryl or $C_1-C_6$ alkylaryl which latter five substituent groups are all optionally substituted and/or terminated with one or more substituents selected from halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$, $SO_2R^{17}$, or $R^7$ and $R^8$ together with the nitrogen atom to which they are bound can form a heterocyclic ring which is optionally substituted and/or terminated with one or more substituents selected from halo, cyano, nitro, $OR^{12}$, $OC(O)R^{12}$, $C(O)R^{12}$, $C(O)OR^{12}$, $NR^{12}(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$, $SO_2R^{17}$;

$R^9$ and $R^{10}$ independently represent H, $C(O)R^6$, $SO_2R^{11}$, $C_1-C_6$ alkyl, Het, $C_1-C_6$ alkylHet, aryl or $C_1-C_6$ alkylaryl which latter five substituent groups are all optionally substituted and/or terminated with one or more substituents selected from halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$, $SO_2R^{17}$; or $R^9$ and $R^{10}$ together with the nitrogen atom to which they are bound can form a heterocyclic ring which is optionally substituted and/or terminated with one or more substituents selected from halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$, $SO_2R^{17}$;

$R^{11}$ represents $C_1-C_6$ alkyl, Het, $C_1-C_6$ alkylHet, aryl or $C_1-C_6$ alkylaryl which latter five substituent groups are all optionally substituted and/or terminated with one or more substituents selected from halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$, $SO_2R^{17}$;

$R^{12}$ represents H or $C_1-C_6$ alkyl;

$R^{13}$ and $R^{14}$ independently represent H or $C_1-C_6$ alkyl; or $R^{13}$ and $R^{14}$ together with the nitrogen atom to which they are bound can form a heterocyclic ring;

$R^{15}$ and $R^{16}$ independently represent H, $C(O)R^{12}$, $SO_2R^{17}$ or $C_1-C_6$ alkyl; or $R^{15}$ and $R^{16}$ together with the nitrogen atom to which they are bound can form a heterocyclic ring;

$R^{17}$ represents $C_1-C_6$ alkyl;

Het represents an optionally substituted four- to twelve-membered heterocyclic group, which group contains one or more heteroatoms selected from nitrogen, oxygen, sulfur and mixtures thereof and with the proviso that when $R^5$ is Het, said Het is C-linked to the sulphur atom of the $SO_2$ group in general formula I.

2. A compound according to claim 1 selected from formulae IA, IB, IC, ID and IE:

IA

IB

IC

ID

IE wherein:
X represents CH or N;
$R^1$, $R^2$ and $R^3$ where present and attached to nitrogen independently represent H, $C_1$–$C_6$ alkyl, Het, $C_1$–$C_6$ alkylHet, aryl or $C_1$–$C_6$ alkylaryl;
$R^1$, $R^2$ and $R^3$ where present and attached to carbon independently represent H, halo, cyano, nitro, $OR^6$, $OC(O)R^6$, $C(O)R^6$, $C(O)R^6$, $NR^6C(O)NR^7R^8$, $NR^6C(O)OR^6$, $OC(O)NR^7R^8$, $C(O)NR^9R^{10}$, $NR^9R^{10}$, $SO_2NR^9R^{10}$, $SO_2R^{11}$, $C_1$–$C_6$, alkyl, Het, $C_1$–$C_6$ alkylHet, aryl or $C_1$–$C_6$ alkylaryl;
wherein when $R^1$ and $R^2$ are present they may optionally be connected via a C—C, C—N or C—O bond;
wherein when $R^2$ and $R^3$ are present they may optionally be connected via a C—C, C—N or C—O bond;
$R^4$ represents H, $C_1$–$C_6$ alkyl, Het, $C_1$–$C_6$ alkylHet, aryl or $C_1$–$C_6$ alkylaryl;
$R^5$ represents $C_1$–$C_6$ alkyl, Het, $C_1$–$C_6$ alkylHet, aryl or $C_1$–$C_6$ alkylaryl;
wherein when $R^1$, $R^2$ and $R^3$, where present, or $R^4$ or $R^5$ is a $C_1$–$C_6$ alkyl, Het, $C_1$–$C_6$ alkylHet, aryl and $C_1$–$C_6$ alkylaryl group, such $C_1$–$C_6$ alkyl, Het, $C_1$–$C_6$ alkylHet, aryl and $C_1$–$C_6$ alkylaryl group is optionally substituted and/or terminated with one or more substituents selected from halo, cyano, nitro, $OR^6$, $OC(O)R^6$, $C(O)R^6$, $C(O)OR^6$, $NR^6C(O)NR^7R^8$, $NR^6C(O)OR^6$, $OC(O)NR^7R^8$, $C(O)NR^9R^{10}$, $NR^9R^{10}$, $SO_2NR^9R^1$, $SO_2R^{11}$, $C_1$–$C_6$ alkyl, Het, $C_1$–$C_6$ alkylHet, aryl or $C_1$–$C_6$ alkylaryl which latter five substituent groups are all optionally substituted and/or terminated with one or more substituents selected from halo, cyano, nitro, OR, OC(O)R, C(O)R, C(O)OR, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$, $SO_2R^{17}$;
$R^6$ represents H, $C_1$–$C_6$ alkyl, Het, $C_1$–$C_6$ alkylHet, aryl or $C_1$–$C_6$ alkylaryl which latter five substituent groups are all optionally substituted and/or terminated with one or more substituents selected from halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$, $SO_2R^{17}$;
$R^7$ and $R^8$ independently represent H, $C_1$–$C_6$ alkyl, Het, $C_1$–$C_6$ alkylHet, aryl or $C_1$–$C_6$ alkylaryl which latter five substituent groups are all optionally substituted and/or terminated with one or more substituents selected from halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$, $SO_2R^{17}$; or
$R^7$ and $R^8$ together with the nitrogen atom to which they are bound can form a heterocyclic ring which is optionally substituted and/or terminated with one or more substituents selected from halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$, $SO_2R^{17}$;
$R^9$ and $R^{10}$ independently represent H, $C(O)R^6$, $SO_2R^{11}$, $C_1$–$C_6$ alkyl, Het, $C_1$–$C_6$ alkylHet, aryl or $C_1$–$C_6$ alkylaryl which latter five substituent groups are all optionally substituted and/or terminated with one or more substituents selected from halo, cyano, nitro, $OR^{12}$, $OC(O)R^{12}$, $C(O)R^{12}$, $C(O)OR^{12}$, $NR^{12}C(O)NR^{13}R^{14}$, $NR^{12}C(O)OR^{12}$, $OC(O)NR^{13}R^{14}$, $C(O)NR^{15}R^{16}$, $NR^{15}R^{16}$, $SO_2NR^{15}R^{16}$, $SO_2R^{17}$; or R$^9$ and R$^{10}$ together with the nitrogen atom to which they are bound can form a heterocyclic ring which is optionally substituted and/or terminated with one or more substituents selected from halo, cyano, nitro, OR$^{12}$, OC(O)R$^{12}$, C(O)R$^{12}$, C(O)OR$^{12}$, NR$^{12}$C(O)NR$^{13}$R$^{14}$, NR$^{12}$C(O)OR$^{12}$, OC(O)NR$^{13}$R$^{14}$, C(O)NR$^{15}$R$^{16}$, NR$^{15}$R$^{16}$, SO$_2$NR$^{15}$R$^{16}$, SO$_2$R$^{17}$;

R$^{11}$ represents C$_1$–C$_6$ alkyl, Het, C$_1$–C$_6$ alkylHet, aryl or C$_1$–C$_6$ alkylaryl which latter five substituent groups are all optionally substituted and/or terminated with one or more substituents selected from halo, cyano, nitro, OR$^{12}$, OC(O)R$^{12}$, C(O)R$^{12}$, C(O)OR$^{12}$, NR$^{12}$C(O)NR$^{13}$R$^{14}$, NR$^{12}$C(O)OR$^{12}$, OC(O)NR$^{13}$R$^{14}$, C(O)NR$^{15}$R$^{16}$, NR$^{15}$R$^{16}$, SO$_2$NR$^{15}$R$^{16}$, SO$_2$R$^{17}$;

R$^{12}$ represents H or C$_1$–C$_6$ alkyl;

R$^{13}$ and R$^{14}$ independently represent H or C$_1$–C$_6$ alkyl; or

R$^{13}$ and R$^{14}$ together with the nitrogen atom to which they are bound can form a heterocyclic ring;

R$^{15}$ and R$^{16}$ independently represent H, C(O)R$^{12}$, SO$_2$R$^{17}$ or C$_1$–C$_6$ alkyl; or R$^{15}$ and R$^{16}$ together with the nitrogen atom to which they are bound can form a heterocyclic ring;

R$^{17}$ represents C$_1$–C$_6$ alkyl;

Het represents an optionally substituted four- to twelve-membered heterocyclic group, which group contains one or more heteroatoms selected from nitrogen, oxygen, sulfur and mixtures thereof with the proviso that where R$^5$ is Het then said Het is C-linked to the sulphur atom of the SO$_2$ group in general formula I and with the proviso that R$^3$ does not represent H in formula IE where X is CH;

with the proviso that in formula 1A or 1D when X is N, R$^5$ does not represent C$_1$–C$_6$ alkyl, optionally substituted and/or terminated with one or more substituents selected from halo, OR$^{17}$, NR$^{12}$R$^{17}$ or NR$^{17}$C(O)R$^{17}$.

3. A compound according to claim 1 wherein;

X represents CH or N;

R$^1$, R$^2$ and R$^3$, where present, independently represent C$_1$–C$_6$ alkyl, Het, C$_1$–C$_6$ alkylHet, aryl or C$_1$–C$_6$ alkylaryl optionally substituted and/or terminated with one or more substituents selected from halo, OR$^6$, C(O)OR$^6$ and NR$^9$R$^{10}$;

R$^4$ represents C$_1$–C$_6$ alkyl, Het, C$_1$–C$_6$ alkylHet, aryl or C$_1$–C$_6$ alkylaryl optionally substituted and/or terminated with one or more substituents selected from halo and OR$^6$;

R$^5$ represents C$_1$–C$_6$ alkyl, Het, C$_1$–C$_6$ alkylHet, aryl or C$_1$–C$_6$ alkylaryl wherein said groups are all optionally substituted and/or terminated with one or more substituents selected from halo, OR$^6$, C(O)OR$^6$ and NR$^9$R$^{10}$;

wherein R$^6$, R$^9$ and R$^{10}$ are as defined in claim 1;

with the proviso that when R$^5$ is Het, said Het is C-linked to the sulphur atom of the SO$_2$ group in general formula I; and with the proviso that R$^3$ does not represent H in formula IE when X is CH; and with the proviso that in formula 1A or 1D when X is N, R$^5$ does not represent C$_1$–C$_6$ alkyl, optionally substituted and/or terminated with one or more substituents selected from halo, OR$^{17}$, NR$^{12}$R$^{17}$ or NR$^{17}$C(O)R$^{17}$.

4. A compound according to claim 2 wherein:

X represents CH;

R$^1$, R$^2$ and R$^3$, where present, independently represent C$_1$–C$_6$ alkyl, Het or C$_1$–C$_6$ alkylHet optionally substituted and/or terminated with one or more substituents selected from OR$^6$, C$_1$–C$_6$ alkyl and NR$^9$R$^{10}$;

R$^4$ represents C$_1$–C$_6$ alkyl, C$_1$–C$_6$ alkylHet, optionally substituted and/or terminated with OR$^6$;

R$^5$ represents C$_1$–C$_6$ alkyl optionally substituted and/or terminated with one or more substituents selected from halo, OR$^6$, C(O)OR$^6$ and NR$^9$R$^{10}$;

with the proviso that in formula 1A or 1D when X is N, R$^5$ does not represent C$_1$–C$_6$ alkyl, optionally substituted and/or terminated with one or more substituents selected from halo, OR$^{17}$, NR$^{12}$R$^{17}$ or NR$^{17}$C(O)R$^{17}$.

5. A compound according to claim 1 and having general formula IG wherein:

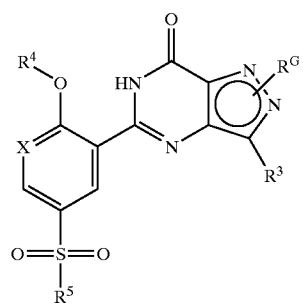

IG wherein:

X represents CH or N;

R$^G$ is R$^1$ or R$^2$;

R$^1$, R$^2$ and R$^3$, where present, independently represent C$_1$–C$_6$ alkyl, Het or C$_1$–C$_6$ alkylHet optionally substituted and/or terminated with one or more substituents selected from OR$^6$, C$_1$–C$_6$ alkyl and NR$^9$R$^{10}$;

R$^4$ represents C$_1$–C$_6$ alkyl, C$_1$–C$_6$ alkylHet, optionally substituted and/or terminated with OR$^6$;

R$^5$ represents C$_1$–C$_6$ alkyl optionally substituted and/or terminated with one or more substituents selected from halo, OR$^6$, C(O)OR$^6$ and NR$^9$R$^{10}$;

wherein R$^6$, R$^9$ and R$^{10}$ are as defined in claim 1 with the proviso that when X is N, R$^5$ does not represent C$_1$–C$_6$ alkyl, optionally substituted and/or terminated with one or more substituents selected from halo, OR$^{17}$, NR$^{12}$R$^{17}$ or NR$^{17}$C(O)R$^{17}$.

6. A compound according to claim 5 wherein:

X represents CH;

R$^G$ is R$^1$ and represents C$_1$–C$_3$ alkyl or C$_1$–C$_3$ alkylHet wherein said C$_1$–C$_3$ alkyl group is optionally substituted and/or terminated with one or more substituents selected from halo, OR$^6$, C(O)OR$^6$ and NR$^9$R$^{10}$ and wherein said C$_1$–C$_3$ alkylHet group is optionally substitued and/or terminated with one or more substituents selected from halo, C$_1$–C$_6$ alkyl, OR$^6$, C(O)OR$^6$ and NR$^9$R$^{10}$;

R$^3$ represents C$_1$–C$_6$ alkyl optionally substituted and/or terminated with one or more substituents selected from halo and OR$^6$;

R$^4$ represents C$_1$–C$_6$ alkyl or C$_1$–C$_6$ alkylHet optionally substituted and/or terminated with one or more substituents selected from halo and OR$^6$;

R⁵ represents $C_1$–$C_6$ alkyl optionally substituted and/or terminated with one or more substituents selected from halo and OR⁶;

and R⁶, R⁹ and R¹⁰ are as defined in claim 5.

7. A compound according to claim 5 wherein:

X represents CH;

R^G represents R¹ which represents methyl, ethyl or $C_1$–$C_3$ alkylHet wherein said $C_1$–$C_3$ alkylHet group is optionally substituted and/or terminated with one or more substituents selected from halo, $C_1$–$C_6$ alkyl, OR⁶, C(O)OR⁶ and NR⁹R¹⁰;

R³ represents $C_2$–$C_4$ alkyl;

R⁴ represents $C_2$–$C_4$ alkyl optionally substituted and/or terminated with one or more substituents selected from halo and OR⁶;

R⁵ represents $C_1$–$C_4$ alkyl;

wherein R⁶, R⁹ and R¹⁰ are independently selected from methyl or ethyl groups.

8. A compound according to claim 5 wherein:

X represents CH;

R^G represents R² and is $C_1$–$C_6$ alkyl, Het or $C_1$–$C_3$ alkylHet wherein said $C_1$–$C_6$ alkyl, Het or $C_1$–$C_3$ alkylHet groups are optionally substitued and/or terminated with one or more substituents selected from halo, $C_1$–$C_6$ alkyl, OR⁶, C(O)OR⁶ and NR⁹R¹⁰ and wherein when R² represents $C_1$–$C_6$ alkyl, said alkyl group may be straight chain, branched chain or part or wholly cyclic;

R³, R⁴ and R⁵ independently represent $C_1$–$C_6$ alkyl optionally substituted and/or terminated with one or more substituents selected from halo and OR⁶;

wherein R⁶ and R⁹ and R¹⁰ are as defined in claim 5.

9. A compound according to claim 5 wherein:

X represents CH; R^G represents R² and is $C_1$–$C_5$ alkyl, Het or alkylHet wherein the Het groups of said Het or alkylHet is a C-linked Het group which is optionally substitued and/or terminated with one or more substituents selected from halo, $C_1$–$C_6$ alkyl, OR⁶, C(O)OR⁶ and NR⁹R¹⁰;

R³ represents $C_2$–$C_4$ alkyl;

R⁴ represents $C_2$–$C_4$ alkyl;

R⁵ represents $C_1$–$C_4$ alkyl;

wherein R⁶, R⁹ and R¹⁰ are independently selected from methyl or ethyl groups.

10. A compound according to claim 5 wherein:

X is CH;

when R^G is R¹, R^G represents $C_1$–$C_3$ alkyl or R^G represents $C_1$–$C_6$ alkylHet; or when R^G is R², R^G represents $C_1$–$C_6$ alkylHet, Het or $C_1$–$C_6$ alkyl wherein said Het is C-linked;

R³ is $C_1$–$C_6$ alkyl;

R⁴ is $C_1$–$C_6$ alkyl;

R⁵ is $C_1$–$C_3$ alkyl.

11. A compound selected from:

5-[2-Ethoxy-5-(methylsulfonyl)phenyl]-1-methyl-3-propyl-1,6-dihydro-7H-pyrazolo[4,3-d]pyrimidin-7-one;

5-[2-Butoxy-5-(methylsulfonyl)phenyl]-3-ethyl-2-(2-methoxyethyl)-2,6-dihydro-7H-pyrazolo[4,3-d]pyrimidin-7-one;

3-Ethyl-5-[2-isobutoxy-5-(methylsulfonyl)phenyl]-1-(2-pyridinylmethyl)-1,6-dihydro-7H-pyrazolo[4,3-d]pyrimidin-7-one;

5-[2-Butoxy-5-(methylsulfonyl)phenyl]-3-ethyl-1-(2-pyridinylmethyl)-1,6-dihydro-7H-pyrazolo[4,3-d]pyrimidin-7-one;

3-Ethyl-5-[2-isobutoxy-5-(methylsulfonyl)phenyl]-1-[(1-methyl-1H-imidazol-2-yl)methyl]-1,6-dihydro-7H-pyrazolo[4,3-d]pyrimidin-7-one;

5-[2-Butoxy-5-(methylsulfonyl)phenyl]-3-ethyl-2-[2-(4-morpholinyl)ethyl]-2,6-dihydro-7H-pyrazolo[4,3-d]pyrimidin-7-one;

3-Ethyl-5-[2-isobutoxy-5-(methylsulfonyl)phenyl]-2-[(1-methyl-1H-imidazol-2-yl)methyl]-2,6-dihydro-7H-pyrazolo[4,3-d]pyrimidin-7-one;

3-Ethyl-5-[2-isobutoxy-5-(methylsulfonyl)phenyl]-2-[2-(4-morpholinyl)ethyl]-2,6-dihydro-7H-pyrazolo[4,3-d]pyrimidin-7-one;

3-Ethyl-5-[5-(methylsulfonyl)-2-propoxyphenyl]-1-(2-pyridinylmethyl)-1,6-dihydro-7H-pyrazolo[4,3-d]pyrimidin-7-one;

2-(Cyclopropylmethyl)-3-ethyl-5-[5-(methylsulfonyl)-2-propoxyphenyl]-2,6-dihydro-7H-pyrazolo[4,3-d]pyrimidin-7-one;

3-Ethyl-5-[2-isobutoxy-5-(methylsulfonyl)phenyl]-1-{[(2S)-1-methylpyrrolidinyl]methyl}-1,6-dihydro-7H-pyrazolo[4,3-d]pyrimidin-7-one;

3-Ethyl-5-[2-isobutoxy-5-(methylsulfonyl)phenyl]-2-{[(2R)-1-methylpyrrolidinyl]methyl}-2,6-dihydro-7H-pyrazolo[4,3-d]pyrimidin-7-one;

3-Ethyl-5-[2-isobutoxy-5-(methylsulfonyl)phenyl]-2-(3-pyridazinylmethyl)-2,6-dihydro-7H-pyrazolo[4,3-d]pyrimidin-7-one;

3-Ethyl-5-[2-isobutoxy-5-(methylsulfonyl)phenyl]-1-(3-pyridazinylmethyl)-1,6-dihydro-7H-pyrazolo[4,3-d]pyrimidin-7-one;

3-Ethyl-5-[2-isobutoxy-5-(methylsulfonyl)phenyl]-2-(2-pyridinylmethyl)-2,6-dihydro-7H-pyrazolo[4,3-d]pyrimidin-7-one;

3-Ethyl-1-{[(2S)-1-methylpyrrolidinyl]methyl}-5-[5-(methylsulfonyl)-2-propoxyphenyl]-1,6-dihydro-7H-pyrazolo[4,3-d]pyrimidin-7-one;

5-[2-Butoxy-5-(methylsulfonyl)phenyl]-3-ethyl-2-(1-isopropyl-3-azetidinyl)-2,6-dihydro-7H-pyrazolo[4,3-d]pyrimidin-7-one;

3-Ethyl-5-[2-isobutoxy-5-(methylsulfonyl)phenyl]-1-(1-isopropyl-3-azetidinyl)-1,6-dihydro-7H-pyrazolo[4,3-d]pyrimidin-7-one;

3-Ethyl-5-[2-isobutoxy-5-(methylsulfonyl)phenyl]-2-(1-methyl-4-piperidinyl)-2,6-dihydro-7H-pyrazolo[4,3-d]pyrimidin-7-one;

3-Ethyl-5-[2-isobutoxy-5-(methylsulfonyl)phenyl]-2-(1-isopropyl-4-piperidinyl)-2,6-dihydro-7H-pyrazolo[4,3-d]pyrimidin-7-one;

1-[2-(Diisopropylamino)ethyl]-3-ethyl-5-[5-(methylsulfonyl)-2-propoxyphenyl]-1,6-dihydro-7H-pyrazolo[4,3-d]pyrimidin-7-one;

2-[2-(Diisopropylamino)ethyl]-3-ethyl-5-[5-(methylsulfonyl)-2-propoxyphenyl]-2,6-dihydro-7H-pyrazolo[4,3-d]pyrimidin-7-one;

3-Ethyl-5-[5-(ethylsulfonyl)-2-propoxyphenyl]-1-{[(2S)-1-methylpyrrolidinyl]methyl}-1,6-dihydro-7H-pyrazolo[4,3-d]pyrimidin-7-one;

3-Ethyl-1-{[(2S)-1-methylpiperidinyl]methyl}-5-[5-(methylsulfonyl)-2-propoxyphenyl]-1,6-dihydro-7H-pyrazolo[4,3-d]pyrimidin-7-one or 5-Allyl-2-[2-butoxy-5-(methylsulfonyl)phenyl]-7-ethylimidazo[5,1-f][1,2,4]triazin-4(3H)-one.

12. A formulation comprising a compound according to claim 1 in admixture with a pharmaceutically or veterinarily acceptable adjuvant, diluent or carrier.

13. A method of treating hypertension, pulmonary hypertension, diabetes, male erectile dysfunction (MED), impotence, female sexual dysfunction (FSD), clitoral dysfunction, female hypoactive sexual desire disorder, female sexual arousal disorder, female sexual pain disorder or female sexual orgasmic dysfunction (FSOD) which comprises administering a therapeutically effective amount of a compound as claimed in claim 1 to a patient in need of such treatment.

* * * * *